United States Patent
Tasaka et al.

(10) Patent No.: US 6,518,257 B1
(45) Date of Patent: Feb. 11, 2003

(54) 1-SUBSTITUTED PHENYL-1-(1H-IMIDAZOL-4-YL) ALCOHOLS, PROCESS FOR PRODUCING THE SAME AND USE THEREOF

(75) Inventors: Akihiro Tasaka, Suita (JP); Tomohiro Kaku, Nishinomiya (JP); Masami Kusaka, Kobe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/111,136

(22) PCT Filed: Oct. 19, 2000

(86) PCT No.: PCT/JP00/07284

§ 371 (c)(1),
(2), (4) Date: Apr. 18, 2002

(87) PCT Pub. No.: WO01/30764

PCT Pub. Date: May 3, 2001

(30) Foreign Application Priority Data

Oct. 22, 1999 (JP) .............................. 11-301562

(51) Int. Cl.$^7$ ................ A61K 31/4164; A61K 31/4178; C07D 233/64; C07D 401/10; C07D 405/10
(52) U.S. Cl. ................ 514/63; 514/341; 514/397; 514/400; 546/275.1; 548/110; 548/312.1; 548/341.1; 548/336.1; 548/341.5; 548/315.4; 548/338.1; 548/342.1; 548/315.1
(58) Field of Search ................ 548/110, 312.1, 548/341.1, 336.1, 341.5, 315.4, 338.1, 342.1, 315.1; 546/275.1; 514/63, 341, 397, 400

(56) References Cited

U.S. PATENT DOCUMENTS 4,544,664 A * 10/1985 Karjalainen et al. ........ 514/396

FOREIGN PATENT DOCUMENTS

| EP | 0721 943 A1 | 7/1996 |
| EP | 0 820 989 A1 | 1/1998 |
| EP | 1 028 110 A1 | 8/2002 |
| WO | WO 95/04723 | 2/1995 |
| WO | WO 99/18075 | 4/1999 |

OTHER PUBLICATIONS

Y. Zhuang, et al. "Novel Imidazolyl and Triazolyl Substituted Biphenyl Compounds: Synthesis and Evaluation as Nonsteroidal Inhibitors of Human 17 α–Hydroxylase–C17, 20–Lyase (P450 17)" Bioorganic & Medicinal Chemistry 8:1245–52 (2000).

* cited by examiner

Primary Examiner—Laura L. Stockton
(74) Attorney, Agent, or Firm—Mark Chao; Elaine M. Ramesh

(57) ABSTRACT

To provide a composition having a steroid $C_{17,20}$-lyase inhibitory activity and useful as an agent for the prophylaxis or treatment of prostatism and tumors such as breast cancer. A compound represented by the formula:

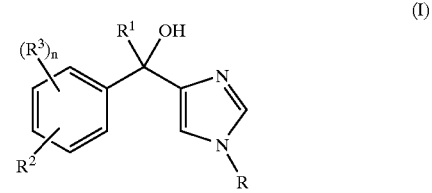

(I)

wherein R is a hydrogen atom or a protecting group, $R^1$ is a lower alkyl group or a cyclic hydrocarbon group, $R^2$ is an aromatic hydrocarbon group optionally having substituents or an aromatic heterocyclic group optionally having substituents, $R^3$ is a hydrocarbon group optionally having substituents, a hydroxyl group optionally having substituents, a thiol group optionally having substituents, an amino group optionally having substituents, an acyl group or a halogen atom, and n is an integer of 0 to 4, and a salt thereof have a steroid $C_{17,20}$-lyase inhibitory activity, and are useful as an agent for the pophylaxis or treatment of prostatism and tumors such as beast cancer and the like.

14 Claims, No Drawings

1-SUBSTITUTED PHENYL-1-(1H-IMIDAZOL-4-YL) ALCOHOLS, PROCESS FOR PRODUCING THE SAME AND USE THEREOF

This application is the National Phase filing of International Patent Application No. PCT/JP00/07284, filed Oct. 19, 2000.

TECHNICAL FIELD

The present invention relates to a pharmaceutical agent, particularly, a novel 1-substituted phenyl-1-(1H-imidazol-4-yl)alcohol having a steroid $C_{17,20}$-lyase inhibitory action and a pharmaceutical composition containing the same.

BACKGROUND ART

Sex hormones have various physiological activities such as differentiation and proliferation of cells and the like. On the other hand, it has been found that androgen and estrogen act as an exacerbation factor in some diseases. It is known that steroid $C_{17,20}$-lyase is involved in the final stage in the biosynthesis of androgen in vivo. That is, steroid $C_{17,20}$-lyase converts, as a substrate, 17-hydroxypregnenolone and 17-hydroxyprogesterone derived from cholesterol to dehydroepiandrosterone and androstenedione, respectively. Therefore, a medicine having a steroid $C_{17,20}$-lyase inhibitory activity suppresses formation of androgen, as well as estrogen produced from androgen as a substrate, and is useful as an agent for the prophylaxis or treatment of diseases whose exacerbation factor is androgen or estrogen. As the disease for which androgen or estrogen is an exacerbation factor, there are mentioned, for example, prostate cancer, prostatic hypertrophy, virilism, hirsutism, male pattern alopecia, precocious puberty, breast cancer, uterine cancer, ovarian cancer, mastopathy, uterus myoma, endometriosis, adenomyosis of uterus, polycystic ovary syndrome, and the like.

Steroid type compounds and non-steroid type compounds are already known as steroid $C_{17,20}$-lyase inhibitors. The steroid type compounds are disclosed in, for example, WO 92/15404, WO 93/20097, EP-A 288053, EP-A 413270 and the like. As non-steroid type compounds, for example, (1H-imidazol-1-yl)methyl-substituted benzimidazole derivatives are shown in Japanese Published Unexamined Patent Application No. 85975/1989, carbazole derivatives are shown in WO94/27989 and WO96/14090, azole derivatives are shown in WO95/09157, 1H-benzimidazole derivatives are shown in U.S. Pat. No. 5,491,161, dihydronaphthalene derivatives are shown in WO99/18075, and (1H-imidazol-1-yl)methylbiphenyl derivatives are shown in Bioorganic Medicinal Chemistry, vol. 7, pp 1913–1924 (1999).

Heretofore, steroid $C_{17,20}$-lyase inhibitors usable for medical purposes have not been obtained, and early development of steroid $C_{17,20}$-lyase inhibitors highly useful as medicine is awaited.

DISCLOSURE OF INVENTION

The present inventors have conducted intensive studies in an attempt to find a superior steroid $C_{17,20}$-lyase inhibitor and first synthesized a novel compound characterized by a chemical structure, wherein a methylene group that connects a benzene ring represented by the formula (I) and an imidazole ring is substituted by lower alkyl or cyclic hydrocarbon group and hydroxyl group, and a salt thereof, and found that the obtained compound (I) and a salt thereof have, based on the specific chemical structure, unexpectedly superior pharmaceutical use, particularly a superior steroid $C_{17,20}$-lyase inhibitory activity, low toxicity and superior properties as a pharmaceutical product, and based on these findings, completed the present invention.

Accordingly, the present invention relates to
(1) a compound represented by the formula:

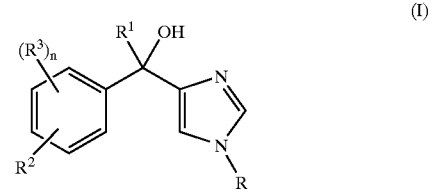

(I)

wherein
R is a hydrogen atom or a protecting group,
$R^1$ is a lower alkyl group or a cyclic hydrocarbon group,
$R^2$ is an aromatic hydrocarbon group optionally having substituents or an aromatic heterocyclic group optionally having substituents,
$R^3$ is a hydrocarbon group optionally having substituents, a hydroxyl group optionally having substituents, a thiol group optionally having substituents, an amino group optionally having substituents, an acyl group or a halogen atom, and
n is an integer of 0 to 4,
or a salt thereof;
(2) the compound of the above-mentioned (1), wherein R is 1) a hydrogen atom, 2) a formyl, 3) a $C_{1-6}$ alkylcarbonyl optionally substituted by 1 to 3 groups selected from Group 1, 4) a phenylcarbonyl optionally substituted by 1 to 3 groups selected from Group 1, 5) a $C_{1-6}$ alkyl-oxycarbonyl optionally substituted by 1 to 3 groups selected from Group 1, 6) a phenyloxycarbonyl optionally substituted by 1 to 3 groups selected from Group 1, 7) a $C_{7-10}$ aralkyloxy-carbonyl optionally substituted by 1 to 3 groups selected from Group 1, 8) a trityl optionally substituted by 1 to 3 groups selected from Group 1, 9) a phthaloyl optionally substituted by 1 to 3 groups selected from Group 1 or 10) a N,N-dimethylaminomethylene optionally substituted by 1 to 3 groups selected from Group 1,
$R^1$ is a $C_{1-6}$ alkyl or a $C_{3-6}$ cycloalkyl,
$R^2$ is a $C_{6-10}$ aryl group optionally substituted by 1 to 4 groups selected from Group 2 or an aromatic heterocyclic group selected from Group 3, which is optionally substituted by 1 to 4 groups selected from Group 2, and
$R^3$ is 1) a $C_{1-4}$ alkyl, 2) a $C_{1-4}$ alkyl having $C_{2-4}$ alkanoyl, carboxyl or $C_{1-4}$ alkoxy-carbonyl as a substituent, 3) a hydroxyl group, 4) a $C_{1-4}$ lower alkoxy, 5) a $C_{1-4}$ alkanoyloxy, 6) a carbamoyloxy, 7) a carbamoyloxy substituted by 1 or 2 $C_{1-4}$ alkyl groups, 8) a thiol group, 9) a $C_{1-4}$ alkylthio group, 10) a $C_{1-4}$ alkanoylthio, 11) an amino group, 12) a $C_{1-4}$ alkylamino group, 13) a di-$C_{1-4}$ alkylamino, 14) a $C_{1-4}$ alkanoylamino, 15) a formyl, 16) a $C_{2-6}$ alkanoyl, 17) a $C_{1-4}$ alkylsulfonyl, 18) a carbamoyl group, 19) a mono- or di-$C_{1-10}$ alkylcarbamoyl, 20) a mono- or di-$C_{6-14}$ arylcarbamoyl, 21) a mono- or di-$C_{7-16}$ aralkylcarbamoyl group, 22) a sulfamoyl, 23) a mono- or di-$C_{1-10}$ alkylsulfamoyl group, 24) a mono- or di-$C_{6-14}$ arylsulfamoyl group, 25) a mono- or di-$C_{7-16}$ aralkylsulfamoyl group or 26) a halogen atom, and wherein, in the above, Group 1 includes
   a halogen atom, a formyl group, a $C_{1-6}$ alkyl-carbonyl group and a nitro group, Group 2 includes
   1) a $C_{1-6}$ alkyl group, 2) a $C_{1-4}$ alkyl group substituted by 1 to 5 halogen atoms, 3) a $C_{1-4}$ alkyl group substituted by 1 or 2 $C_{1-4}$ alkoxy, 4) a hydroxyl group, 5) a $C_{1-4}$ alkoxy group, 6) a $C_{1-4}$ alkanoyloxy group, 7) a carbamoyloxy group, 8) a carbamoyloxy group substituted by $C_{1-4}$ alkyl group, 9) an amino group, 10) a mono- or di-$C_{1-4}$ alkylamino group, 11) a $C_{1-4}$ alkanoylamino group, 12) a formyl group, 13) a $C_{2-6}$ alkanoyl group, 14) a $C_{1-4}$ alkylsulfonyl group, 15) a carbamoyl group, 16) a mono- or di-$C_{1-10}$ alkylcarbamoyl group, 17) a $C_{3-6}$ cycloalkylcarbamoyl group, 18) a mono- or di-$C_{6-14}$ arylcarbamoyl group, 19) a mono- or di-$C_{7-16}$ aralkylcarbamoyl group, 20) a sulfamoyl group, 21) a mono- or di-$C_{1-10}$ alkylsulfamoyl group, 22) a mono- or di-$C_{6-14}$ arylsulfamoyl group, 23) a mono- or di-$C_{7-16}$ aralkylsulfamoyl group, 24) a halogen atom, 25) a cyano group and 26) an oxo group, Group 3 includes
   a 2-thienyl group, a 3-thienyl group, a 2-pyridyl group, a 3-pyridyl group, a 4-pyridyl group, a 2-furyl group, a 3-furyl group, a 2-quinolyl group, a 4-quinolyl group, a 8-quinolyl group, a 3-isoquinolyl group, a 4-isoquinolyl group, a pyrazinyl group, a 2-pyrimidinyl group, a 3-pyrrolyl group, a 1-imidazolyl group, a 2-imidazolyl group, a 1-pyrazolyl group, a 2-thiazolyl group, a 4-thiazolyl group, a 5-thiazolyl group, a 3-isothiazolyl group, a 4-isothiazolyl group, a 2-oxazolyl group, a 4-oxazolyl group, a 5-oxazolyl group, a 3-isoxazolyl group, a 3-pyridazinyl group, a 1-indolyl group, a 1-isoindolyl group, a 2-isoindolyl group, a 1-tetrazolyl group, a 2-tetrazolyl group and a 5-tetrazolyl group;

(3) the compound of the above-mentioned (1), wherein
   R is a hydrogen atom,
   $R^1$ is a $C_{1-6}$ alkyl group or a $C_{3-6}$ cycloalkyl group,
   $R^2$ is a phenyl group, a pyridyl group, a thienyl group, a furyl group or an isoindolinyl group, each optionally substituted by 1 to 4 groups selected from Group 4,
   n is 0 or 1, and
   $R^3$ is a $C_{1-4}$ lower alkoxy group, a $C_{1-4}$ alkanoyloxy group or a $C_{1-4}$ alkanoylamino group,
   and wherein, in the above, Group 4 includes
   1) a $C_{1-6}$ alkyl group, 2) a $C_{1-4}$ alkyl group substituted by 1 to 5 halogen atoms, 3) a $C_{1-4}$ alkyl group substituted by 1 or 2 $C_{1-4}$ alkoxy, 4) a $C_{1-4}$ alkoxy group, 5) a $C_{1-4}$ alkanoylamino group, 6) a $C_{2-6}$ alkanoyl group, 7) a mono- or di-$C_{1-10}$ alkylcarbamoyl group, 8) a $C_{3-6}$ cycloalkylcarbamoyl group, 9) a mono- or di-$C_{1-10}$ alkylsulfamoyl group, 10) a halogen atom, 11) a cyano group and 12) an oxo group;

(4) the compound of the above-mentioned (3), wherein $R^2$ is a phenyl group, a pyridyl group, a thienyl group, a furyl group or an isoindolinyl group, each optionally substituted by 1 or 2 groups selected from Group 5,
and wherein, in the above, Group 5 includes
   1) a $C_{1-4}$ alkanoylamino group, 2) a $C_{2-6}$ alkanoyl group, 3) a mono-$C_{1-10}$ alkylcarbamoyl group, 4) a mono-$C_{1-10}$ alkylsulfamoyl group, 5) a halogen atom and 6) an oxo group;

(5) the compound of the above-mentioned (1), wherein
   R is a hydrogen atom,
   $R^1$ is a $C_{1-6}$ alkyl group,
   $R^2$ is 1) a phenyl group substituted by halogen or acetylamino or 2) a pyridyl group substituted by halogen or acetylamino, and
   n is 0;

(6) the compound of the above-mentioned (1), which is 1-(4'-fluoro[1,1'-biphenyl]-4-yl)-1-(1H-imidazol-4-yl)-2-methyl-1-propanol, (−)-N-(6-{4-[1-hydroxy-1-(1H-imidazol-4-yl)-2-methylpropyl]phenyl}-2-pyridyl)acetamide, (−)-N-{4'-[1-hydroxy-1-1H-imidazol-4-yl)-2-methylpropyl][1,1'-biphenyl]-3-yl}acetamide, 4'-[1-hydroxy-1-(1H-imidazol-4-yl)-2-methylpropyl]-N-methyl[1,1'-biphenyl]-3-carboxamide or N-[4'-[1-hydroxy-1-(1H-imidazol-4-yl)propyl][1,1'-biphenyl]-3-yl]acetamide, or a salt thereof;

(7) a prodrug of a compound represented by the formula:

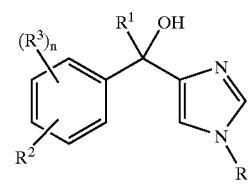

(I)

wherein R is a hydrogen atom or a protecting group, $R^1$ is a lower alkyl group or a cyclic hydrocarbon group, $R^2$ is an aromatic hydrocarbon group optionally having substituents or an aromatic heterocyclic group optionally having substituents, $R^3$ is a hydrocarbon group optionally having substituents, a hydroxyl group optionally having substituents, a thiol group optionally having substituents, an amino group optionally having substituents, an acyl group or a halogen atom, and n is an integer of 0 to 4, or a salt thereof;

(8) a pharmaceutical composition containing a compound represented by the formula:

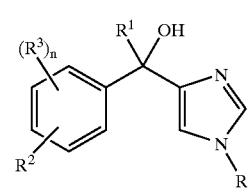

(I)

wherein R is a hydrogen atom or a protecting group, $R^1$ is a lower alkyl group or a cyclic hydrocarbon group, $R^2$ is an aromatic hydrocarbon group optionally having substituents or an aromatic heterocyclic group optionally having substituents, $R^3$ is a hydrocarbon group optionally having substituents, a hydroxyl group optionally having substituents, a thiol group optionally having substituents, an amino group optionally having substituents, an acyl group or a halogen atom, and n is an integer of 0 to 4, a salt thereof or a prodrug thereof;

(9) the composition of the above-mentioned (8), which is a steroid $C_{17,20}$-lyase inhibitor;

(10) the composition of the above-mentioned (9), which is an antitumor agent;

(11) the antitumor composition of the above-mentioned (9), which is an agent for the prophylaxis or treatment of breast cancer or prostate cancer;

(12) an androgen reducer containing a compound represented by the formula:

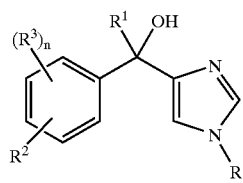

(I)

wherein R is a hydrogen atom or a protecting group, $R^1$ is a lower alkyl group or a cyclic hydrocarbon group, $R^2$ is an aromatic hydrocarbon group optionally having substituents or an aromatic heterocyclic group optionally having substituents, $R^3$ is a hydrocarbon group optionally having substituents, a hydroxyl group optionally having substituents, a thiol group optionally having substituents, an amino group optionally having substituents, an acyl group or a halogen atom, and n is an integer of 0 to 4, or a salt thereof or a prodrug thereof, and an LHRH modulator in combination;

(13) a production method of a compound represented by the formula:

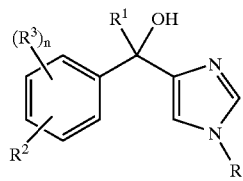

(I)

wherein

R is a hydrogen atom or a protecting group, $R^1$ is a lower alkyl group or a cyclic hydrocarbon group, $R^2$ is an aromatic hydrocarbon group optionally having substituents or an aromatic heterocyclic group optionally having substituents, $R^3$ is a hydrocarbon group optionally having substituents, a hydroxyl group optionally having substituents, a thiol group optionally having substituents, an amino group optionally having substituents, an acyl group or a halogen atom, and n is an integer of 0 to 4, or a salt thereof, which method comprises reacting a compound represented by the formula:

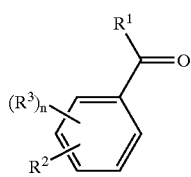

(II)

wherein each symbol is as defined above, with a reaction product of a compound represented by the formula:

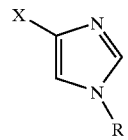

(III)

wherein X is a leaving group and R is as defined above, and a Grignard reagent or alkyllithium;

(14) a method for inhibiting steroid $C_{17,20}$-lyase, which comprises administering, to a mammal, an effective amount of a compound represented by the formula:

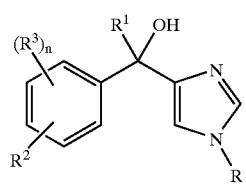

(I)

wherein

R is a hydrogen atom or a protecting group, $R^1$ is a lower alkyl group or a cyclic hydrocarbon group, $R^2$ is an aromatic hydrocarbon group optionally having substituents or an aromatic heterocyclic group optionally having substituents, $R^3$ is a hydrocarbon group optionally having substituents, a hydroxyl group optionally having substituents, a thiol group optionally having substituents, an amino group optionally having substituents, an acyl group or a halogen atom, and n is an integer of 0 to 4, or a salt or a prodrug thereof;

(15) use of a compound represented by the formula:

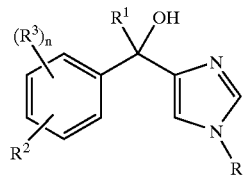

(I)

wherein

R is a hydrogen atom or a protecting group, $R^1$ is a lower alkyl group or a cyclic hydrocarbon group, $R^2$ is an aromatic hydrocarbon group optionally having substituents or an aromatic heterocyclic group optionally having substituents, $R^3$ is a hydrocarbon group optionally having substituents, a hydroxyl group optionally having substituents, a thiol group optionally having substituents, an amino group optionally having substituents, an acyl group or a halogen atom, n is an integer of 0 to 4, or a salt thereof or a prodrug thereof for the production of a steroid $C_{17,20}$-lyase inhibitor; and the like.

In the above formulas, the lower alkyl group represented by $R^1$ is a straight chain or branched alkyl having 1 to 6 carbon atoms. Examples thereof include $C_{1-6}$ alkyl group such as methyl, ethyl, n-propyl, isopropyl, butyl, isobutyl, sec-butyl, tert-butyl, n-pentyl, isopentyl, neopentyl, tert-pentyl, n-hexyl, isohexyl and the like. Examples of the cyclic hydrocarbon group represented by $R^1$ include $C_{3-6}$ cycloalkyl group such as cyclopropyl, cyclobutyl, cyclopentyl, cyclohexyl and the like, and the like. As $R^1$, $C_{1-4}$ alkyl group (e.g., methyl, ethyl, n-propyl, isopropyl, n-butyl, sec-butyl, tertbutyl etc.) and the like are preferable.

Examples of the "aromatic hydrocarbon group" in "aromatic hydrocarbon group optionally having substituents", which is represented by $R^2$, include a monocyclic aromatic hydrocarbon group, a condensed polycyclic aromatic hydrocarbon group and the like, each of which consisting of 6 to 18 carbon atoms. Specific examples thereof include a $C_{6-14}$ aryl group such as phenyl, 1-naphthyl, 2-naphthyl, 2-indenyl, 2-anthryl and the like, with preference given to $C_{6-10}$ aryl group (e.g., phenyl etc.) and the like. Examples of the "aromatic heterocyclic group" in "aromatic heterocyclic group optionally having substituents", which is represented by $R^2$, include 2-thienyl, 3-thienyl, 2-pyridyl, 3-pyridyl, 4-pyridyl, 2-furyl, 3-furyl, 2-quinolyl, 4-quinolyl, 8-quinolyl, 3-isoquinolyl, 4-isoquinolyl, pyrazinyl, 2-pyrimidinyl, 3-pyrrolyl, 1-imidazolyl, 2-imidazolyl, 1-pyrazolyl, 2-thiazolyl, 4-thiazolyl, 5-thiazolyl, 3-isothiazolyl, 4-isothiazolyl, 2-oxazolyl, 4-oxazolyl, 5-oxazolyl, 3-isoxazolyl, 3-pyridazinyl, 1-indolyl, 1-isoindolyl, 2-isoindolyl, 1-tetrazolyl, 2-tetrazolyl, 5-tetrazolyl and the like.

The "substituent" in the "aromatic hydrocarbon group optionally having substituents" and "aromatic heterocyclic group optionally having substituents", which is represented by $R^2$, may be present in the number of 1 to 4 at substitutable positions on the ring. Examples of the substituent include lower($C_{1-6}$)alkyl group (e.g., methyl, ethyl, n-propyl, i-propyl, n-butyl, i-butyl, t-butyl, n-pentyl, n-hexyl and the like), lower alkyl group substituted by 1 to 5 halogen atoms (e.g., fluorine, chlorine and the like), which is exemplified by those having 1 to 4 carbon atoms such as chloromethyl, bromoethyl, fluoromethyl, trichloromethyl, 1-chloroethyl, 2-chloroethyl, 1,1-dichloroethyl, 1,2-dibromoethyl, 1,1,2-trichloropropyl and the like, $C_{1-4}$ alkyl group substituted by 1 or 2 $C_{1-4}$ alkoxy (e.g., methoxymethyl, ethoxymethyl, 1-methoxyethyl, 2-methoxyethyl, 1-ethoxyethyl, 2-ethoxyethyl, dimethoxymethyl and the like), hydroxyl group optionally having substituents [e.g., hydroxyl group, lower alkoxy (e.g., $C_{1-4}$ alkoxy group such as methoxy, ethoxy, propoxy and the like), lower alkanoyloxy (e.g., $C_{1-4}$ alkanoyloxy such as acetyloxy, propionyloxy and the like), carbamoyloxy optionally having substituents (e.g., unsubstituted carbamoyloxy and carbamoyloxy substituted by 1 or 2 $C_{1-4}$ alkyl groups, such as methylcarbamoyloxy, ethylcarbamoyloxy, dimethylcarbamoyloxy, diethylcarbamoyloxy, methylethylcarbamoyloxy and the like) and the like], amino group optionally having substituents [e.g., amino, lower alkylamino (e.g., $C_{1-4}$ alkylamino group such as methylamino, ethylamino, propylamino and the like), di-lower alkylamino (e.g., di-$C_{1-4}$ alkylamino such as dimethylamino, diethylamino and the like), $C_{1-4}$ alkanoylamino (e.g., acetamide, propionamide and the like) and the like], acyl group [e.g., carbamoyl group optionally having substituents (e.g., mono- or di-$C_{1-10}$ alkylcarbamoyl group such as methylcarbamoyl, ethylcarbamoyl, dimethylcarbamoyl, diethylcarbamoyl etc., mono- or di-$C_{6-14}$ arylcarbamoyl such as phenylcarbamoyl, diphenylcarbamoyl etc., mono- or di-$C_{7-16}$ aralkylcarbamoyl group such as benzylcarbamoyl, dibenzylcarbamoyl etc., and the like), alkanoyl group (e.g., $C_{1-6}$ alkanoyl such as formyl, acetyl, propionyl and the like), alkylsulfonyl group (e.g., $C_{1-4}$ alkylsulfonyl such as methylsulfonyl, ethylsulfonyl and the like), carbamoyl group optionally having substituents (e.g., mono- or di-$C_{1-10}$ alkylcarbamoyl group such as methylcarbamoyl, ethylcarbamoyl, dimethylcarbamoyl, diethylcarbamoyl etc., $C_{3-6}$ cycloalkylcarbamoyl such as cyclopropylcarbamoyl, cyclopentylcarbamoyl, cyclohexylcarbamoyl etc., mono- or di-$C_{6-14}$ arylcarbamoyl such as phenylcarbamoyl, diphenylcarbamoyl etc., mono- or di-$C_{7-16}$ aralkylcarbamoyl group such as benzylcarbamoyl, dibenzylcarbamoyl etc., and the like), sulfamoyl optionally having substituents (e.g., mono- or di-$C_{1-10}$ alkylsulfamoyl group such as methylsulfamoyl, ethylsulfamoyl, dimethylsulfamoyl, diethylsulfamoyl etc., mono- or di-$C_{6-14}$ arylsulfamoyl group such as phenylsulfamoyl, diphenylsulfamoyl etc., mono- or di-$C_{7-16}$ aralkylsulfamoyl group such as benzylsulfamoyl, dibenzylsulfamoyl etc., and the like) and the like], halogen atom (fluorine, chlorine, bromine, iodine) and the like.

Examples of the hydrocarbon group optionally having substituents, which is represented by $R^3$, include unsubstituted $C_{1-4}$ alkyl such as methyl, ethyl, propyl etc., these alkyl groups having substituents such as alkanoyl (e.g., acetyl, propionyl etc.), carboxyl, $C_{1-4}$ alkoxy-carbonyl (e.g., methoxycarbonyl, ethoxycarbonyl, butoxycarbonyl etc.) and the like, and the like.

Examples of the hydroxyl group optionally having substituents, which is represented by $R^3$, include unsubstituted hydroxyl group, lower alkoxy (e.g., $C_{1-4}$ alkoxy group such as methoxy, ethoxy, propoxy etc.), lower alkanoyloxy (e.g., $C_{1-4}$ alkanoyloxy such as acetyloxy, propionyloxy etc.), carbamoyloxy optionally having substituents (e.g., unsubstituted carbamoyloxy, carbamoyloxy substituted by 1 or 2 $C_{1-4}$ alkyl groups such as methylcarbamoyloxy, ethylcarbamoyloxy, dimethylcarbamoyloxy, diethylcarbamoyloxy, methylethylcarbamoyloxy etc.) and the like.

Examples of the thiol group optionally having substituents, which is represented by $R^3$, include unsubstituted thiol group, lower alkylthio (e.g., $C_{1-4}$ alkylthio group such as methylthio, ethylthio, propylthio etc.), lower alkanoylthio (e.g., $C_{1-4}$ alkanoylthio such as acetylthio, propionylthio etc.) and the like.

Examples of the amino group optionally having substituents, which is represented by $R^3$, include unsubstituted amino group, lower alkylamino (e.g., $C_{1-4}$ alkylamino group such as methylamino, ethylamino, propylamino etc.), di-lower alkylamino (e.g., di-$C_{1-4}$ alkylamino such as dimethylamino, diethylamino etc.), $C_{1-4}$ alkanoylamino (e.g., acetamide, propionamide etc.), and the like.

Examples of the acyl group represented by $R^3$ include alkanoyl group (e.g., $C_{1-6}$ alkanoyl such as formyl, acetyl, propionyl etc.), alkylsulfonyl group (e.g., $C_{1-4}$ alkylsulfonyl such as methylsulfonyl, ethylsulfonyl etc.), carbamoyl group optionally having substituents (e.g., mono- or di-$C_{1-10}$ alkylcarbamoyl group such as methylcarbamoyl, ethylcarbamoyl, dimethylcarbamoyl, diethylcarbamoyl etc., mono- or di-$C_{6-14}$ arylcarbamoyl such as phenylcarbamoyl, diphenylcarbamoyl etc., mono- or di-$C_{7-16}$ aralkylcarbamoyl group such as benzylcarbamoyl, dibenzylcarbamoyl etc., and the like), sulfamoyl optionally having substituents (e.g., mono- or di-$C_{1-10}$ alkylsulfamoyl group such as methylsulfamoyl, ethylsulfamoyl, dimethylsulfamoyl, diethylsulfamoyl etc., mono- or di-$C_{6-14}$ arylsulfamoyl group such as phenylsulfamoyl, diphenylsulfamoyl etc., mono- or di-$C_{7-16}$ aralkylsulfamoyl group such as benzylsulfamoyl, dibenzylsulfamoyl etc., and the like), and the like.

Examples of the halogen atom represented by $R^3$ include fluorine, chlorine, bromine and iodine.

Examples of the protecting group represented by R include $C_{1-6}$ alkylcarbonyl (e.g., acetyl, propionyl etc.), phenylcarbonyl, $C_{1-6}$ alkyl-oxycarbonyl (e.g., methoxycarbonyl, ethoxycarbonyl etc.), phenyloxycarbonyl, $C_{7-10}$ aralkyloxycarbonyl (e.g., phenyl-$C_{1-4}$ alkyloxy-carbonyl such as benzyloxycarbonyl etc. and the like), trityl, phthaloyl and N,N-dimethylaminomethylene, each of which may be substituted, and formyl. Examples of the substituent include halogen atom (e.g., fluorine, chlorine, bromine, iodine etc.), formyl, $C_{1-6}$ alkyl-carbonyl (e.g., acetyl, propionyl, valeryl etc.), nitro group and the like, wherein the number of substituent is about 1 to 3.

Examples of the leaving group represented by X include halogen atom (chlorine atom, bromine atom, iodine atom etc.), alkyl or aryl-sulfonyloxy group (methanesulfonyloxy, ethanesulfonyloxy, benzenesulfonyloxy, p-toluenesulfonyloxy etc.), and the like.

The compound represented by the formula (I) of the present invention may form a salt. Examples of the salt include acid addition salt such as inorganic acid salt (e.g., hydrochloride, sulfate, hydrobromide, phosphate etc.), organic acid salt (e.g., acetate, trifluoroacetate, succinate, maleate, fumarate, propionate, citrate, tartrate, lactate, oxalate, methanesulfonate, p-toluenesulfonate etc.) and the like.

The compound represented by the formula (I) and a salt thereof may be a hydrate, and in the following, compound (I) also encompasses salts and hydrates.

The prodrug of Compound (I) means a compound which is converted to compound (I) having a steroid $C_{17,20}$-lyase inhibitory activity by in vivo reactions of enzymes, gastric acid and the like.

Examples of the prodrug of compound (I) include a compound obtained by substituting nitrogen atom of imidazole of compound (I) with acyl or alkyl (e.g., compound wherein the nitrogen atom has been substituted with dimethylaminosulfonyl, acetoxymethyl, (5-methyl-2-oxo-1,3-dioxolen-4-yl)methoxycarbonylmethyl, pivaloyloxymethyl, benzyloxymethyl etc.); a compound obtained by substituting hydroxy group of compound (I) with acyl, alkyl, phosphate, sulfate, borate, (e.g., compound (I) wherein the hydroxy group has been substituted with acetyl, palmitoyl, propanoyl, pivaloyl, succinyl, fumaryl, alanyl, dimethylaminomethylcarbonyl etc.); and the like. These compounds can be produced by a method known per se.

The prodrug of compound (I) may be as it is or a pharmaceutically acceptable salt. When the prodrug of compound (I) has an acidic group such as a carboxyl group, examples of the salt include a salt with an inorganic base (e.g., alkali metal such as sodium, potassium etc.; alkaline earth metal such as calcium, magnesium etc.; transition metal such as zinc, iron, copper etc., and the like); an organic base (e.g., organic amines such as trimethylamine, triethylamine, pyridine, picoline, ethanolamine, diethanolamine, triethanolamine, dicyclohexylamine, N,N'-dibenzylethylenediamine and the like, basic amino acids such as arginine, lysin, ornithine and the like) and the like.

When the prodrug of compound (I) has a basic group such as an amino group and the like, examples of the salt include salt with inorganic acid or organic acid (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.); acidic amino acids such as aspartic acid, glutamic acid etc.; and the like.

In addition, the prodrug of compound (I) may be a hydrate or a non-hydrate.

Compound (I) may have one or more asymmetric carbons in the molecule. The compound of the present invention also encompasses R-configuration and S-configuration at the asymmetric carbons.

Throughout the specification, of the compounds shown by the formulas (I), (I'), (II), (III), (III'), (IV), (IV'), (V), (VI), (VIII), (VIII') and (IX), a compound having a basic group or an acidic group can form a salt with an acid or a salt with a base, respectively. Examples of the salt with an acid and the salt with a base include those similar to the salts of the compound (I) mentioned above. Hereinafter the compounds represented by each formula and its salt are referred to as compound (symbol of formula). For example, a compound of formula (II) and a salt thereof are simply referred to as compound (II).

The compound (I) can be produced, for example, by the following method and the like.

The starting compound and synthetic intermediates can be used in a free form or as a salt thereof like compound (I), and they may be used for a reaction as a reaction mixture or after isolation by a known method.

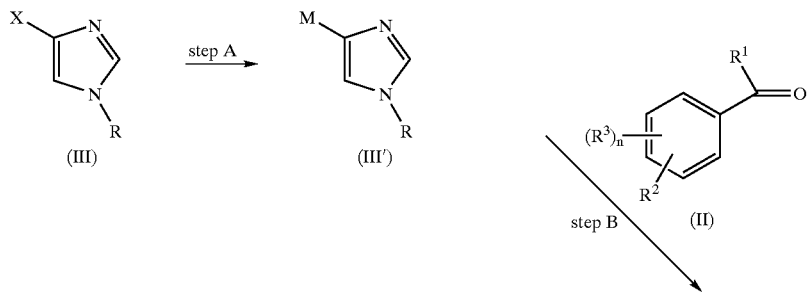

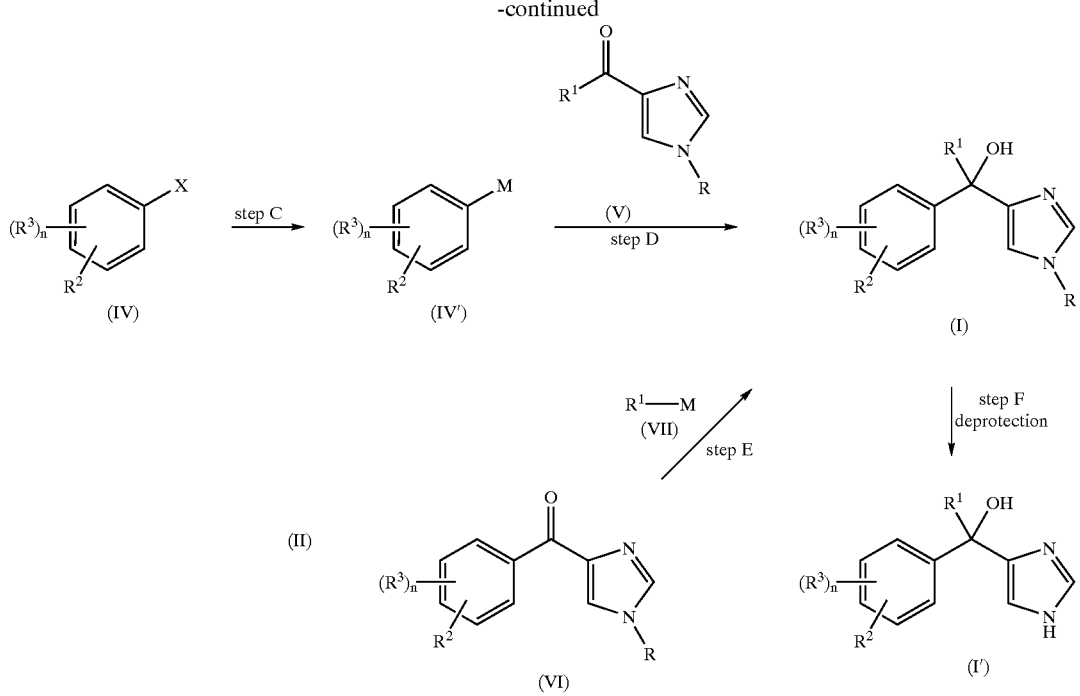

wherein M is a metal or a salt thereof, and the other symbols are as defined above.

Examples of the metal shown by M include lithium, magnesium and the like. Examples of a salt thereof include metal halide such as magnesium chloride, magnesium bromide, and the like.

[Steps A and B]

The compound (I) can be obtained by reacting compound (II) with an organic metal compound (III'). That is, compound (III) is reacted with alkyllithium, alkylmagnesium halide and the like to give an organic metal compound (III'), which is then reacted with compound (II) to give compound (I).

Examples of the alkyllithium used in the reaction include a $C_{1-4}$ alkyllithium such as n-butyllithium, s-butyllithium, tert-butyllithiumetc and the like. Alkyllithium is used in an amount of 1 to 3 moles, preferably 1 to 1.5 mole, per mole of the starting compound (III) or (IV). When alkyllithium is reacted, the reaction temperature is in the range of from −100° C. to 0° C., preferably −80° C. to −20° C. Examples of alkylmagnesium halide include ethylmagnesium bromide, methylmagnesium chloride and the like. The amount of alkylmagnesium halide to be used is 1 to 10 moles, preferably 1 to 4 moles, per mole of the starting compound (III). When compound (III) is reacted with alkyl magnesium halide, the reaction temperature is in the range of from −40° C. to 20° C., preferably −20° C. to 0° C. The reaction time is about 5 minutes to 20 hours. The reaction is usually carried out in an organic solvent that does not affect the reaction. Examples of the organic solvent which does not affect the reaction include ether such as diethyl ether, dioxane, tetrahydrofuran (THF) and the like, saturated hydrocarbon such as hexane, pentane and the like, halogenated hydrocarbon such as dichloromethane, chloroform and the like, aromatic hydrocarbon such as benzene, toluene and the like, and the like. These solvents may be used alone or in combination of two or more kinds thereof in an appropriate mixing ratio. The Compound (II) is used in 0.1 to 10 equivalents, preferably 0.2 to 2 equivalents, relative to Compound (III).

[Steps C and D]

The Compound (I) can be also obtained by reacting compound (IV) with a metal, such as an alkyllithium, magnesium and the like, to give an organic metal compound (IV'), which is then reacted with compound (V). Examples of alkyllithium used in the reaction include a $C_{1-4}$ alkyllithium such as nbutyllithium, s-butyllithium, t-butyllithium and the like. Alkyllithium is used in an amount of 1 to 3 moles, preferably 1 to 1.5 moles, per mole of starting compound (III) or (IV). When alkyllithium is reacted, the reaction temperature is in the range of from −100° C. to 0° C., preferably −80° C. to −20° C. When compound (IV) is reacted with magnesium metal, the amount of magnesium metal used is in the range of from 1 to 3 moles, preferably 1 to 1.5 moles, per mole of compound (IV), and the reaction temperature is in the range of from −20° C. to 100° C., preferably 10° C. to 50° C. The reaction time is about 5 minutes to 20 hours. The reaction is usually carried out in an organic solvent that does. not affect to the reaction. Examples of the organic solvent which does not affect to the reaction include ether such as diethyl ether, dioxane, tetrahydrofuran (THF) and the like, saturated hydrocarbon such as hexane, pentane and the like, halogenated hydrocarbon such as dichloromethane, chloroform and the like, aromatic hydrocarbon such as benzene, toluene and the like, and the like. These solvents may be used alone or in combination of two or more kinds thereof in an appropriate mixing ratio. The compound (V) is used in 0.1 to 10 equivalents, preferably 0.2 to 2 equivalents, relative to compound (IV).

[Step E]

The Compound (I) can be also obtained by reacting compound (VI) with an organic metal reagent (VII).

The amount of compound (VII) to be used is in the range of from 1 to 10 moles, preferably 1 to 5 moles, per mole of compound (VI), and the reaction temperature is in the range of from −80° C. to 60° C., preferably −80° C. to 50° C. The reaction time is about 5 minutes to 20 hours. The reaction is usually carried out in an organic solvent that does not affect the reaction. Examples of the solvent which does not affect the reaction include ether such as diethyl ether, dioxane, tetrahydrofuran (THF) and the like, saturated hydrocarbon such as hexane, pentane and the like, halogenated hydrocarbon such as dichloromethane, chloroform and the like, aromatic hydrocarbon such as benzene, toluene and the like, and the like. These solvents may be used alone or in combination of two or more kinds thereof in a suitable mixing ratio.

[Step F]

When R of compound (I) is a protecting group, the protecting group is eliminated by a method known per se or a method similar thereto to give compound (I'). For example, when R is a trityl group, the trityl group can be removed by a treatment under acidic conditions or hydrogenolysis. Examples of the acid include organic acid such as formic acid, acetic acid and the like, inorganic acid such as hydrochloric acid and the like, and the like. The reaction can be carried out in a solvent inert to the reaction, such as alcohol, ether (e.g., THF etc.) and the like. The reaction temperature is usually 0° C. to 100° C.

[Step I]

The compound (I) can be obtained by reacting compound (IX) with compound (X) in the presence of a palladium catalyst. The palladium catalyst to be used for the reaction is exemplified by nonvalent and divalent palladium complexes such as tetrakistriphenylphosphine palladium, 1,1'-bis(diphenylphosphino)ferrocene)dichloropalladium and the like. The reaction temperature is in the range of from 0° C. to 150° C., preferably from 50° C. to 120° C. The reaction time is about 1 hour to 48 hours. The reaction is usually carried out in a solvent that does not affect the reaction. Examples of the solvent that does not affect the reaction include ether such as dimethoxyethane, dioxane, tetrahydrofuran (THF) and the like, alcohol such as methanol, ethanol and the like, halogenated hydrocarbon such as dichloromethane, chloroform and the like, aromatic hydrocarbon such as benzene, toluene and the like, water and the like, which may be used alone or combination of one or two or more kinds of these at a suitable mixing ratio. When compound (X) is a boron compound, a base (sodium carbonate etc.) is preferably present in the reaction system.

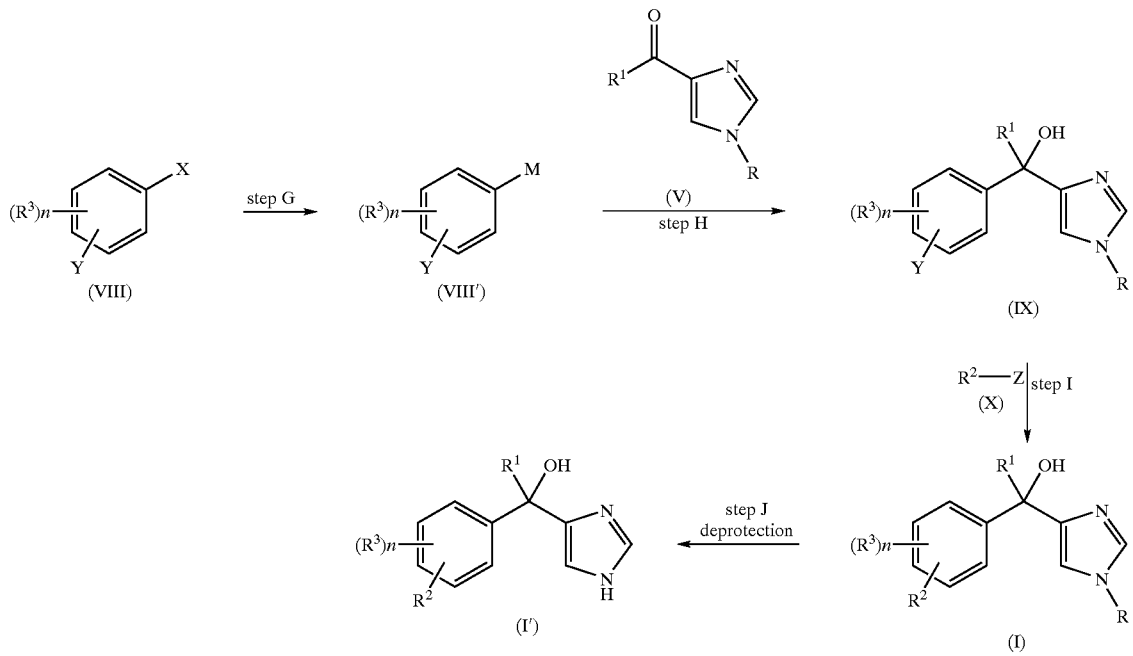

wherein Y is a leaving group (halogen atom, alkyl, arylsulfonyloxy group etc.) or a substituent capable of converting to a leaving group (e.g., protected hydroxyl group), Z is a leaving group such as trialkyltin, boric acid and the like, and other symbols are as defined above.

[Steps G and H]

In steps G and H, compound (VIII) is reacted with a metal, such as alkyllithium, magnesium etc., to give an organic metal compound (VIII'), which is reacted with compound (V) to give compound (IX). The reaction conditions are as above-mentioned with regard to Steps A and B. When Y of compound (VIII) is a protected hydroxyl group (e.g., trialkylsilyloxy group) that can be converted to a leaving group, the compound is converted to compound (IX), after which Y is preferably converted to a leaving group (e.g., trifluoromethanesulfonyloxy group). This conversion can be carried out according to a conventional method.

[Step J]

When R of compound (I) is a protecting group, the protecting group is eliminated by a method known per se or a method similar thereto to give compound (I'). For example, when R is a trityl group, it can be removed by a treatment under acidic conditions or by hydrogenolysis. Examples of the acid include organic acid such as formic acid, acetic acid and the like, inorganic acid such as hydrochloric acid and the like, and the like. A solvent inert to the reaction, such as alcohol, ether such as THF and the like, can be also used. The reaction temperature is generally from 0° C. to –100° C.

When the desired compound is obtained in a free form by the above reactions, the compound may be converted to a salt by a conventional method. When the desired compound is obtained as a salt, the compound can be converted to a free form or a different salt by a conventional method. Compounds (I) and (I') thus obtained can be isolated from the reaction mixture and purified by a known procedure such as phase transfer, concentration, solvent extraction, fractional distillation, crystallization, recrystallization, chromatography and the like.

In addition, a protecting group may be used for amino group, carboxyl group, hydroxy group and the like in the compound or a salt thereof to be reacted in the above reactions, which are not involved in the reaction. A protecting group may be added or eliminated by a known method.

Examples of the protecting group of amino group include $C_{1-6}$ alkylcarbonyl (e.g., acetyl, propionyl etc.), phenylcarbonyl, $C_{1-6}$ alkyl-oxycarbonyl (e.g., methoxycarbonyl, ethoxycarbonyl etc.), phenyloxycarbonyl, $C_{7-10}$ aralkyloxycarbonyl (e.g., phenyl-$C_{1-4}$ alkyloxy-carbonyl such as benzyloxycarbonyl etc., and the like), trityl, phthaloyl and N,N-dimethylaminomethylene and the like, each of which may be substituted, and formyl. Examples of the substituent include halogen atom (e.g., fluorine, chlorine, bromine, iodine etc.), formyl, $C_{1-6}$ alkyl-carbonyl (e.g., acetyl, propionyl, valeryl etc.), nitro group and the like. The number of substituent is about 1 to 3.

Examples of the protecting group of carboxyl group include, $C_{1-6}$ alkyl (e.g., methyl, ethyl, propyl, isopropyl, butyl, tert-butyl etc.), phenyl, trityl, silyl and the like, each of which may be substituted. Examples of the substituent include halogen atom (e.g., fluorine, chlorine etc.), formyl, $C_{1-6}$ alkyl-carbonyl (e.g., acetyl, propionyl, valeryl etc.), nitro group and the like. The number of substituent is about 1 to 3.

Examples of the protecting group of hydroxy group include $C_{1-6}$ alkyl (e.g., methyl, ethyl, propyl, isopropyl, butyl, tert-butyl etc.), phenyl, $C_{7-10}$ aralkyl (e.g., phenyl-$C_{1-4}$ alkyl such as benzyl etc., and the like), formyl, $C_{1-6}$ alkyl-carbonyl (e.g., acetyl, propionyl etc.), phenyloxycarbonyl, benzoyl, ($C_{7-10}$ aralkyloxy)carbonyl (e.g., phenyl-$C_{1-4}$ alkyloxy-carbonyl such as benzyloxycarbonyl etc., and the like), pyranyl, furanyl, silyl and the like, each of which may be substituted. Examples of the substituent include halogen atom (e.g., fluorine, chlorine etc.), $C_{1-6}$ alkyl (e.g., methyl, ethyl, propyl etc.), phenyl, $C_{7-10}$ aralkyl (e.g., phenyl-$C_{1-4}$ alkyl such as benzyl etc.), nitro group and the like. The number of substituent is about 1 to 4.

The protection group can be eliminated by a method known per se or a similar method. Examples of the method include treating using, for example, acid, base, reduction, ultraviolet light, hydrazine, phenylhydrazine, sodium N-methyldithiocarbamate, tetrabutylammonium fluoride, palladium acetate and the like.

The compound (I) has a superior effect as a medicine, and especially has a superior inhibitory activity against steroid $C_{17,20}$-lyase. The compound (I) is low toxic and causes few side effects. Therefore, compound (I) is useful as, for example, (i) an androgen or estrogen reducer, and (ii) an agent for the prophylaxis or treatment of various androgen- or estrogen-related diseases, such as (1) primary cancer, metastasis or recurrence of malignant tumor (e.g., prostate cancer, breast cancer, uterine cancer, ovarian cancer etc.), (2) various symptoms accompany these cancers (e.g., pain, cachexia etc.), (3) prostatic hypertrophy, virilism, hirsutism, male pattern alopecia, precocious puberty, endometriosis, uterus myoma, adenomyosis of uterus, mastopathy, polycystic ovary syndrome etc. in a mammal (e.g., human, bovine, horse, pig, dog, cat, monkey, mouse, rat etc., especially human).

While compound (I) has a superior effect even when used solely, the effect can be further promoted by using the compound in combination with other pharmaceutical preparations and therapies. Examples of the preparation and therapy to be combined include, but not limited to, sex hormones, alkylating agents, antimetabolites, antitumor antibiotics, plant alkaloids, immunotherapies and the like.

Examples of hormone-related agent include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (e.g., tamoxifen citrate, toremifene citrate etc.), contraceptive pill, mepitiostane, testolactone, aminoglutethimide, LH-RH agonists (e.g., goserelin acetate, buserelin, leuprorelin etc.), LH-RH antagonists (e.g., ganirelix, cetrorelix, abarelix etc.), droloxifene, epitiostanol, ethinylestradiol sulfonate, aromatase inhibitors (e.g., fadrozole, anastrozole, letrozole, exemestane, vorozole, formestane etc.), anti-androgens (e.g., flutamide, bicalutamide, nilutamide etc.), 5α-reductase inhibitors (e.g., finasteride, epristeride etc.), adrenocortical hormones (e.g., cortisol, dexamethasone, prednisolone, betamethasone, triamcinolone etc.), inhibitors of androgen-synthesis (e.g., abiraterone etc.), retinoid and suppressing agents of retinoid metabolism (e.g., liarozole etc.), and the like.

Examples of alkylating agents include nitrogen mustard, nitrogen mustard N-oxide hydrochloride, chlorambucil, cyclophosphamide, ifosfamide, thiotepa, carboquone, improsulphan tosilate, busulfan, nimustine hydrochloride, mitobronitol, melphalan, dacarbazine, ranimustine, estramustine phosphate sodium, triethylenemelamine, carmustine, lomustine, streptozocin, pipobroman, ethoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulfan, trofosfamide, zinostatin stimalamer, adozelesin, cystemustine, bizelesin, and the like.

Examples of antimetabolites include, for example, mercaptopurine, 6-mercaptopurine riboside, thioinosine, methotrexate, enocitabine, cytarabine, cytarabine ocfosfate, ancitabine hydrochloride, 5-FU analogues (e.g., fluorouracil, tegafur, UFT, doxifluridine, carmofur, galocitabine, emitefur etc.), aminopterin, leucovorin calcium, tabloid, butocin, calcium folinate, calcium levofolinate, cladribine, fludarabine, gemcitabine, hydroxycarbamide, pentostatin, piritrexim, idoxuridine, mitoguazone, tiazofurin and the like.

Example of antitumor antibiotics include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and the like.

Examples of plant alkaloid include etoposide, etoposide phosphate, vinblastine sulfate, vincristine sulfate, vindesine sulfate, teniposide, paclitaxel, vinorelbine, and the like.

Examples of immunotherapeutic agent (BRM) include picibanil, krestin, sizofiran, lentinan, ubenimex, interferons, interleukins, macrophage-colony stimulating factor, granulocyte-colony stimulating factor, erythropoietin, lymphotoxin,-BCG vaccine, corynebacterium parvum, levamisole, polysaccharide-K, procodazol, and the like.

In addition, L-asparaginase, aceglatone, procarbazine hydrochloride, cobalt-protoporphyrin complex, mercury-hematoporphyrin sodium salt, topoisomerase I inhibitors (e.g., irinotecan, topotecan etc.), topoisomerase II inhibitors (e.g., sobuzoxane etc.), differentiation promoter (e.g., retinoid, vitamin D etc.), inhibitor of proliferation factor (e.g., suramin etc.), antibodies (e.g., herceptin etc.), angiogenesis inhibitors, α-blocker (e.g., tamsulosin hydrochloride etc.), tyrosin kinase inhibitors, and the like can be used.

Together with the chemotherapy including administration of compound (I), therapies other than chemotherapies, such as an operation including orchidectomy, thermotherapy, radiotherapy and the like can be conducted.

Particularly, the compound of the present invention can remove androgens or estrogens in blood more effectively by combinedly using a LH-RH modulator such as LH-RH agonist (e.g., goserelin acetate, buserelin, leuprorelin etc.) and LHRH antagonist (e.g., ganirelix, cetrorelix, abarelix etc.).

Thus, the compound of the present invention has high selectivity to steroid $C_{17,20}$-lyase, and reduces androgen concentration without affecting drug metabolizing enzyme such as CYP3A4 and the like.

Examples of the pharmaceutically acceptable carrier include various organic or inorganic carriers conventionally used as materials for pharmaceuticals, which are added as appropriate in suitable amounts as exipients, lubricants, binders, disintegrators, thickeners for solid preparations; solvents, dispersants, solbilizing agents, suspending agents, isotonic agents, buffer agents, soothing agents for liquid preparations, and the like. Where necessary, additives such as preservatives, antioxidants, coloring agents, sweetening agents etc. can be used. Examples of preferable exipient include lactose, saccharose, D-mannitol, starch, crystalline cellulose, light anhydrous silicic acid and the like. Examples of preferable lubricant include magnesium stearate, calcium stearate, talc, colloidal silica, and the like. Examples of preferable binder include crystalline cellulose, saccharose, D-mannitol, dextrin, hydroxypropylcellulose, hydroxypropylmethylcellulose, polyvinyl pyrrolidone, and the like. Examples of preferable disintegrator include starch, carboxymethylcellulose, calcium carboxymethylcellulose, sodium crosscarmelose, sodium carboxymethyl starch, and the like. Examples of preferable thickener include natural rubbers, cellulose derivatives, acrylate polymers, and the like. Examples of preferable solvent include water for injection, alcohol, propyleneglycol, Macrogol, sesame oil, corn oil, and the like. Examples of preferable dispersant include Tween 80, HCO 60, polyethylene glycol, carboxymethylcellulose, sodium alginate, and the like. Examples of preferable solbilizing agent include polyethylene glycol, propylene glycol, D-mannitol, benzyl benzoate, ethanol, trisaminomethane, cholesterol, triethanolamine, sodium carbonate, sodium citrate, and the like. Examples of preferable suspending agent include surfactants, such as stearyl triethanolamine, sodium laurylsulfate, laurylaminopropionic acid, lecithin, benzalkonium chloride, benzethonium chloride, glycerin monostearate etc.; hydrophilic polymer such as polyvinyl alcohol, polyvinyl pyrrolidone, sodium carboxymethyl cellulose, methylcellulose, hydroxymethylcellulose, hydroxyethylcellulose, hydroxypropylcellulose etc.; and the like. Examples of preferable isotonic agent include sodium chloride, glycerin, D-mannitol and the like.

Examples of preferable buffer agent include buffer solution such as phosphate, acetate, carbonate, citrate etc., and the like. Examples of preferable soothing agent include benzyl alcohol, and the like. Examples of preferable preservative include paraoxybenzoates, chlorobutanol, benzyl alcohol, phenethyl alcohol, dehydroacetic acid, sorbic acid, and the like. Examples of preferable antioxidant include sulfurous acid salt, ascorbic acid, and the like.

The pharmaceutical composition and pharmaceutical preparation of the present invention can be manufactured by a conventional method. The ratio of compound (I) contained in a pharmaceutical preparation is usually 0.1 to 100% (w/w). Specific examples are shown below.

(1) Tablets, Powder, Granules, Capsules

These can be produced by adding, for example, exipients, disintegrators, binders, lubricants etc. to compound (I), compression forming the mixture and, where necessary, coating for masking of taste, enteric or sustained release.

(2) Injection

This can be produced by preparing compound (I) into an aqueous injection together with, for example, dispersants, preservatives, isotonic agents etc., or into an oily injection by dissolving, suspending or emulsifying the compound in a vegetable oil such as olive oil, sesame oil, cotton seed oil, corn oil etc., or propylene glycol etc.

(3) Suppository

This can be produced by preparing compound (I) into an oily or aqueous solid, semisolid or liquid composition. Examples of oily base used for the composition include glyceride of higher fatty acid (e.g., cacao butter, witepsols etc.), middle fatty acid (e.g., migriols etc.), vegetable oils (e.g., sesame oil, soybean oil, cotton seed oil etc.) and the like. Examples of aqueous gel base include natural rubber, cellulose derivative, vinyl polymer, acrylate polymer, and the like.

The content of compound (I) admixed in these preparations is usually 0.01 to 50%, though subject to change depending upon the kind of preparations.

While the amount of compound (I) to be contained in the above-mentioned pharmaceutical preparation varies depending upon the compound selected, the kind of animal to be the administration target, administration frequency and the like, the compound proves effective over a broad range. The daily dose of the pharmaceutical preparation of the present invention as an effective amount of compound (I) of the present invention, for example, for in the case of oral administration to an adult patient with a solid tumor (e.g., patient with prostate cancer) is generally about 0.001 to about 500 mg/kg body weight, preferably about 0.05 to about 40 mg/kg body weight, more preferably about 0.1 to about 10 mg/kg body weight. When the compound is parenterally administered or administered concurrently with a different anticancer agent, the dose generally becomes less than those mentioned above. The amount of the compound actually administered is determined according to the selection of compound, dosage form of each preparation, age, body weight and sex of patient, degree of disease, administration route, period and intervals of administration and the like, which can be varied according to the judgement of a doctor.

The administration route of the aforementioned pharmaceutical preparation is free of any particular limitaion by various conditions. The preparation can be administered, for example, orally or parenterally. Examples of the "parenteral" used here include intravenous, intramuscular, subcutaneous, intranasal, intradermal, instillation, intracerebral, intrarectal, intravaginal and intraperitoneal administrations, and the like.

The above-mentioned administration term and administration interval vary depending upon various conditions and determined any time by judgement of a doctor. Divided administration, consecutive administration, intermittent administration, high dose short period administration, repeat administration and the like can be employed. For oral administration, for example, the dose is desirably given once a day or divided into several portions (especially two or three doses a day) and administered. Administration of a sustained release preparation or intravenous drip infusion over a long time is also possible.

DESCRIPTION OF THE PREFERRED EMBODIMENT

The present invention is described in more detail by means of the following Examples, Formulation Example and Experimental Examples. These Examples are mere practice of the invention and do not limit the present invention. They can be modified as long as they do not deviate from the scope of the present invention. In the Examples, abbreviations mean the following.

s: singlet, d: doublet, t: triplet, q: quartet, dd: double doublet, dt: double triplet, m: multiplet, br: broad, J: coupling constant, room temperature: 0–30° C., DMF: dimethylformamide, THF: tetrahydrofuran.

EXAMPLES

Reference Example 1

Production of 4-[1-hydroxy-2-methyl-1-(1-trityl-1H-imidazol-4-yl)propyl]phenylboronic acid To a solution of p-dibromobenzene (66.0 g) in THF (700 ml) was added dropwise a solution (1.6 M; 180 ml) of n-butyllithium in hexane at —78° C., and the mixture was stirred at the same temperature for 15 min. A solution of 2-methyl-1-(1-trityl-1H-imidazol-4-yl)-1-propanone (85.0 g) in THF (250 ml) was added dropwise, and the mixture was further stirred for 15 min. To the reaction mixture was added dropwise a solution (1.6 M; 270 ml) of n-butyllithium in hexane at −78° C., and the mixture was stirred at the same temperature for 15 min, which was followed by addition of trimethyl borate (196 ml). The reaction mixture was stirred at room temperature for 2 h, and an aqueous ammonium chloride solution was added. The mixture was stirred at room temperature for 12 h, and the organic layer was separated, washed with 1N sodium hydroxide and brine and dried over anhydrous magnesium sulfate. The solvent was evaporated to give a crude product (126 g) of the title compound as an amorphous powder. This product was used in a reaction without purification.

Example 1

Production of 1-(1H-imidazol-4-yl)-1-(4'-methoxy-[1,1'-biphenyl]-4-yl)-2-methyl-1-propanol (i) Production of 4-bromo-4'-methoxy-1,1'-biphenyl Under an argon atmosphere, p-dibromobenzene (9.99 g), 4-methoxyphenylboronic acid (2.03 g) and tetrakistriphenylphosphine palladium (497 mg) were dissolved in dimethoxyethane (20 ml). A 2M aqueous sodium carbonate solution (20 ml) was added and the mixture was heated under reflux for 14 h. The reaction mixture was cooled to room temperature and the precipitated crystals were collected by filtration. The obtained crystals were dissolved in ethyl acetate and insoluble materials were filtered off. The solvent was evaporated and the obtained solid was washed with hexane to give the title compound (2.09 g) as a colorless solid.

$^1$H-NMR (CDCl$_3$) δ: 3.84 (3H, s), 6.97 (2H, d, J=8.8 Hz), 7.37–7.56 (6H, m).

IR (KBr): 1483, 1291, 1258, 1038, 812 cm$^{-1}$.

(ii) Production of 1-(1H-imidazol-4-yl)-1-(4'-methoxy-[1,1'-biphenyl]-4-yl)-2-methyl-1-propanol 4-Bromo-4'-methoxy-1,1'-biphenyl (1.95 g) was dissolved in THF (40 ml) and the mixture was cooled to −78° C. A solution (1.6 M; 5.5 ml) of n-butyllithium in hexane was added dropwise, and the mixture was stirred at −78° C. for 1 h. Then, a solution (10 ml) of 1-(1H-imidazol-4-yl)-2-methyl-1-propanone (335 mg) in THF was slowly added dropwise. The reaction mixture was heated from −78° C. to room temperature and saturated aqueous ammonium chloride solution was added to the reaction mixture. The mixture was extracted with ethyl acetate and the organic layer was dried and concentrated. The obtained residue was recrystallized from ethyl acetate to give the title compound (322 mg) as a colorless solid.

$^1$H-NMR (CDCl$_3$+CD$_3$OD) δ: 0.83 (3H, d, J=6.6 Hz), 0.98 (3H, d, J=6.6 Hz), 2.52–2.76 (1H, m), 3.85 (3H, s), 6.92–7.02 (3H, m), 7.38–7.62 (7H, m).

IR (KBr): 3218, 1497; 1252, 1038, 1007, 816 cm$^{-1}$.

Example 2

Production of 1-[1,1'-biphenyl]-4-yl-1-(1H-imidazol-4-yl)-2-methyl-1-propanol

By the reaction in the same manner as in Example 1-(ii) using 4-bromo-1,1'-biphenyl (5.17 g), the title compound (1.76 g) was obtained as a colorless solid.

$^1$H-NMR (CDCl$_3$+CD$_3$OD) δ: 0.83 (3H, d, J=6.8 Hz), 0.99 (3H, d, J=6.8 Hz), 2.57–2.74 (1H, m), 6.98 (1H, d, J=1.2 Hz), 7.30–7.47 (3H, m), 7.50–7.65 (7H, m).

IR (KBr): 3142, 2965, 1487, 826, 762 cm$^{-1}$.

Example 3

Production of 1-(1H-imidazol-4-yl)-1-(2'-methoxy[1,1'-biphenyl]-4-yl)-2-methyl-1-propanol (i) Production of 4-bromo-2'-methoxy-1,1'-biphenyl By the reaction in the same manner as in Example 1-(i) using 2-methoxyphenylboronic acid (3.15 g), the title compound (4.77 g) was obtained as a colorless solid.

$^1$H-NMR (CDCl$_3$) δ: 3.81 (3H, s), 6.92–7.08 (2H, m), 7.21–7.44 (4H, m), 7.45–7.60 (2H, m).

IR (KBr): 1478, 1256, 1003, 754 cm$^{-1}$.

(ii) Production of 1-(1H-imidazol-4-yl)-1-(2'-methoxy[1,1'-biphenyl]-4-yl)-2-methyl-1-propanol By the reaction in the same manner as in Example 1-(ii) using 4-bromo-2'-methoxy-1,1'-biphenyl (1.58 g), the title compound (225 mg) was obtained as a colorless solid.

$^1$H-NMR (CDCl$_3$) δ: 0.85 (3H, d, J=7.0 Hz), 0.98 (3H, d, J=7.0 Hz), 2.52–2.72 (1H, m), 3.79 (3H, s), 6.92–7.06 (3H, m), 7.26–7.36 (2H, m), 7.42–7.62 (5H, m).

IR (KBr): 3073, 2967, 1487, 1260, 1238, 1005, 752 cm$^{-1}$.

Example 4

Production of 1-(4'-fluoro[1,1'-biphenyl]-4-yl)-1-(1H-imidazol-4-yl)-2-methyl-1-propanol (i) Production of 1-(4-bromophenyl)-(1-trityl-1H-imidazol-4-yl)-2-methyl-1-propanol To a solution of p-dibromobenzene (20.0 g) in diethyl ether-THF (4:1) (210 ml) was slowly added dropwise at −78° C. a solution (1.6 M; 34.6 ml) of n-butyllithium in hexane. The mixture was stirred at −78° C. for 40 min and at −78 to −30° C. for 15 min. A solution of 2-methyl-1-(1-trityl-1H-imidazol-4-yl)-1-propane (14.0 g) in THF (80 ml) was slowly added dropwise, and the mixture was stirred at −78 to −50° C. for 40 min. To the reaction mixture was added saturated aqueous ammonium chloride solution, and the mixture was extracted with ethyl acetate, the organic layer was washed with saturated brine and dried. The solvent was evaporated under reduced pressure and the residue was recrystallized from ethyl acetate-hexane to give the title compound (16.2 g) as colorless needle crystals.

$^1$H-NMR (CDCl$_3$) δ: 0.71 (3H, d, J=6.6 Hz), 0.89 (3H, d, J=6.6 Hz), 2.30–2.44 (1H, m), 3.50 (1H, s), 6.72 (1H, d, J=1.2 Hz), 7.09–7.16 (6H, m), 7.30–7.38 (14H, m)

IR (KBr): 1489, 1445, 1159, 1009, 909, 812, 747, 735, 702, 660 cm$^{-1}$ (ii) Production of 1-(4'-fluoro[1,1'-biphenyl]-4-yl)-1-(1-trityl-1H-imidazol-4-yl)-2-methyl-1-propanol To a suspension of 1-(4-bromophenyl)-(1-trityl-1H-imidazol-4-yl)-2-methyl-1-propanol (3.60 g), 4-fluorophenylboronic acid (1.50 g) and 2M aqueous sodium carbonate solution (26.8 ml) in dimethoxyethane (50 ml) was added tetrakis(triphenylphosphine)palladium(0) (387 mg). Under an argon atmosphere, the mixture was heated under reflux for 12 h. The reaction mixture was extracted with ethyl acetate-THF (8:3), washed with water and saturated brine, and dried. The solvent was evaporated under reduced pressure, and the residue was purified by silica gel column chomatography (eluent, hexane:ethyl acetate=6:1→4:1) to give the title compound (3.16 g) as colorless needle crystals.

$^1$H-NMR (CDCl$_3$) δ: 0.77 (3H, d, J=6.6 Hz), 0.92 (3H, d, J=6.6 Hz), 2.42–2.49 (1H, m), 3.53 (1H, s), 6.78 (1H, s), 7.06–7.15 (7H, m), 7.33–7.57 (17H, m)

IR (KBr): 1493, 1445, 1223, 1159, 818, 748, 733, 702 cm$^{-1}$ (iii) Production of 1-(4'-fluoro[1,1'-biphenyl]-4-yl)-1-(1H-imidazol-4-yl)-2-methyl-1-propanol A solution (75 ml) of 1-(4'-fluoro[1,1'-biphenyl]-4-yl)-1-(1-trityl-1H-imidazol-4-yl)-2-methyl-1-propanol (3.12 g) and pyridine hydrochloride (1.11 g) in methanol was stirred at 60° C. for 3.5 h. The solvent was evaporated from the reaction mixture under reduced pressure and the residue was diluted with ethyl acetate. Saturated aqueous sodium hydrogen carbonate was added, and the mixture was extracted with ethyl acetate. The organic layer was washed with saturated brine and dried. The solvent was evaporated under reduced pressure and the residue was purified by column chomatography (eluent, hexane:ethyl acetate=2:1→1:5) and recrystallized from ethyl acetate-hexane to give the title compound (1.34 g) as colorless needle crystals.

$^1$H-NMR (CDCl$_3$) δ: 0.85 (3H, d, J=7.0 Hz), 1.00 (3H, d, J=7.0 Hz), 2.60–2.74 (1H, m), 3.42 (1H, br s), 7.02–7.16 (3H, m), 7.48–7.66 (7H, m), 9.16 (1H, br s)

IR (KBr): 3241, 1493, 1397, 1242, 1009, 814, 781, 762, 623, 511 cm$^{-1}$

Example 5

Production of 1-(4'-chloro[1,1'-biphenyl]-4-yl)-1-(1H-imidazol-4-yl)-2-methyl-1-propanol (i) Production of 1-(4'-chloro[1,1'-biphenyl]-4-yl)-1-(1-trityl-1H-imidazol-4-yl)-2-methyl-1-propanol By the reaction in the same manner as in Example 4-(ii) using 1-(4-bromophenyl)-(1-trityl-1H-imidazol-4-yl)-2-methyl-1-propanol (3.60 g), 4-chlorophenylboronic acid (1.68 g), 2M aqueous sodium carbonate solution (26.8 ml) and tetrakis(triphenylphosphine)palladium(0) (387 mg), the title compound (3.04 g) was obtained as colorless needle crystals.

$^1$H-NMR (CDCl$_3$) δ: 0.76 (3H, d, J=7.0 Hz), 0.92 (3H, d, J=7.0 Hz), 2.42–2.49 (1H, m), 3.53 (1H, s), 6.78 (1H, s), 7.13–7.15 (6H, m), 7.32–7.59 (18H, m)

IR (KBr): 1485, 1445, 1094, 1005, 909, 812, 747, 733, 700 cm$^{-1}$ (ii) Production of 1-(4'-chloro[1,1'-biphenyl]-4-yl)-1-(1H-imidazol-4-yl)-2-methyl-1-propanol By the reaction in the same manner as in Example 4-(iii) using 1-(4'-chloro[1,1'-biphenyl]-4-yl)-1-(1-trityl-1H-imidazol-4-yl)-2-methyl-1-propanol (3.00 g) and pyridine hydrochloride (1.04 g), the title compound (1.18 g) was obtained as colorless plate crystals.

$^1$H-NMR (CDCl$_3$) δ: 0.83 (3H, d, J=7.0 Hz), 0.98 (3H, d, J=7.0 Hz), 2.58–2.75 (1H, m), 3.38 (1H, br s), 7.00 (1H, s), 7.37 (2H, d, J=8.4 Hz), 7.48–7.64 (7H, m), 9.24 (1H, br s)

IR (KBr): 3200, 1485, 1364, 1190, 1094, 1028, 1005, 808, 781 cm$^{-1}$

Example 6

Production of 1-[1,1'-biphenyl]-3-yl-1-(1H-imidazol-4-yl)-2-methyl-1-propanol

By the reaction in the same manner as in Example 1-(ii) using 3-bromo-1,1'-biphenyl (0.98 g), the title compound (0.25 g) was obtained as a colorless solid.

$^1$H-NMR (CDCl$_3$+CD$_3$OD) δ: 0.83 (3H, d, J=6.6 Hz), 0.99 (3H, d, J=6.6 Hz), 2.55–2.73 (1H, m), 6.97 (1H, d, J=1.0 Hz), 7.28–7.50 (7H, m), 7.54–7.62 (2H, m), 7.72–7.77 (1H, m).

IR (KBr): 3200, 1005, 799 cm$^{-1}$.

Example 7

Production of 1-(1H-imidazol-4-yl)-1-(2'-methoxy[1,1'-biphenyl]-3-yl)-2-methyl-1-propanol (i) Production of 3-bromo-2'-methoxy-1,1'-biphenyl By the reaction in the same manner as in Example 1-(i) using 2-methoxyphenylboronic acid (2.90 g), the title compound (4.38 g) was obtained as a colorless oil.

$^1$H-NMR (CDCl$_3$) δ: 3.81 (3H, s), 6.97 (1H, d, J=8.2 Hz), 7.02 (1H, dt, J=1.0, 7.4 Hz), 7.21–7.49 (5H, m), 7.68 (1H, t, J=1.8 Hz).

IR (KBr): 1466, 1254, 1235, 1028 cm$^{-1}$.

(ii) Production of 1-(1H-imidazol-4-yl)-1-(2'-methoxy[1,1'-biphenyl]-3-yl)-2-methyl-1-propanol By the reaction in the same manner as in Example 1-(ii) using 3-bromo-2'-methoxy-1,1'-biphenyl (2.10 g), the title compound (0.44 g) was obtained as a colorless solid.

$^1$H-NMR (CDCl$_3$+CD$_3$OD) δ: 0.85 (3H, d, J=6.8 Hz), 0.99 (3H, d, J=6.8 Hz), 2.40–2.80 (1H, m), 3.77 (3H, s), 6.93–7.07 (3H, m), 7.25–7.49 (6H, m), 7.63 (1H, s).

IR (KBr): 2961, 1473, 1236, 1024 cm$^{-1}$.

Example 8

Production of 1-(1H-imidazol-4-yl)-1-(3'-methoxy[1,1'-biphenyl]-3-yl)-2-methyl-1-propanol (i) Production of 3-bromo-3'-methoxy-1,1'-biphenyl By the reaction in the same manner as in Example 1-(i) using 3-methoxyphenylboronic acid (3.04 g), the title compound (3.10 g) was obtained as a colorless oil.

¹H-NMR (CDCl₃) δ: 3.85 (3H, s), 6.86–6.96 (1H, m), 7.04–7.17 (2H, m), 7.23–7.54 (4H, m), 7.70–7.75 (1H, m).
IR (KBr): 1591, 1559, 1470, 1213 cm⁻¹.

(ii) Production of 1-(1H-imidazol-4-yl)-1-(3'-methoxy[1,1'-biphenyl]-3-yl)-2-methyl-1-propanol By the reaction in the same manner as in Example 1-(ii) using 3-bromo-3'-methoxy-1,1'-biphenyl (2.09 g), the title compound (0.24 g) was obtained as a colorless solid.
¹H-NMR (CDCl₃) δ: 0.83 (3H, d, J=6.7 Hz), 0.98 (3H, d, J=6.7 Hz), 2.58–2.78 (1H, m), 3.86 (3H, s), 6.88 (1H, d, J=8.4 Hz), 7.00 (1H, s), 7.08–7.24 (2H, m), 7.24–7.60 (6H, m), 7.79 (1H, s).
IR (KBr): 3202, 1472, 1044, 1005 cm⁻¹.

Example 9

Production of 1-(1H-imidazol-4-yl)-1-(4'-methoxy[1,1'-biphenyl]-3-yl)-2-methyl-1-propanol (i) Production of 3-bromo-4'-methoxy-1,1'-biphenyl By the reaction in the same manner as in Example 1-(i) using 4-methoxyphenylboronic acid (3.08 g), the title compound (3.84 g) was obtained as colorless needle crystals.
¹H-NMR (CDCl₃) δ: 3.85 (3H, s), 6.92–7.02 (2H, m), 7.22–7.32 (1H, m), 7.38–7.54 (4H, m), 7.69 (1H, t, J=1.9 Hz).
IR (KBr): 1520, 1474, 1252, 837 cm⁻¹.

(ii) Production of 1-(1H-imidazol-4-yl)-1-(4'-methoxy[1,1'-biphenyl]-3-yl)-2-methyl-1-propanol By the reaction in the same manner as in Example 1-(ii) using 3-bromo-4'-methoxy-1,1'-biphenyl (2.01 g), the title compound (0.50 g) was obtained as a colorless solid.
¹H-NMR (CDCl₃) δ: 0.82 (3H, d, J=6.9 Hz), 0.98 (3H, d, J=6.9 Hz), 2.50–2.74 (1H, m), 3.83 (3H, s), 6.89–6.99 (3H, m), 7.26–7.55 (6H, m), 7.71–7.76 (1H, m).
IR (KBr): 2969, 1516, 1480, 1248, 1181 cm⁻¹.

Example 10

Production of 1-(1H-imidazol-4-yl)-1-(4-methoxy[1,1'-biphenyl]-3-yl)-2-methyl-1-propanol (i) Production of 4-methoxy[1,1'-biphenyl]-3-carbaldehyde By the reaction in the same manner as in Example 1-(i) using 5-bromo-o-anisaldehyde (8.00 g), the title compound (3.75 g) was obtained as a colorless solid.
¹H-NMR (CDCl₃) δ: 3.98 (3H, s), 7.08 (1H, d, J=8.8 Hz), 7.28–7.48 (3H, m), 7.49–7.63 (2H, m), 7.80 (1H, dd, J=2.5, 8.8 Hz), 8.08 (1H, d, J=2.5 Hz), 10.52 (1H, s).
IR (KBr): 1680, 1609, 1483, 1271 cm⁻¹.

(ii) Production of 1H-imidazol-4-yl(4-methoxy[1,1'-biphenyl]-3-yl)methanol

4-Bromo-1H-imidazole (5.20 g) was dissolved in THF (50 ml) and the mixture was cooled to −78° C. A solution (1.7 M; 50 ml) of t-butyllithium in pentane was added. The mixture was stirred at 0° C. for 1.5 h and cooled to −78° C. again. A solution (30 ml) of 4-methoxy[1,1'-biphenyl]-3-carbaldehyde (2.54 g) in THF was added, and the mixture was heated from −78° C. to room temperature and further stirred at room temperature for 24 h. Aqueous ammonium chloride solution was added, and the mixture was extracted with ethyl acetate. The organic layer was dried and concentrated. The residue was purified by silica gel column chomatography (eluent, dichloromethane:methanol=15:1) and recrystallized from ethyl acetate to give the title compound (1.15 g) as a colorless solid.
¹H-NMR (CDCl₃) δ: 3.84 (3H, s), 6.15 (1H, s), 6.70 (1H, s), 6.96 (1H, d, J=8.4 Hz), 7.23–7.44 (3H, m), 7.46–7.57 (4H, m), 7.69 (1H, d, J=2.2 Hz).
IR (KBr): 3134, 1481, 1242, 1030 cm⁻¹.

(iii) Production of (1H-imidazol-4-yl)(4-methoxy[1,1'-biphenyl]-3-yl)methanone

1H-Imidazol-4-yl(4-methoxy[1,1'-biphenyl]-3-yl)methanol (0.94 g) was dissolved in dichloromethane (100 ml) and manganese dioxide (5.52 g) was added. The mixture was stirred at room temperature for 14 h, filtrated and concentrated. To the obtained residue was added ethyl acetate and the mixture was crystallized to give the title compound (0.84 g) as a colorless solid.
¹H-NMR (CDCl₃+CD₃OD) δ: 3.87 (3H, s), 7.11 (1H, d, J=8.4 Hz), 7.28–7.49 (3H, m), 7.51–7.60 (3H, m), 7.67–7.76 (2H, m), 7.83 (1H, m).
IR (KBr): 3000, 1636, 1483, 1273 cm⁻¹.

(vi) Production of 1-(1H-imidazol-4-yl)-1-(4-methoxy[1,1'-biphenyl]-3-yl)-2-methyl-1-propanol 1H-Imidazol-4-yl(4-methoxy[1,1'-biphenyl]-3-yl)methanone (0.62 g) was dissolved in THF (15 ml) and the mixture was cooled to −40° C. A solution (0.6 M; 15 ml) of isopropyl magnesium chloride in THF was slowly added dropwise and the mixture was warmed to room temperature. The mixture was stirred for 1 h and thereto was added saturated aqueous ammonium chloride solution. The mixture was diluted with water and extracted with ethyl acetate. The extract was dried and concentrated. The obtained residue was purified by silica gel column chomatography (eluent, dichloromethane:methanol=40:1) to give the colorless amorphous title compound (0.16 g).
¹H-NMR (CDCl₃) δ: 0.92 (3H, d, J=6.6 Hz), 0.95 (3H, d, J=6.6 Hz), 2.70–2.95 (1H, m), 3.90 (3H, s), 6.97 (1H, d, J=8.6 Hz), 7.06 (1H, s), 7.24–7.56 (7H, m), 7.73 (1H, d, J=1.8 Hz).
IR (KBr): 2967, 1481, 1242, 1024 cm⁻¹.

Example 11

Production of 1-(1H-imidazol-4-yl)-1-(6-methoxy[1,1'-biphenyl]-3-yl)-2-methyl-1-propanol (i) Production of 6-methoxy[1,1'-biphenyl]-3-carbaldehyde By the reaction in the same manner as in Example 1-(i) using 3-bromo-p-anisaldehyde (7.98 g), the title compound (7.78 g) was obtained as a colorless oil.
¹H-NMR (CDCl₃) δ: 3.90 (3H, s), 7.09 (1H, d, J=9.2 Hz), 7.30–7.56 (5H, m), 7.85 (1H, s), 7.87 (1H, dd, J=2.2, 7.8 Hz), 9.93 (1H, s).
IR (KBr): 1694, 1595, 1265, 1175 cm⁻¹.

(ii) Production of (1H-imidazol-4-yl)(6-methoxy[1,1'-biphenyl]-3-yl)methanol

By the reaction in the same manner as in Example 10-(ii) using 6-methoxy[1,1'-biphenyl]-3-carbaldehyde (3.10 g), the title compound (3.84 g) was obtained as a colorless solid.

$^1$H-NMR (CDCl$_3$+CD$_3$OD) δ: 3.81 (3H, s), 5.81 (1H, s), 6.73 (1H, s), 6.97 (1H, d, J=8.8 Hz), 7.24–7.46 (5H, m), 7.46–7.58 (2H, m), 7.59 (1H, d, J=1.0 Hz).

IR (KBr): 2996, 1487, 1175, 1022, 986 cm$^{-1}$.

(iii) Production of (1H-imidazol-4-yl)(6-methoxy[1,1'-biphenyl]-3-yl)methanol

By the reaction in the same manner as in Example 10-(iii) using (1H-imidazol-4-yl) (6-methoxy[1,1'-biphenyl]-3-yl) methanol (3.74 g), the title compound (2.64 g) was obtained as a colorless solid.

$^1$H-NMR (CDCl$_3$+CD$_3$OD) δ: 3.92 (3H, s), 7.10 (1H, d, J=8.8 Hz), 7.35–7.60 (5H, m), 7.73 (1H, s), 7.83 (1H, s), 7.90–8.10 (2H, brs).

IR (KBr): 3004, 1644, 1343, 1264 cm$^{-1}$.

(vi) Production of 1-(1H-imidazol-4-yl)-1-(6-methoxy[1,1'-biphenyl]-3-yl)-2-methyl-1-propanol By the reaction in the same manner as in Example 10-(iv) using (1H-imidazol-4-yl)(6-methoxy[1,1'-biphenyl]-3-yl) methanome (1.10 g), the title compound (0.48 g) was obtained as a colorless solid.

$^1$H-NMR (CDCl$_3$) δ: 0.84 (3H, d, J=6.8 Hz), 0.96 (3H, d, J=6.8 Hz), 2.45–2.70 (1H, m), 3.77 (3H, s), 6.86–6.96 (2H, m), 7.26–7.56 (8H, m).

IR (KBr): 2969, 1505, 1487, 1264 cm$^{-1}$.

Example 12

Production of 1-(4'-chloro[1,1'-biphenyl]-3-yl)-1-(1H-imidazol-4-yl)-2-methyl-1-propanol (i) Production of 1-(3-bromophenyl)-2-methyl-1-(1-trityl-1H-imidazol-4-yl)-1-propanol By the reaction in the same manner as in Example 1-(ii) using 1-(1-trityl-1H-imidazol-4-yl)-2-methyl-1-propanone (34.90 g) and O-dibromobenzene (50.7 g), the title compound (37.7 g) was obtained as a colorless solid.

$^1$H-NMR (CDCl$_3$) δ: 0.72 (3H, d, J=6.8 Hz), 0.90 (3H, d, J=6.8 Hz), 2.22–2.44 (1H, m), 6.73 (1H, d, J=1.6 Hz), 7.06–7.19 (7H, m), 7.26–7.39 (11H, m), 7.46 (1H, dt, J=7.8, 1.3 Hz), 7.59 (1H, t, J=1.8 Hz).

IR (KBr): 1493, 1472, 1445, 702 cm$^{-1}$.

(ii) Production of 1-(4'-chloro[1,1'-biphenyl]-3-yl)-2-methyl-1-(1-trityl-1H-imidazol-4-yl)-1-propanol By the reaction in the same manner as in Example 1-(i) using 4-chlorophenylboronic acid (0.49 g) and 1-(3-bromophenyl)-2-methyl-1-(1-trityl-1H-imidazol-4-yl)-1-propanol (1.04 g), the title compound (0.77 g) was obtained as a coloress solid.

$^1$H-NMR (CDCl$_3$) δ: 0.75 (3H, d, J=6.7 Hz), 0.94 (3H, d, J=6.7 Hz), 2.35–2.55 (1H, m), 6.78 (1H, d, J=1.4 Hz), 7.05–7.60 (23H, m), 7.65 (1H, s).

IR (KBr): 1493, 1476, 1445, 909 cm$^{-1}$.

(iii) Production of 1-(4'-chloro[1,1'-biphenyl]-3-yl)-1-(1H-imidazol-4-yl)-2-methyl-1-propanol 1-(4'-Chloro[1,1'-biphenyl]-3-yl)-2-methyl-1-(1-trityl-1H-imidazol-4-yl)-1-propanol (0.71 g) and pyridine hydrochloride (0.25 g) were dissolved in methanol (20 ml), and the mixture was stirred at 60° C. for 2 h. To the reaction mixture was added saturated aqueous sodium hydrogen carbonate solution and the mixture was concentrated. Water and ethyl acetate were added and the mixture was extracted with ethyl acetate. The organic layer was dried and concentrated, and the obtained residue was purified by silica gel column chomatography (eluent, dichloromethane:methanol=40:1). Recrystallization from hexane-ethyl acetate gave the title compound (0.31 g) as a colorless solid.

$^1$H-NMR (CDCl$_3$) δ: 0.82 (3H, d, J=6.8 Hz), 0.98 (3H, d, J=6.8 Hz), 2.50–2.78 (1H, m), 6.99 (1H, d, J=1.0 Hz), 7.33–7.44 (4H, m), 7.45–7.56 (4H, m), 7.78 (1H, s).

IR (KBr): 2969, 1476, 1092, 1013 cm$^{-1}$.

Example 13

Production of 1-(4'-fluoro[1,1'-biphenyl]-3-yl)-1-(1H-imidazol-4-yl)-2-methyl-1-propanol (i) Production of 1-(4'-fluoro[1,1'-biphenyl]-3-yl)-2-methyl-1-(1-trityl-1H-imidazol-4-yl)-1-propanol By the reaction in the same manner as in Example 1-(i) using 4-fluorophenylboronic acid (0.41 g) and 1-(3-bromophenyl)-2-methyl-1-(1-trityl-1H-imidazol-4-yl)-1-propanol (1.01 g), the title compound (0.71 g) was obtained as a pale-yellow solid.

$^1$H-NMR (CDCl$_3$) δ: 0.75 (3H, d, J=6.8 Hz), 0.93 (3H, d, J=6.8 Hz), 2.35–2.52 (1H, m), 6.78 (1H, d, J=1.0 Hz), 7.04–7.18 (8H, m), 7.22–7.38 (12H, m), 7.44–7.55 (3H, m), 7.63 (1H, s).

IR (KBr): 1512, 1480, 1233, 1159 cm$^{-1}$.

(ii) Production of 1-(4'-fluoro[1,1'-biphenyl]-3-yl)-1-(1H-imidazol-4-yl)-2-methyl-1-propanol By the reaction in the same manner as in Example 4-(iii) using 1-(4'-fluoro[1,1'-biphenyl]-3-yl)-2-methyl-1-(1-trityl-1H-imidazol-4-yl)-1-propanol (0.62 g), the title compound (0.27 g) was obtained as a colorless solid.

$^1$H-NMR (CDCl$_3$+CD$_3$OD) δ: 0.82 (3H, d, J=6.8 Hz), 0.98 (3H, d, J=6.8 Hz), 2.40–2.80 (1H, m), 6.70–7.16 (3H, m), 7.30–7.59 (6H, m), 7.72 (1H, s).

IR (KBr): 3187, 1514, 1236, 1005, 795 cm$^{-1}$.

Example 14

Production of 1-(2',4'-dichloro[1,1'-biphenyl]-3-yl)-1-(1H-imidazol-4-yl)-2-methyl-1-propanol (i) Production of 1-(2',4'-dichloro[1,1'-biphenyl]-3-yl)-2-methyl-1-(1-trityl-1H-imidazol-4-yl)-1-propanol By the reaction in the same manner as in Example 1-(i) using 2,4-dichlorophenylboronic acid (0.55 g) and 1-(3bromophenyl)-2-methyl-1-(1-trityl-1H-imidazol-4-yl)-1-propanol (1.00 g), the amorphous title compound (0.85 g) was obtained.

$^1$H-NMR (CDCl$_3$) δ: 0.76 (3H, d, J=6.8 Hz), 0.92 (3H, d, J=6.8 Hz), 2.30–2.52 (1H, m), 6.74 (1H, d, J=1.4 Hz), 7.04–7.50 (16H, m), 7.57 (1H, dt, J=7.8, 1.5 Hz).

IR (KBr): 1493, 1464, 1445, 1165 cm$^{-1}$.

(ii) Production of 1-(2',4'-dichloro[1,1'-biphenyl]-3-yl)-1-(1H-imidazol-4-yl)-2-methyl-1-propanol By the reaction in the same manner as in Example 12-(iii) using 1-(2',4'-dichloro[1,1'-biphenyl]-3-yl)-2-methyl-1-(1- trityl-1H-imidazol-4-yl)-1-propanol (0.80 g), the amorphous title compound (0.30 g) was obtained.

$^1$H-NMR (CDCl$_3$) δ: 0.81 (3H, d, J=6.7 Hz), 0.97 (3H, d, J=6.7 Hz), 2.45–2.70 (1H, m), 6.94 (1H, s), 7.12–7.60 (8H, m).

IR (KBr): 2969, 1466, 1103 cm$^{-1}$.

Example 15

Production of 1-[2'-(dimethoxymethyl)[1,1'-biphenyl]-3-yl]-1-(1H-imidazol-4-yl)-2-methyl-1-propanol (i) Production of 3'-[1-hydroxy-2-methyl-1-(1-trityl-1H-imidazol-4-yl)propyl][1,1'-biphenyl]-2-carbaldehyde By the reaction in the same manner as in Example 1-(i) using 2-formylphenylboronic acid (0.50 g) and 1-(3-bromophenyl)-2-methyl-1-(1-trityl-1H-imidazol-4-yl)-1-propanol (1.02 g), the amorphous title compound (0.93 g) was obtained.

$^1$H-NMR (CDCl$_3$) δ: 0.77 (3H, d, J=6.7 Hz), 0.93 (3H, d, J=6.7 Hz), 2.30–2.55 (1H, m), 6.73 (1H, d, J=1.4 Hz), 7.05–7.69 (23H, m), 8.03 (1H, dd, J=1.4, 7.8 Hz), 9.92 (1H, d, J=0.8 Hz).

IR (KBr): 1692, 1597, 1493, 1447 cm$^{-1}$.

(ii) Production of 1-[2'-(dimethoxymethyl)[1,1'-biphenyl]-3-yl]-1-(1H-imidazol-4-yl)-2-methyl-1-propanol By the reaction in the same manner as in Example 12-(iii) using 3'-[1-hydroxy-2-methyl-1-(1-trityl-1H-imidazol-4-yl)propyl][1,1'-biphenyl]-2-carbaldehyde (0.89 g), the amorphous title compound (0.28 g) was obtained.

$^1$H-NMR (CDCl$_3$) δ: 0.82 (3H, d, J=6.7 Hz), 0.97 (3H, d, J=6.7 Hz), 2.45–2.70 (1H, m), 3.10–3.40 (6H, m), 5.13 (1H, s), 6.93 (1H, m), 7.10–7.75 (9H, m).

IR (KBr): 2969, 1472, 1092, 1073 cm$^{-1}$.

Example 16

Production of 1-[3'-(dimethoxymethyl)[1,1'-biphenyl]-3-yl]-1-(1H-imidazol-4-yl)-2-methyl-1-propanol (i) Production of 3'-[1-hydroxy-2-methyl-1-(1-trityl-1H-imidazol-4-yl)propyl][1,1'-biphenyl]-3-carbaldehyde By the reaction in the same manner as in Example 1-(i) using 3-formylphenylboronic acid (0.45 g) and 1-(3bromophenyl)-2-methyl-1-(1-trityl-1H-imidazol-4-yl)-1-propanol (1.05 g), the amorphous title compound (0.80 g) was obtained.

$^1$H-NMR (CDCl$_3$) δ: 0.77 (3H, d, J=6.8 Hz), 0.95 (3H, d, J=6.8 Hz), 2.35–2.58 (1H, m), 6.79 (1H, d, J=1.6 Hz), 7.07–7.64 (20H, m), 7.74–7.90 (3H, m), 8.06 (1H, t, J=1.7 Hz), 10.07 (1H, s).

IR (KBr): 1698, 1445, 1163 cm$^{-1}$.

(ii) Production of 1-[3'-(dimethoxymethyl)[1,1'-biphenyl]-3-yl]-1-(1H-imidazol-4-yl)-2-methyl-1-propanol By the reaction in the same manner as in Example 12-(iii) using 3'-[1-hydroxy-2-methyl-1-(1-trityl-1H-imidazol-4-yl) propyl][1,1'-biphenyl]-3-carbaldehyde (0.70 g), the title compound (0.27 g) was obtained as a colorless solid.

$^1$H-NMR (CDCl$_3$) δ: 0.83 (3H, d, J=6.7 Hz), 0.99 (3H, d, J=6.7 Hz), 2.50–2.77 (1H, m), 3.37 (6H, m), 5.42 (1H, s), 6.93–7.01 (1H, m), 7.28–7.60 (7H, m), 7.66 (1H, s), 7.81 (1H, d, J=1.6 Hz).

IR (KBr): 2967, 1198, 1107, 1055 cm$^{-1}$.

Example 17

Production of 1-(1H-imidazol-4-yl)-2-methyl-1-(2'-methyl[1,1'-biphenyl]-3-yl)-1-propanol (i) Production of 2-methyl-1-(2'-methyl[1,1'-biphenyl]-3-yl)-1-(1-trityl-1H-imidazol-4-yl)-1-propanol By the reaction in the same manner as in Example 1-(i) using o-tolylboronic acid (0.69 g) and 1-(3-bromophenyl)-2-methyl-1-(1-trityl-1H-imidazol-4-yl)-1-propanol (1.01 g), the amorphous title compound (0.61 g) was obtained.

$^1$H-NMR (CDCl$_3$) δ: 0.77 (3H, d, J=6.7 Hz), 0.92 (3H, d, J=6.7 Hz), 2.18 (3H, s), 2.30–2.55 (1H, m), 6.73 (1H, d, J=1.4 Hz), 7.05–7.39 (23H, m), 7.54 (1H, dt, J=7.8, 1.2 Hz).

IR (KBr): 1493, 1474, 1445, 1161 cm$^{-1}$.

(ii) Production of 1-(1H-imidazol-4-yl)-2-methyl-1-(2'-methyl[1,1'-biphenyl]-3-yl)-1-propanol By the reaction in the same manner as in Example 12-(iii) using 2-methyl-1-(2'-methyl[1'-biphenyl]-3-yl)-1-(1-trityl-1H-imidazol-4-yl)-1-propanol (0.55 g), the amorphous title compound (0.20 g) was obtained.

$^1$H-NMR (CDCl$_3$) δ: 0.81 (3H, d, J=6.6 Hz), 0.97 (3H, d, J=6.6 Hz), 2.19 (3H, s), 2.48–2.70 (1H, m), 6.85–6.97 (1H, m), 7.10–7.54 (9H, m).

IR (KBr): 2970, 1474, 909 cm$^{-1}$.

Example 18

Production of 1-(1H-imidazol-4-yl)-2-methyl-1-(4'-methyl[1,1'-biphenyl]-3-yl)-1-propanol (i) Production of 2-methyl-1-(4'-methyl[1,1'-biphenyl]-3-yl)-1-(1-trityl-1H-imidazol-4-yl)-1-propanol By the reaction in the same manner as in Example 1-(i) using p-tolylboronic acid (0.45 g) and 1-(3-bromophenyl)-2-methyl-1-(1-trityl-1H-imidazol-4-yl)-1-propanol (1.03 g), the title compound (0.76 g) was obtained as a colorless solid.

$^1$H-NMR (CDCl$_3$) δ: 0.75 (3H, d, J=6.7 Hz), 0.93 (3H, d, J=6.7 Hz), 2.35–2.55 (1H, m), 2.40 (3H, s), 6.79 (1H, d, J=1.4 Hz), 7.06–7.54 (23H, m), 7.66 (1H, t, J=1.6 Hz).

IR (KBr): 1493, 1480, 1445, 1163 cm$^{-1}$.

(ii) Production of 1-(1H-imidazol-4-yl)-2-methyl-1-(4'-methyl[1,1-biphenyl]-3-yl)-1-propanol By the reaction in the same manner as in Example 12-(iii) using 2-methyl-1-(4'-methyl[1,1'-biphenyl]-3-yl)-1-(1-trityl-1H-imidazol-4-yl)-1-propanol (0.61 g), the title compound (0.23 g) was obtained as a colorless solid.

$^1$H-NMR (CDCl$_3$) δ: 0.82 (3H, d, J=6.7 Hz), 0.98 (3H, d, J=6.7 Hz), 2.38 (3H, s), 2.55–2.75 (1H, m), 6.98 (1H, s), 7.16–7.54 (8H, m), 7.77 (1H, t, J=1.6 Hz).

IR (KBr): 2969, 1480, 791, 735 cm$^{-1}$.

Example 19

Production of 1-(2',4'-difluoro[1,1'-biphenyl]-3-yl)-1-(1H-imidazol-4-yl)-2-methyl-1-propanol (i) Production of 1-(2',4'-difluoro[1,1'-biphenyl]-3-yl)-1-(1-trityl-1H-imidazol-4-yl)-2-methyl-1-propanol By the reaction in the same manner as in Example 4-(ii) using 1-(3-bromophenyl)-(1-trityl-1H-imidazol-4-yl)-2- methyl-1-propanol (6.00 g), 2,4-difluorophenylboronic acid (2.82 g), 2M aqueous sodium carbonate solution (45 ml) and tetrakis(triphenylphosphine)palladium(0) (647 mg), the yellow amorphous title compound (6.39 g) was obtained.

$^1$H-NMR (CDCl$_3$) δ: 0.76 (3H, d, J=6.8 Hz), 0.92 (3H, d, J=6.8 Hz), 2.35–2.49 (1H, m), 3.68 (1H, s), 6.76 (1H, d, J=1.4 Hz), 6.83–6.97 (2H, m), 7.09–7.16 (6H, m), 7.26–7.35 (13H, m), 7.36–7.57 (2H, m)

IR (KBr): 1508, 1480, 1447, 1140, 909, 747, 735, 702 cm$^{-1}$ (ii) Production of 1-(2',4'-difluoro[1,1'-biphenyl]-3-yl)-1-(1H-imidazol-4-yl)-2-methyl-1-propanol By the reaction in the same manner as in Example 4-(iii) using 1-(2',4'-difluoro[1,1'-biphenyl]-3-yl)-1-(1-trityl-1H-imidazol-4-yl)-2-methyl-1-propanol (6.31 g) and pyridine hydrochloride (2.17 g), the title compound (2.93 g) was obtained as colorless needle crystals.

$^1$H-NMR (CDCl$_3$) δ: 0.83 (3H, d, J=6.6 Hz), 0.98 (3H, d, J=6.6 Hz), 2.56–2.73 (1H, m), 6.84–6.98 (3H, m), 7.32–7.52 (5H, m), 7.69 (1H, s)

IR (KBr): 3202, 1508, 1478, 1385, 1364, 1142, 1005, 855, 845, 797 cm$^{-1}$

Example 20

Production of 1-(3'-fluoro[1,1'-biphenyl]-3-yl)-1-(1H-imidazol-4-yl)-2-methyl-1-propanol (i) 1-(3'-fluoro[1,1'-biphenyl]-3-yl)-1-(1-trityl-1H-imidazol-4-yl)-2-methyl-1-propanol By the reaction in the same manner as in Example 4-(ii) using 1-(3-bromophenyl)-(1-trityl-1H-imidazol-4-yl)-2-methyl-1-propanol (2.62 g), 3-fluorophenylboronic acid (1.09 g), 2M aqueous sodium carbonate solution (19.5 ml) and tetrakis(triphenylphosphine)palladium(0) (281 mg), the yellow amorphous title compound (2.55 g) was obtained.

$^1$H-NMR (CDCl$_3$) δ: 0.75 (3H, d, J=6.6 Hz), 0.94 (3H, d, J=6.6 Hz), 2.36–2.50 (1H, m), 3.70 (1H, s), 6.78 (1H, d, J=1.2 Hz), 6.98–7.43 (22H, m), 7.55 (1H, dt, J=6.6, 2.0 Hz), 7.65 (1H, s)

IR (KBr) cm$^{-1}$: 1493, 1472, 1445, 1159, 909, 781, 747, 735, 702 cm$^{-1}$ (ii) Production of 1-(3'-fluoro[1,1'-biphenyl]-3-yl)-1-(1H-imidazol-4-yl)-2-methyl-1-propanol By the reaction in the same manner as in Example 4-(iii) using 1-(3'-fluoro[1,1'-biphenyl]-3-yl)-1-(1-trityl-1H-imidazol-4-yl)-2-methyl-1-propanol (2.55 g) and pyridine hydrochloride (906 mg), the title compound (1.15 g) was obtained as colorless needle crystals.

$^1$H-NMR (CDCl$_3$) δ: 0.83 (3H, d, J=7.0 Hz), 0.99 (3H, d, J=7.0 Hz), 2.59–2.72 (1H, m), 3.52 (1H, br s), 7.00–7.06 (2H, m), 7.30–7.40 (5H, m), 7.55 (2H, br s), 7.81 (1H, br s), 9.28 (1H, br s)

IR (KBr) cm$^{-1}$: 3179, 1576, 1472, 1362, 1304, 1200, 1005, 777, 693 cm$^{-1}$

Example 21

Production of 1-(1H-imidazol-4-yl)-2-methyl-1-[4'-(trifluoromethyl)[1,1'-biphenyl]-3-yl]-1-propanol (i) Production of 2-methyl-1-[4'-(trifluoromethyl)[1,1'-biphenyl]-3-yl]-1-(1-trityl-1H-imidazol-4-yl)-1-propanol By the reaction in the same manner as in Example 4-(ii) using 1-(3-bromophenyl)-(1-trityl-1H-imidazol-4-yl)-2-methyl-1-propanol (3.01 g), 4-trifluoromethylphenylboronic acid (1.70 g), 2M aqueous sodium carbonate solution (22.4 ml) and tetrakis(triphenylphosphine)palladium(0) (323 mg), the title compound (2.58 g) was obtained as colorless needle crystals.

$^1$H-NMR (CDCl$_3$) δ: 0.76 (3H, d, J=7.0 Hz), 0.94 (3H, d, J=7.0 Hz), 2.45–2.50 (1H, m), 3.70 (1H, s), 6.78 (1H, d, J=1.2 Hz), 7.09–7.14 (6H, m), 7.23–7.40 (12H, m), 7.55–7.69 (6H, m)

IR (KBr): 1447, 1327, 1167, 1125, 1073, 849, 793, 747, 735, 702 cm$^{-1}$ (ii) Production of 1-(1H-imidazol-4-yl)-2-methyl-1-[4'-(trifluoromethyl)[1,1'-biphenyl]-3-yl]-1-propanol By the reaction in the same manner as in Example 4-(iii) using 2-methyl-1-[4'-(trifluoromethyl)[1,1'-biphenyl]-3-yl]-1-(1-trityl-1H-imidazol-4-yl)-1-propanol (2.55 g) and pyridine hydrochloride (831 mg), the title compound (1.31 g) was obtained as colorless needle crystals.

$^1$H-NMR (CDCl$_3$) δ: 0.83 (3H, d, J=6.6 Hz), 0.99 (3H, d, J=6.6 Hz), 2.59–2.73 (1H, m), 3.37 (1H, br s), 7.01 (1H, s), 7.35–7.46 (2H, m), 7.55–7.67 (6H, m), 7.84 (1H, s), 9.24 (1H, br s)

IR (KBr): 3252, 1327, 1171, 1119, 1073, 966, 845, 797 cm$^{-1}$

Example 22

Production of 1-(1H-imidazol-4-yl)-2-methyl-1-[4'-(trifluoromethoxy)[1,1'-biphenyl]-3-yl]-1-propanol (i) Production of 2-methyl-1-[4'-(trifluoromethoxy)[1,1'-biphenyl]-3-yl]-1-(1-trityl-1H-imidazol-4-yl)-1-propanol By the reaction in the same manner as in Example 4-(ii) using 1-(3-bromophenyl)-(1-trityl-1H-imidazol-4-yl)-2-methyl-1-propanol (3.80 g) 4-trifluoromethoxyphenylboronic acid (2.33 g), 2M aqueous sodium carbonate solution (28.3 ml) and tetrakis(triphenylphosphine)palladium(0) (408 mg), the title compound (3.67 g) was obtained as colorless needle crystals.

$^1$H-NMR (CDCl$_3$) δ: 0.75 (3H, d, J=7.0 Hz), 0.94 (3H, d, J=7.0 Hz), 2.36–2.50 (1H, m), 3.70 (1H, s), 6.78 (1H, d, J=1.0 Hz), 7.10–7.16 (6H, m), 7.23–7.40 (14H, m), 7.50–7.64 (4H, m)

IR (KBr): 1493, 1481, 1445, 1264, 1225, 1165, 1015, 793, 747, 700 cm$^{-1}$ (ii) Production of 1-(1H-imidazol-4-yl)-2-methyl-1-[4'-(trifluoromethoxy)[1,1'-biphenyl]-3-yl]-1-propanol By the reaction in the same manner as in Example 4-(iii) using 2-methyl-1-[4'-(trifluoromethoxy)[1,1'-biphenyl]-3-yl]-1-(1-trityl-1H-imidazol-4-yl)-1-propanol (3.63 g) and pyridine hydrochloride (1.22 g), the title compound (3.76 g) was obtained as colorless needle crystals.

$^1$H-NMR (CDCl$_3$) δ: 0.82 (3H, d, J=6.6 Hz), 0.98 (3H, d, J=6.6 Hz), 2.57–2.71 (1H, m), 6.98 (1H, d, J=0.8 Hz), 7.18–7.39 (4H, m), 7.51–7.59 (4H, m), 7.78 (1H, s)

IR (KBr): 1510, 1478, 1271, 1227, 1167, 1105, 855, 829, 791, 708 cm$^{-1}$

Example 23

Production of 1-[4'-fluoro-3-(methoxymethyl)[1,1'-biphenyl]-3-yl]-1-(1H-imidazol-4-yl)-2-methyl-1-propanol (i) Production of 4-bromo-1-fluoro-2-(methoxymethyl)benzene To a solution of (5-bromo-2-fluorophenyl)methanol (5.00 g) in THF (100 ml) was added 60% sodium hydride (1.08 g)

at 0° C., and the mixture was stirred at room temperature for 30 min. Methyl iodide (3.80 ml) was added, and the mixture was stirred for 1.5 h. Water was added to the reaction mixture, and the mixture was extracted with ethyl acetate, washed with saturated brine and dried. The solvent was evaporated under reduced pressure and the residue was purified by column chomatography (eluent, hexane→hexane:ethyl acetate=50:1) to give the title compound (4.86 g) as a brown oil.

$^1$H-NMR (CDCl$_3$) δ: 3.42 (3H, s), 4.92 (2H, s), 6.93 (1H, dd, J=8.8, 8.8 Hz), 7.34–7.42 (1H, m), 7.56 (1H, dd, J=2.2, 6.2 Hz)

IR (KBr): 1485, 1456, 1383, 1238, 1177, 1123, 1101, 814, 623 cm$^{-1}$ (ii) Production of 1-[4'-fluoro-3'-(methoxymethyl)[1,1'-biphenyl]-3-yl]-1-(1-trityl-1H-imidazol-4-yl)-2-methyl-1-propanol To a solution of 4-bromo-1-fluoro-2-(methoxymethyl)benzene (4.86 g) in THF (60 ml) was added dropwise n-butyllithium (1.6M; 15.3 ml) at −78° C., and the mixture was stirred for 40 min. Triisopropoxyborane (10.2 ml) was added dropwise, and the mixture was stirred at room temperature for 15 h. To the reaction mixture was added 2N hydrochloric acid (20 ml) at 0° C. and the mixture was extracted with ethyl acetate, washed with saturated brine and dried. The solvent was evaporated under reduced pressure to give a crude product (4.50 g) of 4-fluoro-3-(methoxymethyl)phenylboronic acid as a yellow oil. By the reaction in the same manner as in Example 4-(ii) using this product (1.36 g), 1-(3-bromophenyl)-(1-trityl-1-1H-imidazol-4-yl)-2-methyl-1-propanol (1.50 g), 2M aqueous sodium carbonate solution (11.2 ml) and tetrakis(triphenylphosphine)palladium(0) (161 mg), the yellow amorphous title compound (1.36 g) was obtained.

$^1$H-NMR (CDCl$_3$) δ: 0.78 (3H, d, J=6.6 Hz), 0.96 (3H, d, J=6.6 Hz), 2.43–2.50 (1H, m), 3.45 (3H, s), 4.58 (2H, s), 6.80 (1H, d, J=1.2 Hz), 7.12–7.19 (7H, m), 7.28–7.52 (15H, m), 7.62 (1H, d, J=2.2, 7.0 Hz), 7.71 (1H, s)

IR (KBr): 1493, 1478, 1445, 1188, 1159, 1121, 1094, 909, 748, 733, 702 cm$^{-1}$ (iii) Production of 1-[4'-fluoro-3'-(methoxymethyl)[1,1'-biphenyl]-3-yl]-1-(1H-imidazol-4-yl)-2-methyl-1-propanol By the reaction in the same manner as in Example 4-(iii) using 1-[4'-fluoro-3'-(methoxymethyl)[1,1'-biphenyl]-3-yl]-1-(1-trityl-1H-imidazol-4-yl)-2-methyl-1-propanol (1.35 g) and pyridine hydrochloride (469 mg), the colorless amorphous title compound (629 mg) was obtained.

$^1$H-NMR (CDCl$_3$) δ: 0.79 (3H, d, J=6.6 Hz), 0.96 (3H, d, J=6.4 Hz), 2.56–2.62 (1H, m), 3.41 (3H, s), 4.54 (2H, s), 6.88 (1H, s), 6.99–7.08 (1H, m), 7.30–7.57 (6H, m), 7.73 (1H, s) IR (KBr): 2971, 1505, 1478, 1385, 1229, 1192, 1123, 1092, 1007, 828, 793 cm$^{-1}$

Example 24

Production of 1-(4'-fluoro-6-methoxy[1,1'-biphenyl]-3-yl)-1-(1H-imidazol-4-yl)-2-methyl-1-propanol (i) Production of 4'-fluoro-6-methoxy[1,1'-biphenyl]-3-carbaldehyde By the reaction in the same manner as in Example 5-(ii) using 3-bromo-p-anisaldehyde (14.0 g), 4-fluorophenylboronic acid (14.6 g), 2M aqueous sodium carbonate solution (260 ml) and tetrakis(triphenylphosphine)palladium(0) (3.76 g), the title compound (11.9 g) was obtained as white needle crystals.

$^1$H-NMR (CDCl$_3$) δ: 3.91 (3H, s), 7.07–7.16 (3H, m), 7.46–7.53 (2H, m), 7.82–7.90 (2H, m), 9.94 (1H, s)

IR (KBr): 1694, 1599, 1497, 1265, 1225, 1177, 1020, 839, 814 cm$^{-1}$ (ii) Production of 1-(4'-fluoro-6-methoxy[1,1'-biphenyl]-3-yl)-2-methyl-1-propanol To a solution of 4'-fluoro-6-methoxy[1,1'-biphenyl]-3-carbaldehyde (5.00 g) in THF (80 ml) was added dropwise a solution (0.63; 44.8 ml) of isopropylmagnesium bromide in THF at 0° C., and the mixture was stirred for 1 h 45 min. To the reaction mixture was added saturated aqueous ammonium chloride solution and the mixture was extracted with ethyl acetate, washed with saturated brine and dried. The solvent was evaporated under reduced pressure and the residue was purified by column chomatography (eluent, hexane:ethyl acetate=6:1→2:1) to give the title compound (3.82 g) as a yellow oil.

$^1$H-NMR (CDCl$_3$) δ: 0.81 (3H, d, J=6.6 Hz), 1.02 (3H, s, J=6.6 Hz), 1.79 (1H, d, J=3.2 Hz), 1.88–2.02 (1H, m), 3.81 (3H, s), 4.35 (1H, dd, J=3.0, 7.0 Hz), 6.92–7.15 (3H, m), 7.24–7.29 (2H, m), 7.44–7.53 (2H, m)

IR (KBr): 1514, 1495, 1464, 1264, 1233, 1159, 1044, 1026, 837, 814 cm$^{-1}$ (iii) Production of 1-(4'-fluoro-6-methoxy[1,1'-biphenyl]-3-yl)-2-methyl-1-propanone To a solution of 1-(4'-fluoro-6-methoxy[1,1'-biphenyl]-3-yl)-2-methyl-1-propanol (3.82 g) in dichloromethane (60 ml) was added manganese(IV) dioxide (12.1 g), and the mixture was stirred at room temperature for 17 h. Manganese(IV) dioxide (17.7 g) was added and the mixture was stirred at room temperature for 1.5 h. The mixture was heated under reflux for 22 h and filtered through Celite. The solvent was evaporated under reduced pressure to give the title compound (3.73 g) as a yellow oil.

$^1$H-NMR (CDCl$_3$) δ: 1.23 (6H, d, J=6.6 Hz), 3.55 (1H, m, J=6.6 Hz), 3.89 (3H, s), 7.00–7.17 (3H, m), 7.44–7.54 (2H, m), 7.92–8.01 (2H, m)

IR (KBr): 1674, 1599, 1514, 1497, 1267, 1208, 1159, 1150, 990, 839 cm$^{-1}$ (iv) 1-(4'-fluoro-6-methoxy[1,1'-biphenyl]-3-yl)-1-(1H-imidazol-4-yl)-2-methyl-1-propanol To a solution of 4-iodo-1H-imidazole (2.13 g) and tetramethylethylenediamine (1.66 ml) in THF (50 ml) was added dropwise a solution (3 M; 14.7 ml) of ethylmagnesium bromide in diethyl ether under ice-cooling and the mixture was heated to 55° C. The mixture was stirred for 1 h and copper(I) iodide (178 mg) was added at 40° C. The mixture was stirred at 40–45° C. for 5 min and a solution of 1-(4'-fluoro-6-methoxy[1,1'-biphenyl]-3-yl)-2-methyl-1-propane (3.73 g) in THF (20 ml) was added dropwise at 30° C. The mixture was stirred at room temperature for 4 h. Saturated ammonium chloride was added to the reaction mixture and the mixture was extracted with ethyl acetate, washed with 5% aqueous ethylene diamine solution and saturated brine, and dried. The solvent was evaporated under reduced pressure and the residue was purified by column chomatography (eluent, hexane:ethyl acetate=1:2→ethyl acetate) to give the colorless amorphous title compound (922 mg).

¹H-NMR (CDCl₃) δ: 0.84 (3H, d, J=7.0 Hz), 0.96 (3H, d, J=7.0 Hz), 2.54–2.67 (1H, m), 3.78 (3H, s), 6.89–17.11 (4H, m), 7.43–7.54 (5H, m)

IR (KBr): 1514, 1493, 1464, 1264, 1227, 1157, 1026, 837, 818 cm⁻¹

Example 25

Production of 3'-[1-hydroxy-1-(1H-imidazol-4-yl)-2-methyl-1-propyl][1,1'-biphenyl]-4-carbonitrile (i) Production of 3'-[1-hydroxy-2-methyl-1-(1-trityl-1H-imidazol-4-yl)-1-propyl][1,1'-biphenyl]-4-carbonitrile By the reaction in the same manner as in Example 4-(ii) using 1-(3-bromophenyl)-(1-trityl-1-1H-imidazol-4-yl)-2-methyl-1-propanol (978 mg), 4-cyanophenylboronic acid (535 mg), 2M aqueous sodium carbonate solution (7.28 ml) and tetrakis(triphenylphosphine)palladium(0) (105 mg), the title compound (622 mg) was obtained as colorless needle crystals.

¹H-NMR (CDCl₃) δ: 0.75 (3H, d, J=6.6 Hz), 0.94 (3H, d, J=7.0 Hz), 2.40–2.47 (1H, m), 3.68 (1H, s), 6.78 (1H, d, J=1.6 Hz), 7.10–7.14 (6H, m), 7.29–7.40 (12H, m), 7.55–7.73 (6H, m)

IR (KBr): 2965, 2226, 1605, 1491, 1480, 1445, 845, 795, 754, 745, 700 cm⁻¹

(ii) Production of 3'-[1-hydroxy-1-(1H-imidazol-4-yl)-2-methyl-1-propyl][1,1'-biphenyl]-4-carbonitrile By the reaction in the same manner as in Example 4-(iii) using 3'-[1-hydroxy-2-methyl-1-(1-trityl-1H-imidazol-4-yl)-1-propyl][1,1'-biphenyl]-4-carbonitrile (590 mg) and pyridine hydrochloride (111 mg), the title compound (261 mg) was obtained as colorless needle crystals.

¹H-NMR (CDCl₃) δ: 0.82 (3H, d, J=7.0 Hz), 0.91 (3H, d, J=6.6 Hz), 2.59–2.73 (1H, m), 6.99 (1H, s), 7.36–7.43 (2H, m), 7.53–7.69 (6H, m), 7.83 (1H, s)

IR (KBr): 2232, 1605, 1478, 1103, 843, 791, 727, 708, 644 cm⁻¹

Example 26

Production of 1-(4'-fluoro[1,1'-biphenyl]-3-yl)-1-(1H-imidazol-4-yl)-1-ethanol (i) Production of 1-(4'-fluoro[1,1'-biphenyl]-3-yl)-1-(1-trityl-1H-imidazol-4-yl)-1-ethanol To a solution of 3-bromo-4'-fluoro-1,1'-biphenyl (1.50 g) in THF (20 ml) was added dropwise a solution (1.6 M; 3.73 ml) of n-butyllithium in hexane at −78° C., and the mixture was stirred for 20 min. A solution of 1-(1-trityl-1H-imidazol-4-yl)-1-ethanone (1.91 g) in THF (25 ml) was added dropwise at −78° C., and the mixture was stirred at −78° C. for 1 h, at −35 to −10° C. for 1 h and at 0° C. for 1 h. Saturated aqueous ammonium chloride solution was added to the reaction mixture and the mixture was extracted with ethyl acetate, washed with saturated brine and dried. The solvent was evaporated under reduced pressure and the residue was purified by column chomatography (eluent, hexane:ethyl acetate=3:1→1:1) and recrystallized from ethyl acetate-hexane to give the title compound (1.57 g) as colorless prism crystals.

¹H-NMR (CDCl₃) δ: 1.81 (3H, s), 3.44 (1H, s), 6.77 (1H, d, J=1.4 Hz), 7.06–7.28 (8H, m), 7.30–7.55 (16H, m)

IR (KBr): 1514, 1483, 1441, 1221, 1163, 839, 797, 758, 750, 702 cm⁻¹

(ii) Production of 1-(4'-fluoro[1,1'-biphenyl]-3-yl)-1-(1H-imidazol-4-yl)-1-ethanol By the reaction in the same manner as in Example 4-(iii) using 1-(4'-fluoro[1,1'-biphenyl]-3-yl)-1-(1-trityl-1H-imidazol-4-yl)-1-ethanol (1.51 g) and pyridine hydrochloride (599 mg), the title compound (559 mg) was obtained as colorless plate crystals.

¹H-NMR (CDCl₃+CD₃OD) δ: 1.91 (3H, s), 6.89 (1H, s), 7.05–7.14 (2H, m), 7.35–7.42 (3H, m), 7.48–7.55 (3H, m), 7.65 (1H, s)

IR (KBr): 3166, 1514, 1481, 1456, 1231, 1190, 1067, 833, 799, 623 cm⁻¹

Example 27

Production of 1-[4'-fluoro[1,1'-biphenyl]-3-yl]-1-(1H-imidazol-4-yl)-1-propanol

By the reaction in the same manner as in Example 26-(i) using 3-bromo-4'-fluoro-1,1'-biphenyl (2.80 g), a solution (1.6 M; 6.96 ml) of n-butyllithium in hexane and 1-(1H-imidazol-4yl)-1-propanone (419 mg), the title compound (796 mg) was obtained as colorless plate crystals.

¹H-NMR (CDCl₃+CD₃OD) δ: 0.89 (3H, J=7.2 Hz), 2.14–2.36 (2H, m) 6.90 (1H, s), 7.05–7.14 (2H, m), 7.37–7.56 (6H, m), 7.65 (1H, s)

IR (KBr): 3191, 1512, 1235, 1181, 1096, 963, 934, 835, 799, 619 cm⁻¹

Example 28

Production of 1-(1H-imidazol-4-yl)-2-methyl-1-[3-(2-thienyl)phenyl]-1-propanol (i) Production of 2-methyl-1-[3-(2-thienyl)phenyl]-1-(1-trityl-1H-imidazol-4-yl)-1-propanol 1-(3-Bromophenyl)-1-(1-trityl-1H-imidazol-4-yl)-2-methyl-1-propanol (1.70 g) and a solution of tri-n-butyl(2-thienyl)tin (1.31 ml) in DMF (10 ml) were deaerated and tetrakis(triphenylphosphine)palladium(0) (110 mg) was added. The mixture was stirred under an argon atmosphere at 80° C. for 4 h. Water was added to the reaction mixture and the mixture was extracted with ethyl acetate, washed twice with water and then with saturated brine, and dried. The solvent was evaporated under reduced pressure and the residue was purified by silica gel column chomatography (eluent, hexane:ethyl acetate=6:1→3:1). Recrystallization from ethyl acetate-hexane gave the title compound (1.32 g) as colorless powder crystals.

¹H-NMR (CDCl₃) δ: 0.75 (3H, d, J=6.8 Hz), 0.92 (3H, d, J=6.6 Hz), 2.35–2.48 (1H, m), 3.68 (1H, s), 6.79 (1H, d, J=1.0 Hz), 7.04–7.16 (6H, m), 7.24–7.35 (14H, m), 7.41–7.47 (2H, m), 7.72 (1H, s)

IR (KBr): 1493, 1445, 1165, 1003, 909, 747, 700 cm⁻¹

(ii) Production of 1-(1H-imidazol-4-yl)-2-methyl-1-[3-(2-thienyl)phenyl]-1-propanol By the reaction in the same manner as in Example 4-(iii) using 2-methyl-1-[3-(2-thienyl)phenyl]-1-(1-trityl-1H-imidazol-4-yl)-1-propanol (1.21 g) and pyridine hydrochloride (465 mg), the title compound (585 mg) was obtained as colorless plate crystals.

¹H-NMR (CDCl₃+CD₃OD) δ: 0.82 (3H, d, J=7.0 Hz), 0.99 (3H, d, J=6.4 Hz), 2.56–2.70 (1H, m), 6.9.8 (1H, d,

J=1.2 Hz), 7.06 (1H, dd, J=3.8, 5.2 Hz), 7.24–7.49 (5H, m), 7.51 (1H, d, J=1.2 Hz), 7.80 (1H, s)

IR (KBr): 3194, 2969, 1385, 1366, 1306, 1007, 822, 787, 693, 635 cm$^{-1}$

Example 29

Production of 1-(1H-imidazol-4-yl)-2-methyl-1-[3-(3-thienyl)phenyl]-1-propanol (i) Production of 2-methyl-1-[3-(3-thienyl)phenyl]-1-(1-trityl-1H-imidazol-4-yl)-1-propanol To a suspension of 1-(3-bromophenyl)-1-(1-trityl-1H-imidazol-4-yl)-2-methyl-1-propanol (1.70 g), 3-thiopheneboronic acid (607 mg) and 2M aqueous sodium carbonate solution (3.16 ml) in toluene-ethanol (6:1) (17.5 ml) was added tetrakis(triphenylphosphine)palladium(0) (110 mg), and the mixture was heated under reflux for 3 h under an argon atmosphere. Water was added to the reaction mixture, and the mixture was extracted with ethyl acetate, washed with saturated brine and dried. The solvent was evaporated under reduced pressure and the residue was purified by silica gel column chomatography (eluent, hexane:ethyl acetate=6:1→4:1→3:1). Recrystallization from ethyl acetate-hexane gave the title compound (1.48 g) as colorless powder crystals.

$^1$H-NMR (CDCl$_3$) δ: 0.75 (3H, d, J=6.6 Hz), 0.93 (3H, d, J=6.6 Hz), 2.36–2.49 (1H, m), 3.67 (1H, s), 6.78 (1H, d, J=1.4 Hz), 7.10–7.17 (6H, m), 7.25–7.48 (16H, m), 7.70 (1H, dd, J=1.8, 1.8 Hz)

IR (KBr): 1493, 1445, 1163, 1003, 909, 775, 747, 733, 702 cm$^{-1}$ (ii) Production of 1-(1H-imidazol-4-yl)-2-methyl-1-[3-(3-thienyl)phenyl]-1-propanol By the reaction in the same manner as in Example 4-(iii) using 2-methyl-1-[3-(3-thienyl)phenyl]-1-(1-trityl-1H-imidazol-4-yl)-1-propanol (1.43 g) and pyridine hydrochloride (550 mg), the title compound (585 mg) was obtained as colorless plate crystals.

$^1$H-NMR (CDCl$_3$+CD$_3$OD) δ: 0.82 (3H, d, J=7.0 Hz), 0.98 (3H, d, J=7.0 Hz), 2.57–2.70 (1H, m), 6.96 (1H, d, J=1.0 Hz), 7.28–7.48 (7H, m), 7.79 (1H, s)

IR (KBr): 3196, 2969, 1358, 1304, 1007, 801, 787, 774 cm$^{-1}$

Example 30

Production of 1-[3-(2-furyl)phenyl]-1-(1H-imidazol-4-yl)-2-methyl-1-propanol (i) Production of 1-[3-(2-furyl)phenyl]-2-methyl-1-(1-trityl-1H-imidazol-4-yl)-1-propanol By the reaction in the same manner as in Example 28-(i) using 1-(3-bromophenyl)-1-(1-trityl-1H-imidazol-4-yl)-2-methyl-1-propanol (1.70 g), tri-n-butyl(2-furyl)tin (1.29 ml) and tetrakis(triphenylphosphine)palladium((0) (110 mg), the title compound (1.62 g) was obtained as colorless powder crystals.

$^1$H-NMR (CDCl$_3$) δ: 0.75 (3H, d, J=6.6 Hz), 0.92 (3H, d, J=6.8 Hz), 2.36–2.50 (1H, m), 3.67 (1H, s), 6.46 (1H, dd, J=1.8, 3.2 Hz), 6.60 (1H, d, J=3.2 Hz), 6.79 (1H, d, J=1.4 Hz), 7.10–7.15 (6H, m), 7.28–7.35 (11H, m), 7.41–7.51 (3H, m), 7.79 (1H, dd, J=1.8, 1.8 Hz)

IR (KBr): 1493, 1472, 1445, 1161, 1013, 910, 791, 733, 702, 660 cm$^{-1}$ (ii) Production of 1-[3-(2-furyl)phenyl]-1-(1H-imidazol-4-yl)-2-methyl-1-propanol By the reaction in the same manner as in Example 4-(iii) using 1-[3-(2-furyl)phenyl]-2-methyl-1-(1-trityl-1H-imidazol-4-yl)-1-propanol (1.54 g) and pyridine hydrochloride (610 mg), the title compound (597 mg) was obtained as colorless plate crystals.

$^1$H-NMR (CDCl$_3$+CD$_3$OD) δ: 0.81 (3H, d, J=6.6 Hz), 0.99 (3H, d, J=6.6 Hz), 2.57–2.71 (1H, m), 6.46 (1H, dd, J=1.8, 3.4 Hz), 6.65 (1H, d, J=1.8 Hz), 6.98 (1H, d, J=3.4 Hz), 7.27–7.51 (5H, m), 7.85 (1H, s)

IR (KBr): 3200, 2975, 1306, 1188, 1007, 789, 729, 693, 635 cm$^{-1}$

Example 31

Production of N-{4'-[1-hydroxy-1-(1H-imidazol-4-yl)-2-methylpropyl][1,1'-biphenyl]-3-yl}acetamide (i) Production of N-{4'-[1-hydroxy-2-methyl-1-(1-trityl-1H-imidazol-4-yl)propyl][1,1'-biphenyl]-3-yl}acetamide By the reaction in the same manner as in Example 4-(ii) using 1-(4-bromophenyl)-2-methyl-1-(1-trityl-1H-imidazol-4-yl)-1-propanol (1.04 g), 3-(acetylamino)phenylboronic acid (571 mg) and tetrakis(triphenylphosphine)palladium(0) (301 mg), the title compound (1.10 g) was obtained as a pale-yellow amorphous powder.

$^1$H-NMR (CDCl$_3$) δ: 0.76 (3H, d, J=6.6 Hz), 0.92 (3H, d, J=6.6 Hz), 2.20 (3H, s), 2.38–2.56 (1H, m), 3.55 (1H, s), 6.77 (1H, d, J=1.2 Hz), 7.06–7.20 (6H, m), 7.24–7.76 (18H, m).

IR (KBr): 3063, 1674, 1557, 1483, 1445 cm$^{-1}$.

(ii) Production of N-{4'-[1-hydroxy-1-(1H-imidazol-4-yl)-2-methylpropyl][1,1'-biphenyl]-3-yl}acetamide By the reaction in the same manner as in Example 4-(iii) using N-{4'-[1-hydroxy-2-methyl-1-(1-trityl-1H-imidazol-4-yl)propyl][1,1'-biphenyl]-3-yl}acetamide (978 mg) and pyridine hydrochloride (310 mg), the title compound (276 mg) was obtained as a colorless amorphous powder.

$^1$H-NMR (CDCl$_3$+CD$_3$OD) δ: 0.82 (3H, d, J=6.8 Hz), 0.98 (3H, d, J=6.8 Hz), 2.17 (3H, s), 2.51–2.74 (1H, m), 6.96 (1H, d, J=1.0 Hz), 7.25–7.39 (3H, m), 7.42–7.56 (5H, m), 7.68 (1H, s).

IR (KBr): 3210, 2971, 1672, 1557, 1483 cm$^{-1}$.

Example 32

Production of N-{4'-[1-hydroxy-1-(1H-imidazol-4-yl)-2-methylpropyl][1,1'-biphenyl]-4-yl}acetamide (i) Production of N-{4'-[1-hydroxy-2-methyl-1-(1-trityl-1H-imidazol-4-yl)propyl][1,1'-biphenyl]-4-yl}acetamide By the reaction in the same manner as in Example 4-(ii) using 1-(4-bromophenyl)-2-methyl-1-(1-trityl-1H-imidazol-4-yl)-1-propanol (1.00 g), 4-(acetylamino)phenylboronic acid (510 mg) and tetrakis(triphenylphosphine)palladium(0) (200 mg), the title compound (350 mg) was obtained as a colorless powder crystals.

$^1$H-NMR (CDCl$_3$) δ: 0.77 (3H, d, J=6.6 Hz), 0.93 (3H, d, J=6.6 Hz), 2.20 (3H, s), 2.30–2.56 (1H, m), 3.53 (1H, s), 6.77 (1H, d, J=1.4 Hz), 7.08–7.14 (6H, m), 7.27–7.38 (10H, m), 7.43–7.58 (8H, m).

IR (KBr): 2971, 1671, 1535, 1493 cm$^{-1}$.

(ii) Production of N-{4'-[1-hydroxy-1-(1H-imidazol-4-yl)-2-methylpropyl][1,1'-biphenyl]-4-yl}acetamide By the reaction in the same manner as in Example 4-(iii) using N-{4'-[1-hydroxy-2-methyl-1-(1-trityl-1H-imidazol-4-yl)propyl][1,1'-biphenyl]-4-yl}acetamide (601 mg) and pyridine hydrochloride (0.17 g), the title compound (73 mg) was obtained as colorless powder crystals.

$^1$H-NMR (CDCl$_3$+CD$_3$OD) δ: 0.82 (3H, d, J=6.8 Hz), 0.98 (3H, d, J=6.8 Hz), 2.17 (3H, s), 2.49–2.70 (1H, m), 6.96 (1H, d, J=0.8 Hz), 7.44–7.60 (9H, m).

IR (KBr): 3173, 1667, 1534, 1499 cm$^{-1}$.

Example 33

Production of N-{4-fluoro-4'-[1-hydroxy-1-(1H-imidazol-4-yl)-2-methylpropyl][1,1'-biphenyl]-3-yl}acetamide (i) Production of N-(5-bromo-2-fluorophenyl)acetamide 4-Bromo-1-fluoro-2-nitrobenzene (5.81 g), iron powder (6.20 g) and acetic anhydride (5 ml) were stirred in acetic acid (50 ml) at 60° C. for 16 h. Acetic acid was evaporated under reduced pressure and water and ethyl acetate were added. The organic layer was washed with aqueous sodium hydrogen carbonate and brine, dried over magnesium sulfate and concentrated under reduced pressure. The residue was recrystallized from hexane-ethyl acetate to give the title compound (3.56 g) as colorless prism crystals.

$^1$H-NMR (CDCl$_3$) δ: 2.23 (3H, s), 6.87–7.03 (1H, m), 7.06–7.21 (1H, m), 7.43 (1H, brs), 8.53 (1H, d, J=6.8 Hz).

IR (KBr): 3262, 1672, 1613, 1535, 1408 cm$^{-1}$.

(ii) Production of N-{4-fluoro-4'-[1-hydroxy-2-methyl-1-(1-trityl-1H-imidazol-4-yl)propyl][1,1'-biphenyl]-3-yl}acetamide By the reaction in the same manner as in Example 4-(ii) using 4-[1-hydroxy-2-methyl-1-(1-trityl-1H-imidazol-4-yl)propyl]phenylboronic acid (3.50 g), N-(5-bromo-2-fluorophenyl)acetamide (1.17 g) and tetrakis(triphenylphosphine)palladium(0) (0.17 g), the title compound (1.39 g); was obtained as a colorless amorphous powder.

$^1$H-NMR (CDCl$_3$) δ: 0.76 (3H, d, J=7.0 Hz), 0.92 (3H, d, J=7.0 Hz), 2.24 (3H, s), 3.55 (1H, s), 6.77 (1H, d, J=1.0 Hz), 7.06–7.20 (7H, m), 7.20–7.36 (11H, m), 7.47 (2H, d, J=8.8 Hz), 7.54 (2H, d, J=8.8 Hz), 8.55 (1H, d, J=5.2 Hz).

IR (KBr): 2960, 1680, 1545, 1493 cm$^{-1}$.

(iii) Production of N-{4-fluoro-4'-[1-hydroxy-1-(1H-imidazol-4-yl)-2-methylpropyl][1,1'-biphenyl]-3-yl}acetamide By the reaction in the same manner as in Example 4-(iii) using N-{4-fluoro-4'-[1-hydroxy-2-methyl-1-(1-trityl-1H-imidazol-4-yl)propyl][1,1'-biphenyl]-3-yl}acetamide (1.29 g) and pyridine hydrochloride (297 mg), the title compound (399 mg) was obtained as a colorless amorphous powder.

$^1$H-NMR (CDCl$_3$) δ: 0.81 (3H, d, J=6.8 Hz), 0.97 (3H, d, J=6.8 Hz), 2.23 (3H, s), 2.50–2.70 (1H, m), 6.95 (1H, s), 7.04–7.26 (2H, m), 7.38–7.60 (5H, m), 8.47 (1H, d, J=7.8 Hz).

IR (KBr): 2971, 1682, 1669, 1609, 1487 cm$^{-1}$.

Example 34

Production of N-{6-fluoro-4'-[1-hydroxy-1-(1H-imidazol-4-yl)-2-methylpropyl][1,1'-biphenyl]-3-yl}acetamide (i) Production of 2-bromo-1-fluoro-4-nitrobenzene To a mixture of 2-fluoro-5-nitroaniline (25.90 g), 47% aqueous hydrogen bromide (100 ml), water (200 ml) and acetic acid (200 ml) was added dropwise an aqueous sodium nitrite (11.56 g) solution (100 ml), and the mixture was stirred at 0° C. for 1 h. This mixture was added at 0° C. to a solution of copper bromide (CuBr: 27.30 g) dissolved in 47% aqueous hydrogen bromide (100 ml) and the mixture was stirred at room temperature for 16 h. The reaction mixture was extracted with ethyl acetate, dried (anhydrous magnesium sulfate) and concentrated under reduced pressure. The residue was purified by silica gel chomatography (eluent: hexane). Crystallization from hexane gave the title compound (4.01 g) as colorless needle crystals.

$^1$H-NMR (CDCl$_3$) δ: 7.22–7.35 (1H, m), 8.17-8.29 (1H, m), 8.51 (1H, dd, J=2.4, 6.0 Hz).

IR (KBr): 1537, 1470, 1348 cm$^{-1}$.

(ii) Production of N-(3-bromo-4-fluorophenyl)acetamide

By the reaction in the same manner as in Example 33-(i) using 2-bromo-1-fluoro-4-nitrobenzene (2.27 g), iron powder (2.90 g) and acetic anhydride (2.0 ml), the title compound (2.28 g) was obtained as colorless powder crystals.

$^1$H-NMR (CDCl$_3$) δ: 2.17 (3H, s) 7.06 (1H, t, J=8.4 Hz), 7.26–7.43 (2H, m), 7.80 (1H, dd, J=2.6, 5.6 Hz).

IR (KBr): 3306, 1669, 1609, 1549, 1493 cm$^{-1}$.

(iii) Production of N-{6-fluoro-4'-[1-hydroxy-2-methyl-1-(1-trityl-1H-imidazol-4-yl)propyl][1,1'-biphenyl]-3-yl}acetamide By the reaction in the same manner as in Example 33-(ii) using 4-[1-hydroxy-2-methyl-1-(1-trityl-1H-imidazol-4-yl)propyl]phenylboronic acid (3.19 g), N-(3-bromo-4-fluorophenyl)acetamide (990 mg) and tetrakis(triphenylphosphine)palladium(0) (0.21 g), the title compound (870 mg) was obtained as a pale-yellow amorphous powder.

$^1$H-NMR (CDCl$_3$) δ: 0.76 (3H, d, J=6.6 Hz), 0.93 (3H, d, J=6.6 Hz), 2.11 (3H, s), 2.30–2.58 (1H, m), 3.59 (1H, s), 6.79 (1H, d, J=1.0 Hz), 6.96–7.20 (7H, m), 7.25–7.70 (15H, m), 7.88 (1H, s).

IR (KBr): 3287, 2969, 1672, 1553, 1489 cm$^{-1}$.

(iv) Production of N-{6-fluoro-4'-[1-hydroxy-1-(1H-imidazol-4-yl)-2-methylpropyl][1,1'-biphenyl]-3-yl}acetamide By the reaction in the same manner as in Example 4-(iii) using N-{6-fluoro-4'-[1-hydroxy-2-methyl-1-(1-trityl-1H-imidazol-4-yl)propyl][1,1'-biphenyl]-3-yl}acetamide (820 mg) and pyridine hydrochloride (230 mg), the title compound (250 mg) was obtained as a colorless amorphous powder.

$^1$H-NMR (CDCl$_3$+CD$_3$OD) δ: 0.82 (3H, d, J=7.0 Hz), 0.98 (3H, d, J=7.0 Hz), 2.14 (3H, s), 2.56–2.70 (1H, m), 6.94–7.12 (2H, m), 7.40–7.58 (7H, m).

IR (KBr): 3158, 2973, 1667, 1489 cm$^{-1}$.

Example 35

Production of N-{4'-[1-hydroxy-1-(1H-imidazol-4-yl)-2-methylpropyl]-6-methoxy[1,1'-biphenyl]-3-yl}acetamide

(i) Production of N-(3-bromo-4-methoxyphenyl)acetamide

By the reaction in the same manner as in Example 33-(i) using 2-bromo-4-nitroanisole (5.41 g), iron powder (6.49 g) and acetic anhydride (4.4 ml), the title compound (4.87 g) was obtained as a colorless powder crystals.

$^1$H-NMR (CDCl$_3$) δ: 2.15 (3H, s), 3.87 (3H, s), 6.83 (1H, d, J=8.8 Hz), 7.32 (1H, brs), 7.43 (1H, dd, J=2.5, 8.8 Hz), 7.67 (1H, d, J=2.5 Hz).

IR (KBr): 3173, 1667, 1597, 1495 cm$^{-1}$.

(ii) Production of N-{4'-[1-hydroxy-2-methyl-1-(1-trityl-1H-imidazol-4-yl)propyl]-6-methoxy[1,1'-biphenyl]-3-yl}acetamide By the reaction in the same manner as in Example 33-(ii) using 4-[1-hydroxy-2-methyl-1-(1-trityl-1H-imidazol-4-yl)propyl]phenylboronic acid (3.21 g), N-(3-bromo-4-methoxyphenyl)acetamide (1.05 g) and tetrakis(triphenylphosphine)palladium(0) (0.16 g), the title compound (1.14 g) was obtained as a colorless amorphous powder.

$^1$H-NMR (CDCl$_3$+CD$_3$OD) δ: 0.77 (3H, d, J=6.6 Hz), 0.92 (3H, d, J=6.6 Hz), 2.14 (3H, s), 2.40–2.58 (1H, m), 3.77 (3H, s), 6.79 (1H, d, J=1.2 Hz), 6.92 (1H, d, J=8.8 Hz), 7.06–7.20 (6H, m), 7.24–7.62 (16H, m).

IR (KBr): 2971, 1663, 1549, 1493 cm$^{-1}$.

(iii) Production of N-{4'-[1-hydroxy-1-(1H-imidazol-4-yl)-2-methylpropyl]-6-methoxy[1,1'-biphenyl]-3-yl}acetamide By the reaction in the same manner as in Example 4-(iii) using N-{4'-[1-hydroxy-2-methyl-1-(1-trityl-1H-imidazol-4-yl)propyl]-6-methoxy[1,1'-biphenyl]-3-yl}acetamide (975 mg) and pyridine hydrochloride (299 mg), the title compound (290 mg) was obtained as a colorless amorphous powder.

$^1$H-NMR (CDCl$_3$) δ: 0.83 (3H, d, J=6.6 Hz), 0.98 (3H, d, J=6.6 Hz), 2.11 (3H, s), 2.40–2.70 (1H, m), 3.73 (3H, s), 6.87 (1H, d, J=8.4 Hz), 6.93 (1H, s), 7.24 (2H, s), 7.34 (2H, d, J=8.0 Hz), 7.41 (2H, d, J=8.0 Hz), 7.50 (1H, d, J=8.4 Hz).

IR (KBr): 3183, 2973, 1667, 1495 cm$^{-1}$.

Example 36

Production of N-[4'-[1-hydroxy-1-(-1H-imidazol-4-yl)-2-methylpropyl]-2-methyl[1,1'-biphenyl]-3-yl]acetamide

(i) Production of N-[4'-[1-hydroxy-2-methyl-1-(1-trityl-1H-imidazol-4-yl)propyl]-2-methyl[1,1'-biphenyl]-3-yl]acetamide By the reaction in the same manner as in Example 33-(ii) using N-(3-bromo-2-methyl)acetamide (1.19 g), a crude product (3.40 g) of 4-[1-hydroxy-2-methyl-1-(1-trityl-1H-imidazol-4-yl)propyl]phenylboronic acid, 2M aqueous sodium carbonate solution (5.20 ml) and tetrakis(triphenylphosphine)palladium(0) (301 mg), the colorless amorphous title compound (1.15 g) was obtained.

$^1$H-NMR (CDCl$_3$) δ: 0,78 (3H, d, J=6.6 Hz), 0.94 (3H, d, J=6.6 Hz), 2.14 (3H, s), 2.24 (3H, s), 2.41–2.48 (1H, m), 3.61 (1H, s), 6.77 (1H, d, J=1.4 Hz), 7.00–7.38 (20H, m), 7.50–7.54 (2H, m), 7.22 (2H, d, J=7.8 Hz).

IR (KBr): 1667, 1535, 1491, 1468, 1445, 910, 733, 702 cm$^{-1}$.

(ii) Production of N-[4'-[1-hydroxy-1-(-1H-imidazol-4-yl)-2-methylpropyl]-2-methyl[1,1'-biphenyl]-3-yl]acetamide By the reaction in the same manner as in Example 4-(iii) using N-[4'-[1-hydroxy-2-methyl-1-(1-trityl-1H-imidazol-4-yl)propyl]-2-methyl[1,1'-biphenyl]-3-yl]acetamide (1.10 g) and pyridine hydrochloride (378 mg), the colorless amorphous title compound (605 mg) was obtained.

$^1$H-NMR (CDCl$_3$+CD$_3$OD) δ: 0.81 (3H, d, J=7.0 Hz), 0.97 (3H, d, J=6.6 Hz), 2.05 (3H, s), 2.20 (3H, s), 2.59–2.63 (1H, m), 6.91 (1H, s), 7.03–7.19 (4H, m), 7.41–7.50 (4H, m).

IR (KBr): 1665, 1535, 1468, 1439, 1372, 997, 828, 793 cm$^{-1}$.

Example 37

Production of N-[4'-[1-hydroxy-1-(1H-imidazol-4-yl)-2-methylpropyl]-5-methyl[1,1'-biphenyl]-3-yl]acetamide

(i) Production of N-[4'-[1-hydroxy-2-methyl-1-(1-trityl-1H-imidazol-4-yl)propyl]-5-methyl[1,1'-biphenyl]-3-yl]acetamide By the reaction in the same manner as in Example 33-(ii) using N-(3-bromo-5-methylphenyl)acetamide (612 mg), a crude product (1.75 g) of 4-[1-hydroxy-2-methyl-1-(1-trityl-1H-imidazol-4-yl)propyl]phenylboronic acid, 2M aqueous sodium carbonate solution (2.68 ml) and tetrakis(triphenylphosphine)palladium(0) (310 mg), the colorless amorphous title compound (1.07 g) was obtained.

$^1$H-NMR (CDCl$_3$) δ: 0.76 (3H, d, J=6.6 Hz), 0.92 (3H, d, J=6.6 Hz), 2.18 (3H, s), 2.39–2.48 (4H, m), 3.56 (1H, s), 6.78 (1H, s), 7.13–7.15 (7H, m), 7.32–7.72 (17H, m).

IR (KBr): 1674, 1615, 1559, 1447, 1121, 747, 725, 700 cm$^{-1}$.

(ii) Production of N-[4'-[1-hydroxy-1-(1H-imidazol-4-yl)-2-methylpropyl]-5-methyl[1,1'-biphenyl]-3-yl]acetamide By the reaction in the same manner as in Example 4-(iii) using N-[4'-[1-hydroxy-2-methyl-1-(1-trityl-1H-imidazol-4-yl)propyl]-5-methyl[1,1'-biphenyl]-3-yl]acetamide (1.02 g) and pyridine hydrochloride (350 mg), the colorless amorphous title compound (410 mg) was obtained.

$^1$H-NMR (CDCl$_3$+CD$_3$OD) δ: 0.83 (3H, d, J=6.8 Hz), 0.98 (3H, d, J=7.0 Hz), 2.16 (3H, s), 2.37 (3H, s), 2.60–2.66 (1H, m), 6.96 (1H, s), 7.13 (1H, s), 7.37 (1H, s), 7.46–7.50 (6H, m).

IR (KBr): 1669, 1613, 1599, 1559, 1435, 1372, 822 cm$^{-1}$.

Example 38

Production of N-[4'-[1-hydroxy-1-(1H-imidazol-4-yl)-2-methylpropyl]-5-(trifluoromethyl)[1,1'-biphenyl]-3-yl]acetamide

(i) Production of N-[4'-[1-hydroxy-2-methyl-1-(1-trityl-1H-imidazol-4-yl)propyl]-5-(trifluoromethyl)[1,1'-biphenyl]-3-yl]acetamide By the reaction in the same manner as in Example 33-(ii) using N-[3-bromo-5-(trifluoromethyl)phenyl]acetamide (1.00 g), a crude product (2.50 g) of 4-[1-hydroxy-2-methyl-1-(1-trityl-1H-imidazol-4-yl)propyl]phenylboronic acid, 2M aqueous sodium carbonate solution (3.56 ml) and tetrakis(triphenylphosphine)palladium(0) (221 mg), the colorless amorphous title compound (1.80 g) was obtained.

$^1$H-NMR (CDCl$_3$) δ: 0.76 (3H, d, J=7.0 Hz), 0.93 (3H, d, J=6.6 Hz), 2.21 (3H, s), 2.42–2.49 (1H, m), 3.54 (1H, s), 6.79 (1H, d, J=1.2 Hz), 7.10–7.15 (6H, m), 7.32–7.36 (10H, m), 7.45–7.64 (6H, m), 7.77 (1H, s), 7.86 (1H, s).

IR (KBr): 1682, 1456, 1364, 1262, 1167, 1127, 747, 735, 702 cm$^{-1}$.

(ii) Production of N-[4'-[1-hydroxy-1-(1H-imidazol-4-yl)-2-methylpropyl]-5-(trifluoromethyl)[1,1'-biphenyl]-3-yl]acetamide By the reaction in the same manner as in Example 4-(iii) using N-[4'-[1-hydroxy-2-methyl-1-(1-trityl-1H-imidazol-4-yl)propyl]-5-(trifluoromethyl)[1,1'-biphenyl]-3-yl]acetamide (1.85 g) and pyridine hydrochloride (551 mg), the colorless amorphous title compound (591 mg) was obtained.

$^1$H-NMR (CDCl$_3$+CD$_3$OD) δ: 0.81 (3H, d, J=6.6 Hz), 0.99 (3H, d, J=6.6 Hz), 2.18 (3H, s), 2.50–2.62 (1H, m), 6.98 (1H, s), 7.44–7.58 (6H, m), 7.85 (2H, s).

IR (KBr): 1678, 1566, 1460, 1366, 1264, 1169, 1127, 824 cm$^{-1}$.

Example 39

Production of N-[4'-[1-hydroxy-(1H-imidazol-4-yl)ethyl][1,1'-biphenyl]-3-yl]acetamide (i) Production of (4-bromophenyl) (1-trityl-1H-imidazol-4-yl)methanol By the reaction in the same manner as in Example 4-(i) using p-dibromobenzene (54.7 g), a solution (1.6 M; 94.7 ml) of n-butyllithium in hexane and 1-trityl-1H-imidazole-4-carbaldehyde (34.2 g), the title compound (27.8 g) was obtained as colorless powder crystals.

$^1$H-NMR (CDCl$_3$) δ: 3.56 (1H, br s), 5.71 (2H, d, J=4.4 Hz), 6.58 (1H, s), 7.07–7.13 (7H, m), 7.25–7.44 (12H, m).

IR (KBr): 1493, 1445, 1128, 1011, 909, 747, 733, 702 cm$^{-1}$.

(ii) Production of (4-bromophenyl) (1-trityl-1H-imidazol-4-yl)methanone

By the reaction in the same manner as in Example 24-(iii) using (4-bromophenyl)(1-trityl-1H-imidazol-4-yl)methanol (30.0 g) and manganese dioxide (52.6 g), the title compound (23.3 g) was obtained as colorless powder crystals.

$^1$H-NMR (CDCl$_3$) δ: 7.10–7.19 (6H, m), 7.31–7.41 (9H, m), 7.52 (1H, d, J=1.4 Hz), 7.68 (2H, d, J=8.4 Hz), 7.77 (1H, d, J=1.4 Hz), 8.21 (2H, d, J=8.4 Hz).

IR (KBr): 1644, 1520, 1213, 887, 756, 747, 702 cm$^{-1}$.

(iii) Production of N-[4'-[(1-trityl-1H-imidazol-4-yl)carbonyl][1,1'-biphenyl]-3-yl]acetamide By the reaction in the same manner as in Example 29-(i) using (4-bromophenyl)(1-trityl-1H-imidazol-4-yl)methanone (12.0 g), 3-acetamidebenzeneboronic acid (5.66 g), 2M aqueous sodium carbonate solution (24.3 ml) and tetrakis(triphenylphosphine)palladium(0) (842 mg), the title compound (10.1 g) was obtained as colorless powder crystals.

$^1$H-NMR (CDCl$_3$) δ: 2.20 (3H, s), 7.14–7.21 (6H, m), 7.36–7.44 (12H, m), 7.54–7.77 (6H, m), 8.33 (2H, d, J=8.4 Hz).

IR (KBr): 1671. 1645. 1603. 1553. 1524. 756. 702 cm$^{-1}$.

(iv) Production of N-[4'-[1-hydroxy-1-(1-trityl-1H-imidazol-4-yl)ethyl][1,1'-biphenyl]-3-yl]acetamide To a solution of N-[4'-[(1-trityl-1H-imidazol-4-yl)carbonyl][1,1'-biphenyl]-3-yl]acetamide (800 mg) in THF (14 ml) was added dropwise a solution (1.0 M; 4.38 ml) of methylmagnesium bromide in THF at 0° C., and the mixture was stirred at 0° C. for 20 min. Saturated ammonium chloride was added to the reaction mixture and the mixture was extracted with ethyl acetate, washed with saturated brine and dried over anhydrous magnesium sulfate. The solvent was evaporated under reduced pressure and the residue was recrystallized from ethyl acetate-methanol-hexane to give the title compound (823 mg) as colorless powder crystals.

$^1$H-NMR (CDCl$_3$) δ: 1.81 (3H, s), 2.20 (3H, s), 3.37 (1H, s), 6.79 (1H, d, J=1.4 Hz), 7.12–7.20 (8H, m), 7.31–7.52 (16H, m), 7.65 (1H, br s).

IR (KBr): 1672, 1553, 1483, 1445, 909, 747, 733, 700 cm$^{-1}$.

(v) Production of N-[4'-[1-hydroxy-(1H-imidazol-4-yl)ethyl][1,1'-biphenyl]-3-yl]acetamide By the reaction in the same manner as in Example 4-(iii) using N-[4'-[1-hydroxy-1-(1-trityl-1H-imidazol-4-yl)ethyl][1,1'-biphenyl]-3-yl]acetamide (775 mg) and pyridine hydrochloride (286 mg), the colorless amorphous title compound (262 mg) was obtained.

$^1$H-NMR (CDCl$_3$+CD$_3$OD) δ: 1.89 (3H, s), 2.16 (3H, s), 6.89 (1H, s), 7.27–7.52 (8H, m), 7.69 (1H, s).

IR (KBr): 3031, 1672, 1609, 1591, 1559, 1483, 1397, 1312, 791 cm$^{-1}$.

Example 40

Production of N-[4'-[cyclopropyl(hydroxy)(1H-imidazol-4-yl)methyl][1,1'-biphenyl]-3-yl]acetamide (i) Production of N-[4'-[cyclopropyl(hydroxy)(1-trityl-1H-imidazol-4-yl)methyl][1,1'-biphenyl]-3-yl]acetamide By the reaction in the same manner as in Example 39-(iv) using N-[4'-[(1-trityl-1H-imidazol-4-yl)carbonyl][1,1'-biphenyl]-3-yl]acetamide (1.50 g) and a solution (1.0 M; 9.59 ml) of cyclopropylmagnesium bromide in THF, the title compound (996 mg) was obtained as colorless powder crystals.

1H-NMR (CDCl$_3$) δ: 0.41–0.49 (4H, m), 1.47–1.55 (1H, m), 2.20 (3H, s), 3.26 (1H, s), 6.82 (1H, d, J=1.4 Hz), 7.11–7.41 (19H, m), 7.50–7.53 (5H, m), 7.65 (1H, s).

IR (KBr): 1671, 1591, 1559, 1483, 1445, 731, 702 cm$^{-1}$.

(ii) N-[4'-[cyclopropyl(hydroxy) (1H-imidazol-4-yl)methyl][1,1'-biphenyl]-3-yl]acetamide By the reaction in the same manner as in Example 4-(iii) using N-[4'-[cyclopropyl(hydroxy)(1-trityl-1H-imidazol-4-yl)methyl][1,1'-biphenyl]-3-yl]acetamide (946 mg) and pyridine hydrochloride (334 mg), the colorless amorphous title compound (216 mg) was obtained.

$^1$H-NMR (CDCl$_3$+CD$_3$OD) δ: 0.47–0.60 (4H, m), 1.57–1.64 (1H, m), 2.17 (3H, s), 7.00 (1H, s), 7.36–7.58 (8H, m), 7.71 (1H, s).

IR (KBr): 3148, 1667, 1591, 1555, 1485, 831, 791 cm$^{-1}$.

Example 41

Production of N-[4'-[1-hydroxy-1-(1H-imidazol-4-yl)butyl][1,1'-biphenyl]-3-yl]acetamide (i) Production of N-[4'-[1-hydroxy-1-(1-trityl-1H-imidazol-4yl)-3-butenyl][1,1'-biphenyl]-3-yl]acetamide By the reaction in the same manner as in Example 39-(iv) using N-[4'-[(1-trityl-1H-imidazol-4-yl)carbonyl][1,1'-biphenyl]-3-yl]acetamide (1.00 g) and a solution (1.0 M; 5.48 ml) of allylmagnesium bromide in THF, the colorless amorphous title compound (909 mg) was obtained.

1H-NMR (CDCl$_3$) δ: 2.19 (3H, s), 2.85 (1H, dd, J=6.2, 14.0 Hz), 3.01 (1H, dd, J=7.6, 14.0 Hz), 3.34 (1H, s), 5.04–5.11 (2H, m), 5.62–5.79 (1H, m), 6.78 (1H, d, J=1.6 Hz), 7.11–7.18 (6H, m), 7.32–7.51 (18H, m), 7.65 (1H, s).

IR (KBr): 1669, 1609, 1593, 1485, 1445, 909, 747, 733, 702 cm$^{-1}$.

(ii) Production of N-[4'-[1-hydroxy-1-(1H-imidazol-4-yl)butyl][1,1'-biphenyl]-3-yl]acetamide A suspension of N-[4'-[1-hydroxy-1-(1-trityl-1H-imidazol-4-yl)-3-butenyl][1,1'-biphenyl]-3-yl]acetamide (829 mg), 10% palladium carbon (829 mg) and 1N hydrochloric acid (1.41 ml) in ethanol (14 ml) was stirred under a hydrogen atmosphere at room temperature for 9.5 h. Sodium hydrogen carbonate (130 mg) was added and the mixture was stirred. The reaction mixture was filtered through Celite, and the filtrate was concentrated. The residue was purified by silica gel chomatography (eluent;chloroform→chloroform:methanol= 10:1→7:1→4:1) to give the colorless amorphous title compound (420 mg).

$^1$H-NMR (CDCl$_3$+CD$_3$OD) δ: 0.90 (3H, t, J=7.0 Hz), 1.22–1.38 (2H, m), 2.16–2.36 (5H, m), 6.89 (1H, s), 7.29–7.56 (8H, m), 7.71 (1H, s).

IR (KBr): 3144, 1659, 1609, 1557, 1485, 1435, 791 cm$^{-1}$.

Example 42

Production of N-[4'-[1-hydroxy-1-(1H-imidazol-4-yl)propyl][1,1'-biphenyl]-3-yl]acetamide (i) Production of N-[4'-[1-hydroxy-1-(1-trityl-1H-imidazol-4-yl)propyl][1,1'-biphenyl]-3-yl]acetamide By the reaction in the same manner as in Example 39-(iv) using N-[4'-[(1-trityl-1H-imidazol-4-yl)carbonyl][1,1'-biphenyl]-3-yl]acetamide (1.50 g) and a solution (3.0 M; 2.74 ml) of ethylmagnesium bromide in diethyl ether, the pale-yellow amorphous title compound (1.36 g) was obtained.

$^1$H-NMR (CDCl$_3$) δ: 0.86 (3H, t, J=7.6 Hz), 2.12–2.20 (5H, m) 3.35 (1H, s), 6.67 (1H, s), 7.13–7.22 (6H, m), 7.26–7.48 (18H, m), 7.66 (1H, s).

IR (KBr): 1674, 1609, 1557, 1485, 1445, 747, 733, 702 cm$^{-1}$.

(ii) Production of N-[4'-[1-hydroxy-1-(1H-imidazol-4yl)propyl][1,1'-biphenyl]-3-yl]acetamide By the reaction in the same manner as in Example 41-(ii) using N-[4'-[1-hydroxy-1-(1-trityl-1H-imidazol-4-yl) propyl][1,1'-biphenyl]-3-yl]acetamide (1.31 g), 10% palladium carbon (1.31 g) and 1N hydrochloric acid (2.27 ml), the colorless amorphous title compound (640 mg) was obtained.

$^1$H-NMR (CDCl$_3$+CD$_3$OD) δ: 0.89 (3H, t, J=7.6 Hz), 2.17–2.32 (5H, m), 6.91 (1H, s), 7.30–7.53 (8H, m), 7.69 (1H, s).

IR (KBr): 3148, 1667, 1609, 1591, 1557, 1485, 831, 791 cm$^{-1}$.

Example 43

Production of N-{4'-[1-hydroxy-1-(1H-imidazol-4-yl)-2-methylpropyl][1,1'-biphenyl]-3-yl}propanamide (i) Production of N-(3-bromophenyl)propanamide To a solution of 3-bromoaniline (5.10 g) and triethylamine (8.3 ml) in THF (40 ml) was added dropwise propionyl chloride (2.8 ml) at 0° C. and the mixture was stirred at 0° C. for 2 h. Water and ethyl acetate were added to the reaction mixture and the organic layer was separated. The organic layer was washed with water and brine, dried (magnesium sulfate) and concentrated under reduced pressure. The residue was recrystallized from hexane-ethyl acetate to give the title compound (5.60 g) as colorless needle crystals.

$^1$H-NMR (CDCl$_3$) δ: 1.24 (3H, t, J=7.5 Hz), 2.39 (2H, q, J=7.5 Hz), 7.11–7.30 (3H, m), 7.41 (1H, d, J=7.8 Hz), 7.79 (1H, brs).

IR (KBr): 3243, 1661, 1593, 1539 cm$^{-1}$.

(ii) Production of N-{4'-[1-hydroxy-2-methyl-1-(1-trityl-1H-imidazol-4-yl)propyl][1,1'-biphenyl]-3-yl}propanamide By the reaction in the same manner as in Example 33-(ii) using 4-[1-hydroxy-2-methyl-1-(1-trityl-1H-imidazol-4-yl) propyl]phenylboronic acid (3.12 g), N-(3-bromophenyl) propanamide (1.56 g) and tetrakis(triphenylphosphine) palladium(0) (0.133 g), the title compound (1.26 g) was obtained as a colorless amorphous powder.

$^1$H-NMR (CDCl$_3$) δ: 0.76 (3H, d, J=6.6 Hz), 0.92 (3H, d, J=6.6 Hz), 1.25 (3H, t, J=7.5 Hz), 2.30–2.50 (3H, m), 3.55 (1H, s), 6.78 (1H, s), 7.08–7.44 (20H, m), 7.48 (2H, d, J=8.3 Hz), 7.54 (2H, d, J=8.3 Hz), 7.72 (1H, brs).

IR (KBr): 2973, 1669, 1557, 1485 cm$^{-1}$.

(iii) Production of N-{4'-[1-hydroxy-1-(1H-imidazol-4-yl)-2-methylpropyl][1,1'-biphenyl]-3-yl}propanamide By the reaction in the same manner as in Example 4-(iii) using N-{4'-[1-hydroxy-2-methyl-1-(1-trityl-1H-imidazol-4-yl)propyl][1,1'-biphenyl]-3-yl}propanamide (1.46 g) and pyridine hydrochloride (440 mg), the title compound (280 mg) was obtained as a colorless amorphous powder.

$^1$H-NMR (CDCl$_3$+CD$_3$OD) δ: 0.79 (3H, d, J=7.0 Hz), 0.96 (3H, d, J=7.0 Hz), 1.22 (3H, t, J=7.4 Hz), 2.39 (2H, q, J=7.4 Hz), 2.40–2.70 (1H, m), 6.91 (1H, d, J=1.2 Hz), 7.24–7.55 (8H, m), 7.67 (1H, s).

IR (KBr): 3196, 2975, 1669, 1557 cm$^{-1}$.

Example 44

Production of N-[4'-[1-hydroxy-1-(1H-imidazol-4-yl)-3methylbutyl][1,1'-biphenyl]-3-yl]acetamide (i) Production of N-[4'-[1-hydroxy-3-methyl-1-(1-trityl-1H-imidazol-4-yl)butyl][1,1'-biphenyl]-3-yl]acetamide By the reaction in the same manner as in Example 39-(iv) using N-[4'-[(1-trityl-1H-imidazol-4-yl)carbonyl][1,1'- biphenyl]-3-yl]acetamide (1.26 g) and a solution (1.0 M; 8.05 ml) of isobutylmagnesium bromide in THF, the pale-yellow amorphous title compound (408 mg) was obtained.

¹H-NMR (CDCl₃) δ: 0.77 (3H, d, J=6.8 Hz), 0.88 (3H, d, J=6.6 Hz), 1.68–1.74 (1H, m), 2.02 (2H, d, J=5.2 Hz), 2.20 (3H, s), 3.43 (1H, s), 6.74 (1H, s), 7.12–7.17 (8H, m), 7.32–7.48 (16H, m), 7.65 (1H, s).

IR (KBr): 1672, 1607, 1557, 1485, 1445, 909, 747, 733, 702 cm⁻¹.

(ii) Production of N-[4'-[1-hydroxy-1-(1H-imidazol-4-yl)-3-ethylbutyl][1,1'-biphenyl]-3-yl]acetamide By the reaction in the same manner as in Example 41-(ii) using N-[4'-[1-hydroxy-3-methyl-1-(1-trityl-1H-imidazol-4-yl)butyl][1,1'-biphenyl]-3-yl]acetamide (1.31 g), 10% palladium carbon (386 mg) and 1N hydrochloric acid (0.637 ml), the colorless amorphous title compound (141 mg) was obtained.

¹H-NMR (CDCl₃+CD₃OD) δ: 0.75 (3H, d, J=6.6 Hz), 0.93 (3H, d, J=6.6 Hz), 1.66–1.78 (1H, m), 2.13–2.16 (5H, m), 6.86 (1H, s), 7.30–7.53 (8H, m), 7.68 (1H, s).

IR (KBr): 1669, 1559, 1483, 1435, 1395, 1372, 791 cm⁻¹.

Example 45

Production of 3'-[1-hydroxy-1-(1H-imidazol-4-yl)-2-methylpropyl]-N-methyl[1,1'-biphenyl]-3-carboxamide (i) Production of 3-bromophenylcarboxamide To a solution of 3-bromobenzoyl chloride (21.75 g) in THF (20 ml) was added a 40% solution (50 ml) of methylamine in methanol at 0° C. and the mixture was stirred at 0° C. for 1 h. The solvent was evaporated under reduced pressure, and the residue was dissolved in ethyl acetate, the mixture was washed with water and brine, dried (magnesium sulfate) and concentrated under reduced pressure. The residue was recrystallized from ethyl acetate-hexane to give the title compound (18.6 g) as colorless powder crystals.

¹H-NMR (CDCl₃) δ: 2.99 (3H, d, J=5.0 Hz), 6.55 (1H, brs), 7.28 (1H, t, J=7.9 Hz), 7.56–7.72 (2H, m), 7.91 (1H, t, J=1.8 Hz).

IR (KBr): 3304, 1640, 1557 cm⁻¹.

(ii) Production of 3'-[1-hydroxy-2-methyl-1-(1-trityl-1H-imidazol-4-yl)propyl]-N-methyl[1,1'-biphenyl]-3-carboxamide By the reaction in the same manner as in Example 33-(ii) using 3-[1-hydroxy-2-methyl-1-(1-trityl-1H-imidazol-4-yl)propyl]phenylboronic acid (1.01 g), 3-bromophenylcarboxamide (567 mg) and tetrakis(triphenylphosphine)palladium(0) (0.33 g), the title compound (435 mg) was obtained as colorless powder crystals.

¹H-NMR (CDCl₃) δ: 0.76 (3H, d, J=6.6 Hz), 0.94 (3H, d, J=6.6 Hz), 2.36–2.58 (1H, m), 3.03 (3H, d, J=4.6 Hz), 3.66 (1H, s), 6.23 (1H, brs), 6.78 (1H, d, J=1.2 Hz), 7.06–7.17 (6H, m), 7.23–7.54 (14H, m), 7.62–7.80 (3H, m), 7.88–7.93 (1H, m).

IR (KBr): 3378, 2969, 1644, 1549, 1447 cm⁻¹.

(iii) Production of 3'-[1-hydroxy-1-(1H-imidazol-4-yl)-2-methylpropyl]-N-methyl[1,1'-biphenyl]-3-carboxamide By the reaction in the same manner as in Example 4-(iii) using 3'-(1-hydroxy-2-methyl-1-(1-trityl-1H-imidazol-4-yl)propyl]-N-methyl[1,1'-biphenyl]-3-carboxamide (576 mg) and pyridine hydrochloride (0.22 g), the title compound (55 mg) was obtained as colorless powder crystals.

¹H-NMR (CDCl₃+CD₃OD) δ: 0.81 (3H, d, J=6.6 Hz), 0.97 (3H, d, J=6.6 Hz), 2.60–2.84 (1H, m), 3.02 (3H, s), 7.00 (1H, d, J=1.0 Hz), 7.30–7.55 (5H, m), 7.67–7.90 (3H, m), 8.01 (1H, t, J=1.5 Hz).

IR (KBr): 2967, 2872, 1644, 1541 cm⁻¹.

Example 46

Production of 4'-(1-hydroxy-1-(1H-imidazol-4-yl)-2-methylpropyl]-N-methyl[1,1'-biphenyl]-3-carboxamide (i) 4'-[1-hydroxy-2-methyl-1-(1-trityl-1H-imidazol-4-yl)propyl]-N-methyl[1,1'-biphenyl]-3-carboxamide.

By the reaction in the same manner as in Example 33-(ii) using 4-[1-hydroxy-2-methyl-1-(1-trityl-1H-imidazol-4-yl)propyl]phenylboronic acid (3.44 g), 3-bromo-N-methylbenzamide (1.10 g) and tetrakis(triphenylphosphine)palladium(0) (0.21 g), the title compound (1.00 g) was obtained as a pale-yellow amorphous powder.

¹H-NMR (CDCl₃) δ: 0.76 (3H, d, J=6.7 Hz), 0.93 (3H, d, J=6.7 Hz), 2.30–2.54 (1H, m), 3.02 (3H, d, J=4.8 Hz), 3.58 (1H, s), 6.33 (1H, brs), 6.78 (1H, d, J=1.4 Hz), 7.04–7.20 (6H, m), 7.22–7.38 (9H, m), 7.39–7.76 (8H, m), 7.98 (1H, t, J=1.4 Hz).

IR (KBr): 3295, 2969, 1644, 1549, 1121 cm⁻¹.

(ii) Production of 4'-[1-hydroxy-1-(1H-imidazol-4-yl)-2-methylpropyl]-N-methyl[1,1'-biphenyl]-3-carboxamide By the reaction in the same manner as in Example 4-(iii) using 4'-[1-hydroxy-2-methyl-1-(1-trityl-1H-imidazol-4-yl)propyl]-N-methyl[1,1'-biphenyl]-3-carboxamide (850 mg) and pyridine hydrochloride (270 mg), the title compound (210 mg) was obtained as a colorless amorphous powder.

¹H-NMR (CDCl₃+CD₃OD) δ: 0.81 (3H, d, J=6.9 Hz), 0.98 (3H, d, J=6.9 Hz), 2.40–2.80 (1H, m), 3.00 (3H, s), 6.96 (1H, s), 7.30 (1H, d, J=1.4 Hz), 7.30–7.60 (5H, m), 7.60–7.74 (2H, m), 7.93 (1H, s).

IR (KBr): 3277, 2969, 1645, 1547 cm⁻¹.

Example 47

Production of N-ethyl-4'-[1-hydroxy-1-(1H-imidazol-4-yl)-2-methylpropyl][1,1'-biphenyl]-3-carboxamide (i) Production of 3-bromo-N-ethylbenzamide To a solution of sodium hydroxide (3.80 g) in methanol (50 ml)—water (15 ml) was added by portions ethylamine hydrochloride (7.80 g) at 0° C. and the mixture was stirred for 5 min. 3-Bromobenzoyl chloride (5.53 g) was added dropwise and the mixture was stirrd at room temperature for 1 h. Methanol was evaporated under reduced pressure, and ethyl acetate was added to the residue for partitioning. The organic layer was washed with water and brine, dried (magnesium sulfate) and concentrated under reduced pressure. The residue was recrystallized from hexane-ethyl acetate to give the title compound (5.47 g) as colorless powder crystals.

¹H-NMR (CDCl₃) δ: 1.26 (3H, t, J=7.1 Hz), 3.40–3.59 (2H, m), 6.11 (1H, brs), 7.30 (1H, t, J=8.2 Hz), 7.57–7.72 (2H, m), 7.90 (1H, t, J=1.4 Hz).

IR (KBr): 3308, 1638, 1541 cm⁻¹.

(ii) N-ethyl-4'-[1-hydroxy-2-methyl-1-(1-trityl-1H-imidazol-4-yl)propyl][1,1'-biphenyl]-3-carboxamide By the reaction in the same manner as in Example 33-(ii) using 4-[1-hydroxy-2-methyl-1-(1-trityl-1H-imidazol-4-yl)propyl]phenylboronic acid (7.40 g, 14.7 mmol), 3-bromo-N-ethylbenzamide (2.20 g) and tetrakis(triphenylphosphine)palladium(0) (0.441 g), the title compound (2.56 g) was obtained as a yellow amorphous powder.

$^1$H-NMR (CDCl$_3$) δ: 0.76 (3H, d, J=6.8 Hz), 0.93 (3H, d, J=6.8 Hz), 1.27 (3H, t, J=7.2 Hz), 2.36–2.54 (1H, m), 3.42–3.61 (3H, m), 6.15 (1H, brs), 6.78 (1H, d, J=1.6 Hz), 7.06–7.18 (6H, m), 7.27–7.38 (9H, m), 7.40–7.75 (8H, m), 7.97 (1H, t, J=1.6 Hz).

IR (KBr): 3295, 2971, 1644, 1537 cm$^{-1}$.

(iii) Production of N-ethyl-4'-[1-hydroxy-1-(1H-imidazol-4-yl)-2-methylpropyl][1,1'-biphenyl]-3-carboxamide By the reaction in the same manner as in Example 4-(iii) using N-ethyl-4'-[1-hydroxy-2-methyl-1-(1-trityl-1H-imidazol-4-yl)propyl][1,1'-biphenyl]-3-carboxamide (4.00 g) and pyridine hydrochloride (1.14 g), the title compound (664 mg) was obtained as a colorless amorphous powder.

$^1$H-NMR (CDCl$_3$+CD$_3$OD) δ: 0.79 (3H, d, J=6.7 Hz), 0.96 (3H, d, J=6.7 Hz), 1.23 (3H, t, J=7.1 Hz), 2.48–2.70 (1H, m), 3.36–3.56 (2H, m), 6.92 (1H, d, J=1.2 Hz), 7.09 (1H, t, J=5.5 Hz), 7.35–7.56 (6H, m), 7.58–7.72 (2H, m), 7.92 (1H, t, J=1.6 Hz).

IR (KBr): 2973, 1644, 1537 cm$^{-1}$.

Example 48

Production of 4'-[1-hydroxy-1-(1H-imidazol-4-yl)-2-methylpropyl]-N-isopropyl[1,1'-biphenyl]-3-carboxamide (i) Production of 3-bromo-N-isopropylbenzamide By the reaction in the same manner as in Example 45-(i) using 3-bromobenzoyl chloride (5.70 g) and isopropylamine (4.10 g), the title compound (5.75 g) was obtained as colorless powder crystals.

$^1$H-NMR (CDCl$_3$) δ: 1.26 (6H, d, J=6.6 Hz), 4.18–4.40 (1H, m), 5.97 (1H, brs), 7.23–7.34 (1H, m), 7.55–7.71 (2H, m), 7.84–7.90 (1H, m).

IR (KBr): 3241, 2973, 1634, 1545 cm$^{-1}$.

(ii) Production of 4'-[1-hydroxy-2-methyl-1-(1-trityl-1H-imidazol-4-yl)propyl]-N-isopropyl[1,1'-biphenyl]-3-carboxamide By the reaction in the same manner as in Example 33-(ii) using 4-[1-hydroxy-2-methyl-1-(1-trityl-1H-imidazol-4-yl)propyl]phenylboronic acid (3.40 g), 3-bromo-N-isopropylbenzamide (1.70 g) and tetrakis(triphenylphosphine)palladium(0) (0.220 g), the title compound (1.88 g) was obtained as a colorless amorphous powder.

$^1$H-NMR (CDCl$_3$) δ: 0.77 (3H, d, J=6.4 Hz), 0.93 (3H, d, J=6.4 Hz), 1.28 (6H, d, J=6.6 Hz), 2.36–2.58 (1H, m), 3.56 (1H, s), 4.20–4.44 (1H, m), 5.95 (1H, d, J=7.0 Hz), 6.78 (1H, d, J=1.4 Hz), 7.06–7.20 (6H, m), 7.26–7.38 (10H, m), 7.42–7.74 (7H, m), 7.95 (1H, t, J=1.6 Hz).

IR (KBr): 2971, 1636, 1537 cm$^{-1}$.

(iii) Production of 4'-[1-hydroxy-1-(1H-imidazol-4-yl)-2-methylpropyl]-N-isopropyl[1,1'-biphenyl]-3-carboxamide By the reaction in the same manner as in Example 4-(iii) using 4'-[1-hydroxy-2-methyl-1-(1-trityl-1H-imidazol-4-yl)propyl]-N-isopropyl[1,1'-biphenyl]-3-carboxamide (1.67 g) and pyridine hydrochloride (490 mg), the title compound (480 mg) was obtained as colorless powder crystals.

$^1$H-NMR (DMSO-d$_6$) δ: 0.60–1.00 (6H, m), 1.19 (6H, d, J=6.6 Hz), 2.54–2.78 (1H, m), 4.00–4.26 (1H, m), 7.42–7.68 (4H, m), 7.68–7.88 (4H, m), 8.08 (1H, s), 8.24–8.40 (1H, m), 11.80 (1H, brs).

IR (KBr): 3243, 2975, 1628, 1547 cm$^{-1}$.

Example 49

Production of N-cyclopropyl-4'-[1-hydroxy-1-(1H-imidazol-4-yl)-2-methylpropyl][1,1'-biphenyl]-3-carboxamide (i) Production of 3-bromo-N-cyclopropylbenzamide By the reaction in the same manner as in Example 45-(i) using 3-bromobenzoyl chloride (5.50 g) and cyclopropylamine (4.30 g), the title compound (5.20 g) was obtained as colorless needle crystals.

$^1$H-NMR (CDCl$_3$) δ: 0.56–0.68 (2H, m), 0.82–0.96 (2H, m), 2.80–2.98 (1H, m), 6.20 (1H, brs), 7.30 (1H, t, J=8.0 Hz), 7.58–7.70 (2H, m), 7.87 (1H, t, J=1.9 Hz).

IR (KBr): 3283, 1638, 1563, 1537 cm$^{-1}$.

(ii) Production of N-cyclopropyl-4'-[1-hydroxy-2-methyl-1-(1-trityl-1H-imidazol-4-yl)propyl][1,1'-biphenyl]-3-carboxamide By the reaction in the same manner as in Example 33-(ii) using 4-[1-hydroxy-2-methyl-1-(1-trityl-1H-imidazol-4-yl)propyl]phenylboronic acid (3.40 g), 3-bromo-N-cyclopropylbenzamide (1.53 g) and tetrakis(triphenylphosphine)palladium(0) (0.290 g), the title compound (1.84 g) was obtained as a pale-yellow amorphous powder.

$^1$H-NMR (CDCl$_3$) δ: 0.58–0.74 (2H, m), 0.76 (3H, d, J=6.8 Hz), 0.83–0.98 (5H, m), 2.35–2.60 (1H, m), 2.81–3.01 (1H, m), 3.56 (1H, s), 6.31 (1H, brs), 6.78 (1H, d, J=1.4 Hz), 7.04–7.18 (6H, m), 7.26–7.38 (9H, m), 7.39–7.74 (8H, m), 7.93 (1H, t, J=1.8 Hz).

IR (KBr): 3270, 2969, 1644, 1532 cm$^{-1}$.

(iii) Production of N-cyclopropyl-4'-[1-hydroxy-1-(1H-imidazol-4-yl)-2-methylpropyl][1,1'-biphenyl]-3-carboxamide By the reaction in the same manner as in Example 4-(iii) using N-cyclopropyl-4'-[1-hydroxy-2-methyl-1-(1-trityl-1H-imidazol-4-yl)propyl][1,1'-biphenyl]-3-carboxamide (2.13 g) and pyridine hydrochloride (650 mg), the title compound (375 mg) was obtained as colorless powder crystals.

$^1$H-NMR (CDCl$_3$+CD$_3$OD) δ: 0.56–0.90 (7H, m), 0.96 (3H, d, J=6.6 Hz), 2.44–2.70 (1H, m), 2.78–2.96 (1H, m), 6.92 (1H, s), 7.00 (1H, brs), 7.31–7.57 (6H, m), 7.58–7.74 (2H, m), 7.89 (1H, s).

IR (KBr): 3183, 2969, 1645, 1532 cm$^{-1}$.

Example 50

Production of 4'-[1-hydroxy-1-(1H-imidazol-4-yl)-2-methylpropyl]-6-methoxy-N-methyl[1,1'-biphenyl]-3-carboxamide (i) Production of 4'-[1-hydroxy-2-methyl-1-(1-trityl-1H-imidazol-4-yl)propyl]-6-methoxy-N-methyl[1,1'-biphenyl]-3-carboxamide By the reaction in the same manner as in Example 33-(ii) using 3-bromo-4-methoxy-N-methylbenzamide (934 mg), a crude product (2.50 g) of 4-[1-hydroxy-2-methyl-1-(1-trityl-1H-imidazol-4-yl)propyl]phenylboronic acid, 2M aqueous sodium carbonate solution (3.83 ml) and tetrakis (triphenylphosphine)palladium(0) (221 mg), the colorless amorphous title compound (1.45 g) was obtained.

$^1$H-NMR (CDCl$_3$) δ: 0.78 (3H, d, J=7.0 Hz), 0.93 (3H, d, J=7.0 Hz), 2.42–2.49 (1H, m), 3.00 (3H, d, J=4.8 Hz), 3.56 (3H, s), 3.85 (3H, s), 6.10 (1H, br s), 6.78 (1H, d, J=1.0 Hz), 6.99 (1H, d, J=8.4 Hz), 7.13–7.16 (5H, m), 7.32–7.80 (15H, m).

IR (KBr): 1645, 1491, 1464, 1258, 1182, 747, 733, 702 cm$^{-1}$.

(ii) Production of 4'-[1-hydroxy-1-(1H-imidazol-4-yl)-2-methylpropyl]-6-methoxy-N-methyl[1,1'-biphenyl]-3-carboxamide By the reaction in the same manner as in Example 4-(iii) using 4'-[1-hydroxy-2-methyl-1-(1-trityl-1H-imidazol-4-yl)propyl]-6-methoxy-N-methyl[1,1'-biphenyl]-3-carboxamide (1.40 g) and pyridine hydrochloride (468 mg), the colorless amorphous title compound (576 mg) was obtained.

$^1$H-NMR (CDCl$_3$+CD$_3$OD) δ: 0.85 (3H, d, J=6.6 Hz), 0.98 (3H, d, J=7.0 Hz), 2.58–2.71 (1H, m), 2.96 (3H, d, J=4.4 Hz), 3.83 (3H, s), 6.96–7.00 (3H, m), 7.41–7.54 (5H, m), 7.68 (1H, d, J=2.6 Hz), 7.77 (1H, dd, J=2.6, 8.4 Hz).

IR (KBr): 1626, 1603, 1556, 1493, 1262, 1020, 829, 631 cm$^{-1}$.

Example 51

Production of 6-fluoro-4'-[1-hydroxy-1-(1H-imidazol-4-yl)-2-methylpropyl]-N-methyl[1,1'-biphenyl]-3-carboxamide (i) Production of 6-fluoro-4'-[1-hydroxy-2-methyl-1-(1-trityl-1H-imidazol-4-yl)propyl]-N-methyl[1,1'-biphenyl]-3-carboxamide By the reaction in the same manner as in Example 33-(ii) using 3-bromo-4-fluoro-N-methylbenzamide (889 mg), a crude product (2.50 g) of 4-[1-hydroxy-2-methyl-1-(1-trityl-1H-imidazol-4-yl)propyl]phenylboronic acid, 2M aqueous sodium carbonate solution (3.83 ml) and tetrakis (triphenylphosphine)palladium(0) (221 mg), the colorless amorphous title compound (1.69 g) was obtained.

$^1$H-NMR (CDCl$_3$) δ: 0.77 (3H, d, J=6.6 Hz), 0.93 (3H, d, J=7.0 Hz), 2.42–2.49 (1H, m), 3.02 (3H, d, J=4.8 Hz), 3.58 (1H, s), 6.13 (1H, br s), 6.78 (1H, d, J=1.4 Hz), 7.11–7.23 (7H, m), 7.31–7.35 (9H, m), 7.46–7.72 (7H, m), 7.85 (1H, dd, J=2.4, 7.2 Hz).

IR (KBr): 1647, 1487, 1447, 909, 747, 733, 702 cm$^{-1}$.

(ii) Production of 6-fluoro-4'-[1-hydroxy-1-(1H-imidazol-4-yl)-2-methylpropyl]-N-methyl[1,1'-biphenyl]-3-carboxamide By the reaction in the same manner as in Example 4-(iii) using 6-fluoro-4'-[1-hydroxy-2-methyl-1-(1-trityl-1H-imidazol-4-yl)propyl]-N-methyl[1,1'-biphenyl]-3-carboxamide (1.64 g) and pyridine hydrochloride (559 mg), the colorless amorphous title compound (535 mg) was obtained.

$^1$H-NMR (CDCl$_3$+CD$_3$OD) δ: 0.83 (3H, d, J=7.0 Hz), 0.99 (3H, d, J=6.0 Hz), 2.67 (1H, br s), 2.97 (3H, s), 6.98 (1H, s), 7.17 (1H, dd, J=8.8, 8.8 Hz), 7.51–7.57 (5H, m), 7.70–7.73 (1H, m), 7.87 (1H, dd, J=2.6, 7.2 Hz).

IR (KBr): 1645, 1559, 1539, 1487, 1325, 1252, 829 cm$^{-1}$.

Example 52

[4'-[1-hydroxy-(1H-imidazol-4-yl)ethyl]-N-methyl [1,1'-biphenyl]-3-carboxamide (i) Production of N-methyl-[4'-[(1-trityl-1H-imidazol-4-yl)carbonyl][1,1'-biphenyl]-3-carboxamide To a solution of 3-bromo-N-methylbenzamide (16.0 g) in THF (180 ml) was slowly added dropwise a solution (1.6 M; 103 ml) of n-butyllithium in hexane at −78° C., and the mixture was stirred at −78° C. for 20 min. Trimethoxyborane (50.2 ml) was added dropwise at −78° C. and the mixture was stirred at −78° C. for 30 min and at room temperature for 17 h. 2N Hydrochloric acid (82.0 ml) was added to the reaction mixture, and after stirring for 1 h, the reaction mixture was extracted with ethyl acetate, the organic layer was washed with saturated brine and dried. The solvent was evaporated under reduced pressure to give a crude product (22.5 g) of 3-[(methylamino)carbonyl]phenylboronic acid as a pale-yellow oil. By the reaction in the same manner as in Example 29-(i) using this product (19.2 g), (4-bromophenyl)(1-trityl-1H-imidazol-4-yl)methanone (10.0 g), 2M aqueous sodium carbonate solution (81.2 ml) and tetrakis (triphenylphosphine)palladium(0) (1.17 g), the title compound (6.89 g) was obtained as colorless powder crystals.

$^1$H-NMR (CDCl$_3$) δ: 3.05 (3H, d, J=4.6 Hz), 6.22 (1H, br s) 7.14–7.22 (6H, m), 7.36–7.55 (10H, m), 7.62–7.78 (6H, m), 8.03 (1H, s), 8.37 (2H, d, J=8.8 Hz).

IR (KBr): 1644, 1526, 1186, 1119, 891, 725, 702 cm$^{-1}$.

(ii) Production of [4'-(1-hydroxy-(1-trityl-1H-imidazol-4-yl)ethyl]-N-methyl[1,1'-biphenyl]-3-carboxamide By the reaction in the same manner as in Example 39-(iv) using N-methyl-[4'-[(1-trityl-1H-imidazol-4-yl)carbonyl][1,1'-biphenyl]-3-carboxamide (700 mg) and a solution (1.0 M; 3.83 ml) of methylmagnesium bromide in THF, the title compound (557 mg) was obtained as colorless powder crystals.

$^1$H-NMR (CDCl$_3$) δ: 1.81 (3H, s), 3.04 (3H, d, J=5.2 Hz), 3.36 (1H, s), 6.17 (1H, br s), 6.79 (1H, d, J=1.4 Hz), 7.13–7.18 (6H, m), 7.33–7.51 (15H, m), 7.66–7.71 (2H, m). 7.95 (1H, dd, J=1.8, 1.8 Hz).

IR (KBr): 1644, 1547, 1445, 1159, 910, 735, 702 cm$^{-1}$.

(iii) Production of [4'-[1-hydroxy-(1H-imidazol-4-yl)ethyl]-N-methyl[1,1'-biphenyl]-3-carboxamide By the reaction in the same manner as in Example 41-(ii) using [4'-[1-hydroxy-(1-trityl-1H-imidazol-4-yl)ethyl]-N-methyl[1,1'-biphenyl]-3-carboxamide (527 mg), 10% palladium carbon (527 mg) and 1N hydrochloric acid (0.935 ml), the title compound (144 mg) was obtained as colorless powder crystals.

$^1$H-NMR (CDCl$_3$+CD$_3$OD) δ: 1.93 (3H, s), 3.00 (3H, s), 6.88 (1H, s), 7.44–7.74 (8H, m). 7.99 (1H, s).

IR (KBr): 3279, 1636, 1603, 1582, 1551, 737, 629 cm$^{-1}$.

Example 53

Production of [4'-[1-hydroxy-(1H-imidazol-4-yl)propyl]-N-methyl[1,1'-biphenyl]-3-carboxamide (i) Production of [4'-[1-hydroxy-(1-trityl-1H-imidazol-4-yl)propyl]-N-methyl[1,1'-biphenyl]-3-carboxamide By the reaction in the same manner as in Example 39-(iv) using N-methyl-[4'-[(1-trityl-1H-imidazol-4-yl)carbonyl][1, 1'-biphenyl]-3-carboxamide (1.50 g) and a solution (3.0 M; 2.74 ml) of ethylmagnesium bromide in diethyl ether, the colorless amorphous title compound (1.34 g) was obtained.

$^1$H-NMR (CDCl$_3$) δ: 0.86 (3H, t, J=7.2 Hz), 2.01–2.24 (2H, m), 3.04 (3H, d, J=2.3 Hz), 3.39 (1H, s), 6.24 (1H, br s), 6.78 (1H, d, J=0.7 Hz), 7.13–7.19 (6H, m), 7.31–7.55 (15H, m), 7.67–7.78 (2H, m), 7.94–7.96 (1H, m).

IR (KBr): 1644, 1582, 1541, 1493, 1447, 909, 733,, 700 cm$^{-1}$.

(ii) Production of [4'-[1-hydroxy-(1H-imidazol-4-yl) propyl]-N-methyl[1,1'-biphenyl]-3-carboxamide By the reaction in the same manner as in Example 41-(ii) using [4'-[1-hydroxy-(1-trityl-1H-imidazol-4-yl)propyl]-N-methyl[1,1'-biphenyl]-3-carboxamide (1.29 g), 10% palladium carbon (1.29 g)and 1N hydrochloric acid (2.23 ml), the colorless amorphous title compound (540 mg) was obtained.

$^1$H-NMR (CDCl$_3$+CD$_3$OD) δ: 0.90 (3H, t, J=7.6 Hz), 2.22–2.33 (2H, m), 3.00 (3H, s), 6.93 (1H, s), 7.43–7.71 (8H, m), 8.00 (1H, s).

IR (KBr): 3189, 1634, 1603, 1582, 1557, 835, 812, 627 cm$^{-1}$.

Example 54

Production of [4'-[1-hydroxy-(1H-imidazol-4-yl) butyl]-N-methyl[1,1'-biphenyl]-3-carboxamide (i) Production of [4'-[1-hydroxy-(1-trityl-1H-imidazol-4-yl)-3-butenyl]-N-methyl[1,1'-biphenyl]-3-carboxamide By the reaction in the same manner as in Example 39-(iv) using N-methyl-[4'-[(1-trityl-1H-imidazol-4-yl)carbonyl][1, 1'-biphenyl]-3-carboxamide (800 mg) and a solution (1.0 M; 6.57 ml) of allylmagnesium bromide in THF, the colorless amorphous title compound (770 mg) was obtained.

$^1$H-NMR (CDCl$_3$) δ: 2.80–3.05 (5H, m), 3.36 (1H, s), 5.04–5.12 (2H, m), 5.66–5.82 (1H, m), 6.23 (1H, br s), 6.79 (1H, d, J=1.4 Hz), 7.12–7.19 (6H, m), 7.32–7.54 (15H, m), 7.63–7.78 (2H, m), 7.95–7.96 (1H, m).

IR (KBr): 1644, 1541, 1445, 909, 747, 733, 702 cm$^{-1}$.

(ii) Production of [4'-[1-hydroxy-(1H-imidazol-4-yl) butyl]-N-methyl[1,1'-biphenyl]-3-carboxamide By the reaction in the same manner as in Example 41-(ii) using [4'-[1-hydroxy-(1-trityl-1H-imidazol-4-yl)-3-butenyl]-N-methyl[1,1'-biphenyl]-3-carboxamide (690 mg), 10% palladium carbon (690 mg) and 1N hydrochloric acid (1.17 ml), the colorless amorphous title compound (269 mg) was obtained. The colorless amorphous title compound (420 mg) was obtained.

$^1$H-NMR (CDCl$_3$+CD$_3$OD) δ: 0.91 (3H, t, J=7.2 Hz), 1.21–1.43 (2H, m), 2.09–2.19 (2H, m), 3.00 (3H, s), 6.91 (1H, s), 7.38–7.58 (6H, m), 7.70–7.74 (2H, m), 7.98 (1H, s).

IR (KBr): 3212, 1636, 1582, 1557, 831, 812, 737 cm$^{-1}$.

Example 55

Production of 2-{4'-[1-hydroxy-1-(1H-imidazol-4-yl)-2-methylpropyl][1,1'-biphenyl]-3-yl}-N-methylacetamide (i) Production of 2-(3-bromophenyl)-N-methylacetamide A mixture of 3-bromophenylacetic acid (3.02 g), a solution (2.0 M; 8.5 ml) of methylamine in THF, 1-[3-(dimethylamino)propyl]-3-ethylcarbodiimide hydrochloride (3.20 g), 1-hydroxybenzotriazole (2.60 g) and triethylamine (2.3 ml) was stirred in DMF (30 ml) at room temperature for 24 h. The reaction mixture was diluted with ethyl acetate, washed successively with water, 1N aqueous sodium hydroxide solution, 1N hydrochloric acid, aqueous sodium hydrogen carbonate and brine, dried (magnesium sulfate) and concentrated under reduced pressure. The residue was purified by silica gel chomatography (eluent; ethyl acetate). Recrystallization from hexane-ethyl acetate gave the title compound (1.30 g) as colorless prism crystals.

$^1$H-NMR (CDCl$_3$) δ: 2.70 (3H, d, J=4.8 Hz), 3.45 (2H, s), 5.34 (1H, brs), 7.04–7.20 (2H, m), 7.28–7.39 (2H, m).

IR (KBr): 3285, 1651, 1568 cm$^{-1}$.

(ii) Production of 2-{4'-[1-hydroxy-2-methyl-1-(1-trityl-1H-imidazol-4-yl)propyl][1,1'-biphenyl]-3-yl}-N-methylacetamide By the reaction in the same manner as in Example 33-(ii) using 4-[1-hydroxy-2-methyl-1-(1-trityl-1H-imidazol-4-yl) propyl]phenylboronic acid (3.47 g), 2-(3-bromophenyl)-N-methylacetamide (0.93 g) and tetrakis(triphenylphosphine) palladium(0) (0.21 g), the title compound (580 mg) was obtained as colorless powder crystals.

$^1$H-NMR (CDCl$_3$) δ: 0.76 (3H, d, J=6.6 Hz), 0.93 (3H, d, J=6.6 Hz), 2.36–2.54 (1H, m), 2.76 (3H, d, J=4.6 Hz), 3.55 (1H, s), 3.64 (2H, s), 5.41 (1H, brs), 6.78 (1H, d, J=1.4 Hz), 7.08–7.24 (7H, m), 7.28–7.62 (17H, m).

IR (KBr): 3303, 2969, 1651, 1481, 1445 cm$^{-1}$.

(iii) Production of 2-{4'-[1-hydroxy-1-(1H-imidazol-4-yl)-2-methylpropyl][1,1'-biphenyl]-3-yl}-N-methylacetamide By the reaction in the same manner as in Example 4-(iii) using 2-{4'-[1-hydroxy-2-methyl-1-(1-trityl-1H-imidazol-4-yl)propyl][1,1'-biphenyl]-3-yl}-N-methylacetamide (1.09 g) and pyridine hydrochloride (309 mg), the title compound (260 mg) was obtained as a colorless amorphous powder.

$^1$H-NMR (CDCl$_3$) δ: 0.80 (3H, d, J=6.8 Hz), 0.96 (3H, d, J=6.8 Hz), 2.44–2.66 (1H, m), 2.71 (3H, d, J=4.8 Hz), 3.56 (2H, s), 5.88 (1H, brs), 6.89 (1H, s), 7.16 (1H, d, J=7.8 Hz), 7.27–7.49 (6H, m), 7.53 (2H, d, J=8.4 Hz).

IR (KBr): 3071, 2969, 1651 cm$^{-1}$.

Example 56

Production of N-({4'-[1-hydroxy-1-(1H-imidazol-4-yl)-2-methylpropyl][1,1'-biphenyl]-3-yl}methyl) acetamide (i) Production of N-(3-bromobenzyl)acetamide To a solution of 3-bromobenzylamine hydrochloride (5.20 g) in pyridine (30 ml) was added acetic anhydride (3.2 ml) at 0° C. and the mixture was stirred at room temperature for 24 h. Water and ethyl acetate were added to the reaction mixture for partitioning, and the organic layer was washed with 1N hydrochloric acid, aqueous sodium hydrogen carbonate and brine, dried (magnesium sulfate) and concentrated under reduced pressure. The residue was recrystallized from hexane-ethyl acetate to give the title compound (4.00 g) as colorless needle crystals.

$^1$H-NMR (CDCl$_3$) δ: 2.02 (3H, d, J=1.4 Hz), 4.38 (2H, d, J=6.0 Hz), 6.04 (1H, brs), 7.10–7.26 (2H, m), 7.30–7.48 (2H, m).

IR (KBr): 3283, 1636, 1549 cm$^{-1}$.

(ii) Production of N-({4'-[1-hydroxy-2-methyl-1-(1-trityl-1H-imidazol-4-yl)propyl][1,1'-biphenyl]-3-yl}methyl)acetamide By the reaction in the same manner as in Example 33-(ii) using 4-[1-hydroxy-2-methyl-1-(1-trityl-1H-imidazol-4-yl)propyl]phenylboronic acid (3.30 g), N-(3-bromobenzyl)acetamide (1.05 g) and tetrakis(triphenylphosphine)palladium(0) (0.18 g), the title compound (1.24 g) was obtained as a pale-yellow amorphous powder.

$^1$H-NMR (CDCl$_3$) δ: 0.76 (3H, d, J=6.7 Hz), 0.92 (3H, d, J=6.7 Hz), 2.04 (3H, s), 2.36–2.54 (1H, m), 3.55 (1H, s), 4.49 (2H, d, J=5.8 Hz), 5.80 (1H, brs), 6.78 (1H, d, J=1.4 Hz), 7.06–7.24 (7H, m), 7.26–7.60 (17H, m).

IR (KBr): 3293, 2967, 1659, 1445 cm$^{-1}$.

(iii) Production of N-({4'-[1-hydroxy-1-(1H-imidazol-4-yl)-2-methylpropyl][1,1'-biphenyl]-3-yl}methyl)acetamide By the reaction in the same manner as in Example 4-(iii) using N-({4'-[1-hydroxy-2-methyl-1-(1-trityl-1H-imidazol-4-yl)propyl][1,1'-biphenyl]-3-yl}methyl)acetamide (1.05 g) and pyridine hydrochloride (278 mg), the title compound (490 mg) was obtained as a colorless amorphous powder.

$^1$H-NMR (CDCl$_3$) δ: 0.82 (3H, d, J=6.8 Hz), 0.98 (3H, d, J=6.8 Hz), 2.02 (3H, s), 2.53–2.70 (1H, m), 4.46 (2H, d, J=5.6 Hz), 5.94 (1H, brs), 6.96 (1H, d, J=1.0 Hz), 7.19–7.26 (1H, m), 7.37 (1H, t, J=7.7 Hz), 7.42–7.53 (5H, m), 7.58 (2H, d, J=8.4 Hz).

IR (KBr): 3264, 1651, 1559 cm$^{-1}$.

Example 57

Production of 1-{4'-[1-hydroxy-1-(1H-imidazol-4-yl)-2-methylpropyl][1,1'-biphenyl]-3-yl}ethanone

(i) Production of 1-{4'-[1-hydroxy-2-methyl-1-(1-trityl-1H-imidazol-4-yl)propyl][1,1'-biphenyl]-3-yl}ethanone By the reaction in the same manner as in Example 33-(ii) using 4-[1-hydroxy-2-methyl-1-(1-trityl-1H-imidazol-4-yl)propyl]phenylboronic acid (6.22 g), 3'-bromoacetophenone (2.30 g) and tetrakis(triphenylphosphine)palladium(0) (0.210 g), the title compound (1.50 g) was obtained as colorless powder crystals.

$^1$H-NMR (CDCl$_3$) δ: 0.77 (3H, d, J=7.0 Hz), 0.93 (3H, d, J=7.0 Hz), 2.38–2.58 (1H, m), 2.66 (3H, s), 3.55 (1H, s), 6.78 (1H, d, J=1.4 Hz), 7.07–7.20 (6H, m), 7.28–7.40 (9H, m), 7.46–7.71 (6H, m), 7.74–7.84 (1H, m), 7.87–7.95 (1H, m), 8.17 (1H, t, J=1.7 Hz).

IR (KBr): 2967, 1688, 1236 cm$^{-1}$.

(ii) Production of 1-{4'-[1-hydroxy-1-(1H-imidazol-4-yl)-2-methylpropyl][1,1'-biphenyl]-3-yl}ethanone By the reaction in the same manner as in Example 4-(iii) using 1-{4'-[1-hydroxy-2-methyl-1-(1-trityl-1H-imidazol-4-yl)propyl][1,1'-biphenyl]-3-yl}ethanone (3.30 g) and pyridine hydrochloride (870 mg), the title compound (910 mg) was obtained as a colorless amorphous powder.

$^1$H-NMR (CDCl$_3$) δ: 0.83 (3H, d, J=6.6 Hz), 0.99 (3H, d, J=6.6 Hz), 2.50–2.80 (4H, m), 6.99 (1H, s), 7.44–7.69 (6H, m), 7.76 (1H, d, J=8.0 Hz), 7.90 (1H, d, J=8.0 Hz), 8.15 (1H, s).

IR (KBr): 2971, 1682, 1238 cm$^{-1}$.

Example 58

Production of (−)-1-(4'-fluoro[1,1'-biphenyl]-3-yl)-1-(1H-imidazol-4-yl)-2-methyl-1-propanol 1-(4'-Fluoro[1,1'-biphenyl]-3-yl)-1-(1H-imidazol-4-yl)-2-methyl-1-propanol obtained in Example 13 was subjected to liquid chromatography (eluent; hexane:ethanol=9:1) using an optically active column (Chiralpak AD) to give (−)-1-(4'-fluoro[1,1'-biphenyl]-3-yl)-1-(1H-imidazol-4-yl)-2-methyl-1-propanol as an enantiomer of the first eluate.

Optical purity; 99% ee (Chiralpak AD)

[a]$_D^{20}$ −47.1° (C=0.31, methanol)

Example 59

Production of 4-fluoro-4'-[1-hydroxy-1-(-1H-imidazol-4-yl)-2-methylpropyl][1,1'-biphenyl]-3-carboxamide

(i) Production of 4-fluoro-4'-[1-hydroxy-2-methyl-1-(1-trityl-1H-imidazol-4-yl)propyl][1,1'-biphenyl]-3-carboxamide By the reaction in the same manner as in Example 33-(ii) using 5-bromo-2-fluorobenzonitrile (1.04 g), a crude product (3.40 g) of 4-[1-hydroxy-2-methyl-1-(1-trityl-1H-imidazol-4-yl)propyl]phenylboronic acid, 2M aqueous sodium carbonate solution (5.20 ml) and tetrakis(triphenylphosphine)palladium(0) (211 mg), the title compound (1.25 g) was obtained as colorless needle crystals.

$^1$H-NMR (CDCl$_3$) δ: 0.75 (3H, d, J=7.0 Hz), 0.93 (3H, d, J=6.6 Hz), 2.41–2.48 (1H, m), 3.54 (1H, s), 6.78 (1H, d, J=1.0 Hz), 7.12–7.15 (4H, m), 7.22–7.35 (13H, m), 7.42 (2H, d, J=8.4 Hz), 7.72 (2H, d, J=8.4 Hz), 7.74–7.81 (2H, m).

IR (KBr): 2236, 1493, 1447, 910, 818, 747, 735, 702 cm$^{-1}$.

(ii) 4-fluoro-4'-[1-hydroxy-1-(-1H-imidazol-4-yl)-2-methylpropyl][1,1'-biphenyl]-3-carboxamide By the reaction in the same manner as in Example 4-(iii) using 4-fluoro-4-[1-hydroxy-2-methyl-1-(1-trityl-1H-imidazol-4-yl)propyl][1,1'-biphenyl]-3-carboxamide (1.20 g) and pyridine hydrochloride (432 mg), the colorless amorphous title compound (577 mg) was obtained.

$^1$H-NMR (CDCl$_3$+CD$_3$OD) δ: 0.82 (3H, d, J=6.6 Hz), 0.97 (3H, d, J=6.6 Hz), 2.57–2.67 (1H, m), 6.98 (1H, s), 7.29 (1H, d, J=6.6 Hz), 7.44 (2H, d, J=8.2 Hz), 7.56–7.63 (3H, m), 7.76–7.79 (2H, m).

IR (KBr): 3133, 2973, 2236, 1493, 1273, 1244, 1119, 1015, 818 cm$^{-1}$.

Example 60

Production of (−)-N-{4'-[1-hydroxy-1-(1H-imidazol-4-yl)-2-methylpropyl][1,1'-biphenyl]-3-yl}acetamide N-{4'-[1-Hydroxy-1-(1H-imidazol-4-yl)-2-methylpropyl]-[1,1'-biphenyl]-3-ylacetamide obtained in Example 31 was subjected to liquid chromatography (eluent; hexane:ethanol=9:1) using an optically active column (Chiralpak AD) to give (−)-N-{4'-[1-hydroxy-1-(1H-imidazol-4-yl)-2-methylpropyl][1,1'-biphenyl]-3-yl}acetamide as an enantiomer off the first eluate.

Optical purity; 99.9% ee (Chiralpak AD)

[a]$_D^{20}$ −17.3° (C=1.0 methanol)

Example 61

Production of 1-(3',4'-dimethoxy[1,1'-biphenyl]-4-yl)-1-(1H-imidazol-4-yl)-2-methyl-1-propanol

(i) Production of 1-(3',4'-dimethoxy[1,1'-biphenyl]-4-yl)-2-methyl-1-(1-trityl-1H-imidazol-4-yl)-1-propanol By the reaction in the same manner as in Example 29-(i) using 1-(4-bromophenyl)-(1-trityl-1H-imidazol-4-yl)-2- methyl-1-propanol (1.50 g), 3,4-dimethoxyphenylboronic acid (762 mg), 2M aqueous sodium carbonate solution (2.79 ml) and tetrakis(triphenylphosphine)palladium(0) (96.7 mg), the colorless amorphous title compound (1.42 g) was obtained.

$^1$H-NMR (CDCl$_3$) δ: 0.77 (3H, d, J=6.6 Hz), 0.93 (3H, d, J=6.6 Hz), 2.40–2.53 (1H, m), 3.51 (1H, s), 3.92 (3H, s), 3.95 (3H, s), 6.78 (1H, d, J=1.0 Hz), 6.93 (1H, d, J=8.2 Hz), 7.11–7.16 (8H, m), 7.31–7.35 (10H, m), 7.46 (2H, d, J=8.4 Hz), 7.55 (2H, d, J=8.4 Hz).

IR (KBr): 1470, 1445, 1250, 1217, 1173, 747, 731, 702 cm$^{-1}$.

(ii) Production of 1-(3',4'-dimethoxy[1,1'-biphenyl]-4-yl)-1-(1H-imidazol-4-yl)-2-methyl-1-propanol By the reaction in the same manner as in Example 4-(iii) using 1-(3',4'-dimethoxy[1,1'-biphenyl]-4-yl)-2-methyl-1-(1-trityl-1H-imidazol-4-yl)-1-propanol (1.37 g) and pyridine hydrochloride (479 mg), the colorless amorphous title compound (660 mg) was obtained.

$^1$H-NMR (CDCl$_3$+CD$_3$OD) δ: 0.83 (3H, d, J=7.0 Hz), 0.99 (3H, d, J=6.6 Hz), 2.57–2.67 (1H, m), 3.91 (3H, s), 3.93 (3H, s), 6.90–6.98 (2H, m), 7.10–7.15 (2H, m), 7.47–7.63 (5H, m).

IR (KBr): 1526, 1505, 1464, 1219, 1171, 1142, 1026, 829, 806 cm$^{-1}$.

Example 62

Production of 1-(3'-methoxy[1,1'-biphenyl]-4-yl)-1-(1H-imidazol-4-yl)-2-methyl-1-propanol (i) Production of 1-(3'-methoxy[1,1'-biphenyl]-4-yl)-2-methyl-1-(1-trityl-1H-imidazol-4-yl)-1-propanol By the reaction in the same manner as in Example 29-(i) using 1-(4-bromophenyl)-(1-trityl-1H-imidazol-4-yl)-2-methyl-1-propanol (1.50 g), 3-methoxyphenylboronic acid (635 mg), 2M aqueous sodium carbonate solution (2.79 ml) and tetrakis(triphenylphosphine)palladium(0) (96.7 mg), the title compound (1.01 g) was obtained as colorless powder crystals.

$^1$H-NMR (CDCl$_3$) δ: 0.77 (3H, d, J=7.0 Hz), 0.93 (3H, d, J=7.0 Hz), 2.39–2.49 (1H, m), 3.54 (1H, s), 3.86 (3H, s), 6.77 (1H, d, J=1.4 Hz), 6.87 (1H, dd, J=02.4, 7.2 Hz), 7.11–7.19 (8H, m), 7.30–7.38 (10H, m), 7.47–7.66 (5H, m).

IR (KBr): 1599, 1480, 1447, 1213, 1167, 909, 822, 747, 733, 702 cm$^{-1}$.

(ii) Production of 1-(3'-methoxy[1,1'-biphenyl]-4-yl)-1-(1H-imidazol-4-yl)-2-methyl-1-propanol By the reaction in the same manner as in Example 4-(iii) using 1-(3'-methoxy[1,1'-biphenyl]-4-yl)-2-methyl-1-(1-trityl-1H-imidazol-4-yl)-1-propanol (960 mg) and pyridine hydrochloride (354 mg), the colorless amorphous title compound (483 mg) was obtained.

$^1$H-NMR (CDCl$_3$+CD$_3$OD) δ: 0.82 (3H, d, J=6.6 Hz), 0.98 (3H, d, J=6.6 Hz), 2.59–2.69 (1H, m), 3.85 (3H, s), 6.86–6.96 (2H, m), 7.11–7.18 (2H, m), 7.29–7.65 (6H, m).

IR (KBr): 1481, 1296, 1219, 1171, 1032, 1015, 826, 775, 696 cm$^{-1}$.

Example 63

Production of 1-(1H-imidazol-4-yl)-2-methyl-1-[3-(4-pyridyl)phenyl]-1-propanol (i) Production of 2-methyl-1-[3-(4-pyridyl)phenyl]-1-(1-trityl-1H-imidazol-4-yl)-1-propanol By the reaction in the same manner as in Example 29-(i) using 1-(3-bromophenyl)-(1-trityl-1H-imidazol-4-yl)-2-methyl-1-propanol (1.20 g), 4-pyridylboronic acid (754 mg), 2M aqueous sodium carbonate solution (2.23 ml) and tetrakis(triphenylphosphine)palladium(0) (155 mg), the pale-yellow amorphous title compound (1.13 g) was obtained.

$^1$H-NMR (CDCl$_3$) δ: 0.75 (3H, d, J=6.6 Hz), 0.95 (3H, d, J=6.6 Hz), 2.05–2.50 (1H, m), 3.72 (1H, s), 7.86 (1H, d, J=0.6 Hz), 7.10–7.15 (7H, m), 7.27–7.47 (12H, m), 7.51–7.75 (3H, m), 8.62–8.65 (2H, m).

IR (KBr): 1597, 1445, 909, 791, 747, 735, 702, 660 cm$^{-1}$.

(ii) Production of 1-(1H-imidazol-4-yl)-2-methyl-1-[3-(4-pyridyl)phenyl]-1-propanol By the reaction in the same manner as in Example 4-(iii) using 2-methyl-1-[3-(4-pyridyl)phenyl]-1-(1-trityl-1H-imidazol-4-yl)-1-propanol (1.08 g) and pyridine hydrochloride (419 mg), the colorless amorphous title compound (477 mg) was obtained.

$^1$H-NMR (CDCl$_3$) δ: 0.82 (3H, d, J=7.0 Hz), 1.00 (3H, d, J=7.0 Hz), 2.59–2.72 (1H, m), 7.00 (1H, s), 7.36–7.62 (6H, m), 7.89 (1H, s), 8.57–8.60 (2H, m).

IR (KBr): 3073, 2969, 1599, 1476, 1005, 909, 831, 789, 733, 619 cm$^{-1}$.

Example 64

Production of 1-(1H-imidazol-4-yl)-2-methyl-1-[3-(3-pyridyl)phenyl]-1-propanol (i) Production of 2-methyl-1-[3-(3-pyridyl)phenyl]-1-(1-trityl-1H-imidazol-4-yl)-1-propanol By the reaction in the same manner as in Example 4-(ii) using 1-(3-bromophenyl)-2-methyl-1-(1-trityl-1H-imidazol-4-yl)-1-propanol (1.01 g), diethyl(3-pyridyl)borane (0.497 g) and tetrakis(triphenylphosphine)palladium(0) (0.170 g), the title compound (0.657 g) was obtained as a pale-yellow amorphous powder.

$^1$H-NMR (CDCl$_3$) δ: 0.76 (3H, d, J=6.7 Hz), 0.94 (3H, d, J=6.7 Hz), 2.30–2.55 (1H, m), 3.70 (1H, s), 6.78 (1H, d, J=1.4 Hz), 7.05–7.46 (19H, m), 7.50–7.62 (1H, m), 7.69 (1H, s), 7.82 (1H, dt, J=8.0, 2.0 Hz), 8.59 (1H, dd, J=2.0, 4.8 Hz), 8.80 (1H, d, J=2.2 Hz).

IR (KBr): 1491, 1470, 1445, 912 cm$^{-1}$.

(ii) Production of 1-(1H-imidazol-4-yl)-2-methyl-1-[3-(3-pyridyl)phenyl]-1-propanol By the reaction in the same manner as in Example 4-(iii) using 2-methyl-1-[3-(3-pyridyl)phenyl]-1-(1-trityl-1H-imidazol-4-yl)-1-propanol (0.57 g) and pyridine hydrochloride (208 mg), the title compound (288 mg) was obtained as colorless powder crystals.

$^1$H-NMR (CDCl$_3$+CD$_3$OD) δ: 0.82 (3H, d, J=6.6 Hz), 0.99 (3H, d, J=6.6 Hz), 2.55–2.76 (1H, m), 6.99 (1H, d, J=1.3 Hz), 7.34–7.47 (3H, m), 7.52 (1H, d, J=1.3 Hz), 7.50–7.59 (1H, m), 7.77 (1H, s), 7.88–7.98 (1H, m), 8.50 (1H, dd, J=2.2, 5.0 Hz), 8.75 (1H, dd, J=0.8, 2.2 Hz).

IR (KBr): 2971, 1470, 1022, 970 cm$^{-1}$.

Example 65

Production of 1-(1H-imidazol-4-yl)-2-methyl-1-[3-(2-pyridyl)phenyl]-1-propanol (i) Production of 2-methyl-1-[3-(2-pyridyl)phenyl]-1-(1-trityl-1H-imidazol-4-yl)-1-propanol 1-(3-Bromophenyl)-(1-trityl-1H-imidazol-4-yl)-2-methyl-1-propanol (1.15 g) and a solution of tri-n-butyl(2- pyridyl)tin (1.01 g) in DMF (10 ml) was deaerated and tetrakis(triphenylphosphine)palladium(0) (73.1 mg) was added. The mixture was stirred under an argon atmosphere at 80° C. for 5 h and copper(I) iodide (20.1 mg) and tetrakis(triphenylphosphine)palladium(0) (48.7 mg) were added. The mixture was stirred at 100° C. for 18 h. Water was added to the reaction mixture and the mixture was extracted with ethyl acetate, washed with 5% aqueous ethylenediamine solution, water (twice) and saturated brine and dried over anhydrous magnesium sulfate. The solvent was evaporated under reduced pressure and the residue was purified by silica gel chomatography (eluent; hexane:ethyl acetate=3:1→2:1). Recrystallization from ethyl acetate-hexane gave the title compound (577 mg, 51%) as colorless powder crystals.

$^1$H-NMR (CDCl$_3$) δ: 0.76 (3H, d, J=6.6 Hz), 0.93 (3H, d, J=6.6 Hz), 2.45–2.52 (1H, m), 3.68 (1H, s), 6.86 (1H, d, J=1.6 Hz), 7.10–7.43 (18H, m), 7.58–7.86 (4H, m), 8.09–8.10 (1H, m), 8.66–8.69 (1H, m).

IR (KBr): 1586, 1493, 1472, 1445, 909, 774, 747, 733, 702 cm$^{-1}$.

(ii) Production of 1-(1H-imidazol-4-yl)-2-methyl-1-[3-(2-pyridyl)phenyl]-1-propanol By the reaction in the same manner as in Example 4-(iii) using 2-methyl-1-[3-(2-pyridyl)phenyl]-1-(1-trityl-1H-imidazol-4-yl)-1-propanol (527 mg), pyridine hydrochloride (205 mg), the title compound (197 mg) was obtained as colorless plate crystals.

$^1$H-NMR (CDCl$_3$) δ: 0.80 (3H, d, J=7.0 Hz), 0.96 (3H, d, J=6.6 Hz), 2.58–2.71 (1H, m), 6.89 (1H, s), 7.17–7.24 (1H, m), 7.35–7.43 (2H, m), 7.59 (1H, d, J=7.8 Hz), 7.67–7.79 (3H, m), 8.16 (1H, s), 8.62 (1H, d, J=4.8 Hz).

IR (KBr): 3187, 1584, 1460, 1362, 1304, 1007, 799, 768 cm$^{-1}$.

Example 66

Production of N-{3'-[1-hydroxy-1-(1H-imidazol-4-yl)-2-methylpropyl][1,1'-biphenyl]-3-yl}acetamide (i) Production of N-{3'-[1-hydroxy-2-methyl-1-(1-trityl-1H-imidazol-4-yl)propyl][1,1'-biphenyl]-3-yl}acetamide By the reaction in the same manner as in Example 4-(ii) using 1-(3-bromophenyl)-2-methyl-1-(1-trityl-1H-imidazol-4-yl)-1-propanol (1.02 g), 3-acetamidebenzeneboronic acid (0.531 g) and tetrakis(triphenylphosphine)palladium(0) (0.170 g), the title compound (0.980 g) was obtained as a pale-yellow amorphous powder.

1H-NMR (CDCl$_3$) δ: 0.75 (3H, d, J=6.8 Hz), 0.93 (3H, d, J=6.8 Hz), 2.16 (3H, s), 2.35–2.58 (1H, m), 3.68 (1H, brs), 6.80 (1H, d, J=1.4 Hz), 7.04–7.18 (6H, m), 7.20–7.42 (13H, m), 7.44–7.56 (3H, m), 7.62–7.74 (2H, m).

IR (KBr): 3289, 1669, 1557, 1493 cm$^{-1}$.

(ii) Production of N-{3'-[1-hydroxy-1-(1H-imidazol-4-yl)-2-methylpropyl][1,1'-biphenyl]-3-yl}acetamide By the reaction in the same manner as in Example 4-(iii) using N-{3'-[1-hydroxy-2-methyl-1-(1-trityl-1H-imidazol-4-yl)propyl][1,1'-biphenyl]-3-yl}acetamide (0.781 g) and pyridine hydrochloride (290 mg), the title compound (315 mg) was obtained as colorless powder crystals.

$^1$H-NMR (DMSO-d$_6$) δ: 0.69 (3H, d, J=6.6 Hz), 0.82 (3H, d, J=6.6 Hz), 2.07 (3H, s), 2.57–2.78 (1H, m), 5.12 (1H, brs), 6.96 (1H, s), 7.21–7.43 (4H, m), 7.50–7.66 (3H, m), 7.80 (1H, s), 7.88 (1H, s).

IR (KBr): 3295, 1667, 1557, 789 cm$^{-1}$.

Example 67

Production of 5-{4-[1-hydroxy-1-(1H-imidazol-4-yl)-2-methylpropyl]phenyl}-N-methylnicotinamide (i) Production of 5-bromo-N-methylnicotinamide By the reaction in the same manner as in Example 55-(i) using 5-bromonicotinic acid (5.01 g), a solution (2.0 M ; 30 ml) of methylamine in THF, 1-[3-(dimethylamino)propyl]-3-ethylcarbodiimide hydrochloride (5.79 g) and 1-hydroxybenzotriazole (4.72 g), the title compound (2.30 g) was obtained as colorless prism crystals.

$^1$H-NMR (CDCl$_3$) δ: 3.04 (3H, d, J=4.8 Hz), 6.45 (1H, brs), 8.27 (1H, t, J=2.1 Hz), 8.78 (1H, d, J=2.1 Hz), 8.86 (1H, d, J=2.1 Hz).

IR (KBr): 3297, 3025, 1645, 1416 cm$^{-1}$.

(ii) Production of 5-{4-[1-hydroxy-2-methyl-1-(1-trityl-1H-imidazol-4-yl)propyl]phenyl}-N-methylnicotinamide By the reaction in the same manner as in Example 33-(ii) using 4-[1-hydroxy-2-methyl-1-(1-trityl-1H-imidazol-4-yl)propyl]phenylboronic acid (3.0 g), 5-bromo-N-methylnicotinamide (1.01 g) and tetrakis(triphenylphosphine)palladium(0) (0.177 g), the title compound (1.26 g) was obtained as colorless powder crystals.

$^1$H-NMR (CDCl$_3$) δ: 0.76 (3H, d, J=6.6 Hz), 0.93 (3H, d, J=6.6 Hz), 2.36–2.60 (1H, m), 3.07 (3H, d, J=5.2 Hz), 3.59 (1H, s), 6.30 (1H, brs), 6.78 (1H, d, J=1.4 Hz), 7.06–7.20 (6H, m), 7.26–7.38 (10H, m), 7.52 (2H, d, J=8.4 Hz), 7.63 (2H, d, J=8.4 Hz), 8.29 (1H, t, J=2.2 Hz), 8.88 (1H, d, J=2.2 Hz), 8.94 (1H, d, J=2.2 Hz).

IR (KBr): 3227, 2969, 1651 cm$^{-1}$.

(iii) Production of 5-{4-[1-hydroxy-1-(1H-imidazol-4-yl)-2-methylpropyl]phenyl}-N-methylnicotinamide By the reaction in the same manner as in Example 4-(iii) using 5-{4-[1-hydroxy-2-methyl-1-(1-trityl-1H-imidazol-4-yl)propyl]phenyl}-N-methylnicotinamide (1.44 g) and pyridine hydrochloride (466 mg), the title compound (360 mg) was obtained as a colorless amorphous powder.

$^1$H-NMR (CDCl$_3$+CD$_3$OD) δ: 0.80 (3H, d, J=6.8 Hz), 0.98 (3H, d, J=6.8 Hz), 2.40–2.80 (1H, m), 3.02 (3H, s), 6.98 (1H, d, J=1.0 Hz), 7.45 (2H, d, J=8.4 Hz), 7.48 (1H, d, J=1.0 Hz), 7.59 (2H, d, J=8.4 Hz), 8.28 (1H, t, J=2.1 Hz), 8.78 (1H, d, J=2.1 Hz), 8.84 (1H, d, J=2.1 Hz).

IR (KBr): 3200, 2971, 1651, 1557 cm$^{-1}$.

Example 68

Production of N-(6-{4-[1-hydroxy-1-(1H-imidazol-4-yl)-2-methylpropyl]phenyl}-2-pyridyl)acetamide (i) Production of N-(6-bromo-2-pyridyl)acetamide By the reaction in the same manner as in Example 56-(i) using 2-amino-6-bromopyridine (2.97 g) and acetic anhydride (2.9 ml), the title compound (2.30 g) was obtained as colorless scaly crystals.

$^1$H-NMR (CDCl$_3$) δ: 2.20 (3H, s), 7.21 (1H, d, J=8.0 Hz), 7.56 (1H, t, J=8.0 Hz), 8.05 (1H, brs), 8.15 (1H, d, J=8.0 Hz).

IR (KBr): 3231, 1661, 1574, 1439, 1391 cm$^{-1}$.

(ii) Production of N-(6-{4-[1-hydroxy-2-methyl-1-(1-trityl-1H-imidazol-4-yl)propyl]phenyl}-2-pyridyl)acetamide By the reaction in the same manner as in Example 33-(ii) using 4-[1-hydroxy-2-methyl-1-(1-trityl-1H-imidazol-4-yl)propyl]phenylboronic acid (3.01 g), N-(6-bromo-2-pyridyl)acetamide (1.05 g) and tetrakis(triphenylphosphine)palladium(0) (0.138 g), the title compound (0.720 g) was obtained as colorless powder crystals.

$^1$H-NMR (CDCl$_3$) δ: 0.74 (3H, d, J=6.8 Hz), 0.92 (3H, d, J=6.8 Hz) 2.20 (3H, s), 2.34–2.58 (1H, m), 3.60 (1H, s), 6.77 (1H, d, J=1.4 Hz), 7.06–7.20 (6H, m), 7.28–7.42 (10H, m), 7.44 (1H, dd, J=0.8, 7.9 Hz), 7.59 (2H, d, J=8.4 Hz), 7.75 (1H, t, J=7.9 Hz), 7.83 (2H, d, J=8.4 Hz), 8.05–8.16 (2H, m).

IR (KBr): 2969, 1732, 1690, 1447 cm$^{-1}$.

(iii) Production of N-(6-{4-[1-hydroxy-1-(1H-imidazol-4-yl)-2-methylpropyl]phenyl}-2-pyridyl)acetamide By the reaction in the same manner as in Example 4-(iii) using N-(6-(4-[1-hydroxy-2-methyl-1-(1-trityl-1H-imidazol-4-yl)propyl]phenyl}-2-pyridyl)acetamide (1.48 g) and pyridine hydrochloride (520 mg), the title compound (520 mg) was obtained as colorless powder crystals.

$^1$H-NMR (CDCl$_3$+CD$_3$OD) δ: 0.81 (3H, d, J=6.7 Hz), 0.98 (3H, d, J=6.7 Hz), 2.22 (3H, s), 2.52–2.74 (1H, m), 6.97 (1H, d, J=1.0 Hz), 7.44 (1H, d, J=7.8 Hz), 7.52 (1H, d, J=1.0 Hz), 7.59 (2H, d, J=8.4 Hz), 7.76 (1H, t, J=7.8 Hz), 7.83 (2H, d, J=8.4 Hz), 8.09 (1H, d, J=7.8 Hz).

IR (KBr): 3177, 2967, 1651, 1559, 1451 cm$^{-1}$.

Example 69

Production of 6-{4-[1-hydroxy-1-(1H-imidazol-4-yl)-2-methylpropyl]phenyl}-N-methyl-2-pyridinecarboxamide (i) Production of 6-bromo-N-methyl-2-pyridinecarboxamide By the reaction in the same manner as in Example 55-(i) using 6-bromopicolinic acid (3.00 g), a solution (2.0 M; 18 ml) of methylamine in THF, 1-[3-(dimethylamino)propyl]-3-ethylcarbodiimide hydrochloride (3.41 g) and 1-hydroxybenzotriazole (2.99 g), the title compound (2.60 g) was obtained as pale-brown oil.

$^1$H-NMR (CDCl$_3$) δ: 3.04 (3H, d, J=5.2 Hz), 7.60 (1H, dd, J=1.0, 7.6 Hz), 7.72 (1H, t, J=7.6 Hz), 8.16 (1H, dd, J=1.0, 7.6 Hz).

IR (neat): 3391, 1682, 1669, 1557, 1539 cm$^{-1}$.

(ii) Production of 6-{4-[1-hydroxy-2-methyl-1-(1-trityl-1H-imidazol-4-yl)propyl]phenyl}-N-methyl-2-pyridinecarboxamide By the reaction in the same manner as in Example 33-(ii) using 4-[1-hydroxy-2-methyl-1-(1-trityl-1H-imidazol-4-yl)propyl]phenylboronic acid (2.97 g), 6-bromo-N-methyl-2-pyridinecarboxamide (1.30 g) and tetrakis(triphenylphosphine)palladium(0) (0.110 g), the title compound (1.11 g) was obtained as colorless powder crystals.

$^1$H-NMR (CDCl$_3$+CD$_3$OD) δ: 0.76 (3H, d, J=6.6 Hz), 0.94 (3H, d, J=6.6 Hz), 2.44–2.64 (1H, m), 3.04–3.10 (3H, m), 6.83 (1H, d, J=1.2 Hz), 7.08–7.20 (6H, m), 7.30–7.40 (10H, m), 7.63 (2H, d, J=8.4 Hz), 7.82–7.98 (4H, m), 8.06–8.14 (1H, m), 8.33 (1H, brs).

IR (KBr): 3387, 2967, 1672, 1449 cm$^{-1}$.

(iii) Production of 6-{4-[1-hydroxy-1-(1H-imidazol-4-yl)-2-methylpropyl]phenyl}-N-methyl-2-pyridinecarboxamide By the reaction in the same manner as in Example 4-(iii) using 6-{4-[1-hydroxy-2-methyl-1-(1-trityl-1H-imidazol-4-yl)propyl]phenyl}-N-methyl-2-pyridinecarboxamide (1.44 g) and pyridine hydrochloride (550 mg), the title compound (255 mg) was obtained as a colorless amorphous powder.

$^1$H-NMR (CDCl$_3$) δ: 0.81 (3H, d, J=6.6 Hz), 0.99 (3H, d, J=6.6 Hz), 2.48–2.70 (1H, m), 3.02 (3H, d, J=5.2 Hz), 6.98 (1H, s), 7.48 (1H, s), 7.64 (2H, d, J=8.4 Hz), 7.70–7.83 (2H, m), 7.88 (2H, d, J=8.4 Hz), 8.04 (1H, d, J=7.0 Hz), 8.16–8.30 (1H, m).

IR (KBr): 2969, 1667, 1537, 1449 cm$^{-1}$.

Example 70

Production of N-(2-{4-[1-hydroxy-1-(1H-imidazol-4-yl)-2-methylpropyl]phenyl}-4-pyridyl)acetamide (i) Production of 1-[4-(4-amino-2-pyridyl)phenyl]-2-methyl-1-(1-trityl-1H-imidazol-4-yl)-1-propanol By the reaction in the same manner as in Example 33-(ii) using 4-[1-hydroxy-2-methyl-1-(1-trityl-1H-imidazol-4-yl)propyl]phenylboronic acid (5.78 g), 4-amino-2-chloropyridine (1.00 g), sodium bromide (810 mg) and tetrakis(triphenylphosphine)palladium(0) (0.190 g), the title compound (2.30 g) was obtained as a yellow amorphous powder.

$^1$H-NMR (CDCl$_3$) δ: 0.74 (3H, d, J=6.5 Hz), 0.91 (3H, d, J=6.5 Hz), 2.36–2.56 (1H, m), 3.61 (1H, s), 4.17 (2H, s), 6.46 (1H, dd, J=2.2, 5.6 Hz), 6.77 (1H, s), 6.93 (1H, d, J=2.2 Hz), 7.06–7.19 (6H, m), 7.27–7.39 (10H, m), 7.56 (2H, d, J=8.2 Hz), 7.82 (2H, d, J=8.2 Hz), 8.29 (1H, d, J=5.6 Hz).

IR (KBr): 3335, 3210, 1599, 1445 cm$^{-1}$.

(ii) Production of N-(2-{4-[1-hydroxy-2-methyl-1-(1-trityl-1H-imidazol-4-yl)propyl]phenyl}-4-pyridyl)acetamide A mixture of 1-[4-(4-amino-2-pyridyl)phenyl]-2-methyl-1-(1-trityl-1H-imidazol-4-yl)-1-propanol (1.40 g), acetic anhydride (0.46 ml), triethylamine (0.71 ml) and p-dimethylaminopyridine (20 mg) was stirred in THF (20 ml) at 60° C. for 16 h. The solvent was evaporated and ethyl acetate and water were added to the residue for partitioning. The organic layer was washed with aqueous sodium hydrogen carbonate and brine, dried (magnesium sulfate) and concentrated under reduced pressure. The residue was dissolved in a mixture of acetonitrile (10 ml)—water (10 ml) and tetrabutylammonium bromide (13 mg) was added. The mixture was stirred at room temperature for 10 h. The organic layer was separated and the aqueous layer was extracted with ethyl acetate. The organic layer was combined, and the mixture was dried (magnesium sulfate) and concentrated under reduced pressure. The residue was purified by silica gel chomatography (eluent; hexane:ethyl acetate=2:1). Recrystallization from ethyl acetate gave the title compound (630 mg) as colorless powder crystals.

¹H-NMR (CDCl₃+CD₃OD) δ: 0.74 (3H, d, J=6.8 Hz), 0.92 (3H, d, J=6.8 Hz), 2.19 (3H, s), 2.42–2.62 (1H, m), 6.82 (1H, d, J=1.0 Hz), 7.06–7.20 (6H, m), 7.26–7.42 (10H, m), 7.50–7.62 (3H, m), 7.77–7.88 (3H, m), 8.46 (1H, d, J=5.6 Hz).

IR (KBr): 3264, 2973, 1707, 1588 cm⁻¹.

(iii) Production of N-(2-{4-[1-hydroxy-1-(1H-imidazol-4-yl)-2-methylpropyl]phenyl}-4-pyridyl)acetamide By the reaction in the same manner as in Example 4-(iii) using N-(2-{4-[1-hydroxy-2-methyl-1-(1-trityl-1H-imidazol-4-yl)propyl]phenyl}-4-pyridyl)acetamide (0.590 g) and pyridine hydrochloride (190 mg), the title compound (150 mg) was obtained as colorless powder crystals.

¹H-NMR (CDCl₃+CD₃OD) δ: 0.81 (3H, d, J=6.6 Hz), 0.99 (3H, d, J=6.6 Hz), 2.19 (3H, s), 2.50–2.78 (1H, m), 6.98 (1H, m), 7.50–7.66 (4H, m), 7.74–7.86 (2H, m), 7.92 (1H, s), 8.43 (1H, dd, J=2.6, 7.4 Hz).

IR (KBr): 3094, 1703, 1599, 1522 cm⁻¹.

Example 71

Production of N-ethyl-6-{4-[1-hydroxy-1-(1H-imidazol-4-yl)-2-methylpropyl]phenyl}-2-pyridinecarboxamide (i) Production of 6-bromo-N-ethyl-2-pyridinecarboxamide By the reaction in the same manner as in Example 55-(i) using 6-bromopicolinic acid (3.06 g), ethylamine hydrochloride (2.49 g), triethylamine (6 ml), 1-[3-(dimethylamino)propyl]-3-ethylcarbodiimide hydrochloride (3.61 g) and 1-hydroxybenzotriazole (2.66 g), the title compound (3.20 g) was obtained as a colorless oil.

¹H-NMR (CDCl₃) δ: 1.28 (3H, t, J=7.3 Hz), 3.40–3.64 (2H, m), 7.60 (1H, d, J=7.9 Hz), 7.72 (1H, t, J=7.9 Hz), 7.82 (1H, brs), 8.16 (1H, d, J=7.9 Hz).

IR (KBr): 2975, 1669, 1557, 1532, 1427 cm⁻¹.

(ii) Production of N-ethyl-6-{4-[1-hydroxy-2-methyl-1-(1-trityl-1H-imidazol-4-yl)propyl]phenyl}-2-pyridinecarboxamide By the reaction in the same manner as in Example 33-(ii) using 4-[1-hydroxy-2-methyl-1-(1-trityl-1H-imidazol-4-yl)propyl]phenylboronic acid (3.10 g), 6-bromo-N-ethyl-2-pyridinecarboxamide (1.20 g) and tetrakis(triphenylphosphine)palladium(0) (0.170 g), the title compound (1.89 g) was obtained as colorless powder crystals.

¹H-NMR (CDCl₃) δ: 0.77 (3H, d, J=7.0 Hz), 0.93 (3H, d, J=7.0 Hz), 1.31 (3H, t, J=7.3 Hz), 2.40–2.60 (1H, m), 3.44–3.64 (2H, m), 3.54 (1H, s), 6.79 (1H, d, J=1.6 Hz), 7.08–7.19 (6H, m), 7.28–7.39 (10H, m), 7.66 (2H, d, J=8.8 Hz), 7.79–7.96 (4H, m), 8.13 (1H, dd, J=1.4, 7.4 Hz).

IR (KBr): 1671, 1524, 1449 cm⁻¹.

(iii) Production of N-ethyl-6-{4-[1-hydroxy-1-(1H-imidazol-4-yl)-2-methylpropyl]phenyl}-2-pyridinecarboxamide By the reaction in the same manner as in Example 4-(iii) using N-ethyl-6-{4-[1-hydroxy-2-methyl-1-(1-trityl-1H-imidazol-4-yl)propyl]phenyl}-2-pyridinecarboxamide (1.82 g) and pyridine hydrochloride (570 mg), the title compound (560 mg) was obtained as colorless powder crystals.

¹H-NMR (CDCl₃) δ: 0.84 (3H, d, J=6.6 Hz), 1.00 (3H, d, J=6.6 Hz), 1.29 (3H, t, J=7.3 Hz), 2.56–2.78 (1H, m), 3.44–3.64 (2H, m), 7.01 (1H, d, J=1.2 Hz), 7.55 (1H, d, J=1.2 Hz), 7.69 (2H, d, J=8.6 Hz), 7.77–7.88 (2H, m), 7.93 (2H, d, J=8.6 Hz), 8.10 (1H, dd, J=1.4, 7.0 Hz), 8.18 (1H, brs).

IR (KBr): 3441, 3395, 2975, 1676, 1530, 1449 cm⁻¹.

Example 72

Production of 6-{4-[1-hydroxy-1-(1H-imidazol-4-yl)-2-methylpropyl]phenyl}-N-isopropyl-2-pyridinecarboxamide (i) Production of 6-bromo-N-isopropyl-2-pyridinecarboxamide By the reaction in the same manner as in Example 55-(i) using 6-bromopicolinic acid (3.04 g), isopropylamine (5 ml), 1-[3-(dimethylamino)propyl]-3-ethylcarbodiimide hydrochloride (3.44 g) and 1-hydroxybenzotriazole (2.70 g), the title compound (3.10 g) was obtained as a colorless oil.

¹H-NMR (CDCl₃) δ: 1.29 (6H, d, J=6.6 Hz), 4.10–4.40 (1H, m), 7.60 (1H, dd, J=1.2, 7.8 Hz), 7.71 (1H, t, J=7.8 Hz), 8.16 (1H, dd, J=1.2, 7.8 Hz).

IR (KBr): 2973, 1674, 1557, 1520 cm⁻¹.

(ii) Production of 6-{4-[1-hydroxy-2-methyl-1-(1-trityl-1H-imidazol-4-yl)propyl]phenyl}-N-isopropyl-2-pyridinecarboxamide By the reaction in the same manner as in Example 33-(ii) using 4-[1-hydroxy-2-methyl-1-(1-trityl-1H-imidazol-4-yl)propyl]phenylboronic acid (3.10 g), 6-bromo-N-isopropyl-2-pyridinecarboxamide (1.13 g) and tetrakis(triphenylphosphine)palladium(0) (0.160 g), the title compound (1.67 g) was obtained as a colorless amorphous powder.

¹H-NMR (CDCl₃) δ: 0.78 (3H, d, J=6.6 Hz), 0.94 (3H, d, J=6.6 Hz), 1.32 (6H, d, J=6.6 Hz), 2.40–2.58 (1H, m), 3.56 (1H, s), 4.20–4.42 (1H, m), 6.80 (1H, s), 7.00–7.20 (6H, m), 7.21–7.46 (10H, m), 7.66 (2H, d, J=8.5 Hz), 7.79–7.86 (1H, m), 7.92 (2H, d, J=8.5 Hz), 8.04 (1H, d, J=7.4 Hz), 8.14 (1H, dd, J=1.0, 6.2 Hz).

IR (KBr): 3382, 2969, 1667, 1524, 1447 cm⁻¹.

(iii) Production of 6-{4-[1-hydroxy-1-(1H-imidazol-4-yl)-2-methylpropyl]phenyl}-N-isopropyl-2-pyridinecarboxamide By the reaction in the same manner as in Example 4-(iii) using 6-{4-[1-hydroxy-2-methyl-1-(1-trityl-1H-imidazol-4-yl)propyl]phenyl}-N-isopropyl-2-pyridinecarboxamide (1.60 g) and pyridine hydrochloride (770 mg), the title compound (350 mg) was obtained as colorless powder crystals.

¹H-NMR (CDCl₃) δ: 0.80 (3H, d, J=6.6 Hz), 0.97 (3H, d, J=6.6 Hz), 1.25 (6H, d, J=6.6 Hz), 2.44–2.70 (2H, m), 6.93 (1H, d, J=0.9 Hz), 7.41 (1H, d, J=7.8 Hz), 7.46 (1H, d, J=0.9 Hz), 7.60 (2H, d, J=8.4 Hz), 7.73 (1H, t, J=7.8 Hz), 7.84 (2H, d, J=8.4 Hz), 8.15 (1H, d, J=7.8 Hz), 8.15 (1H, brs).

IR (KBr): 2973, 1672, 1518, 1447 cm⁻¹.

Example 73

Production of 2-{4-[1-hydroxy-1-(1H-imidazol-4-yl)-2-methylpropyl]phenyl}-N-methylisonicotinamide (i) Production of 2-bromo-N-methylisonicotinamide By the reaction in the same manner as in Example 55-(i) using 2-bromoisonicotinic acid (2.69 g), a solution (2.0 M;

15 ml) of methylamine in THF, 1-[3-(dimethylamino) propyl]-3-ethylcarbodiimide hydrochloride (3.20 g) and 1-hydroxybenzotriazole (2.59 g), the title compound (361 mg) was obtained as colorless powder crystals.

$^1$H-NMR (CDCl$_3$) δ: 3.04 (3H, d, J=4.6 Hz), 7.55 (1H, dd, J=1.4, 5.1 Hz), 7.79–7.82 (1H, m), 8.49 (1H, d, J=5.1 Hz).

IR (KBr): 3291, 1644, 1557, 1537 cm$^{-1}$.

(ii) Production of 2-{4-[1-hydroxy-2-methyl-1-(1-trityl-1H-imidazol-4-yl)propyl]phenyl}-N-methylisonicotinamide By the reaction in the same manner as in Example 33-(ii) using 4-[1-hydroxy-2-methyl-1-(1-trityl-1H-imidazol-4-yl) propyl]phenylboronic acid (1.30 g), 2-bromo-N-methylisonicotinamide (310 mg) and tetrakis (triphenylphosphine)palladium(0) (0.110 g), the title compound (480 mg) was obtained as a colorless amorphous powder.

$^1$H-NMR (CDCl$_3$) δ: 0.74 (3H, d, J=6.6 Hz), 0.92 (3H, d, J=6.6 Hz), 2.36–2.54 (1H, m), 3.06 (3H, d, J=4.8 Hz), 3.61 (1H, s), 6.36 (1H, brs), 6.78 (1H, d, J=1.4 Hz), 7.06–7.18 (6H, m), 7.28–7.38 (10H, m), 7.45 (1H, dd, J=1.4, 5.2 Hz), 7.61 (2H, d, J=8.4 Hz), 7.93 (2H, d, J=8.4 Hz), 8.05–8.20 (1H, m), 8.75 (1H, dd, J=0.6, 5.2 Hz).

IR (KBr): 3304, 1651, 1549 cm$^{-1}$.

(iii) Production of 2-{4-[1-hydroxy-1-(1H-imidazol-4-yl)-2-methylpropyl]phenyl}-N-methylisonicotinamide By the reaction in the same manner as in Example 4-(iii) using 2-{4-[1-hydroxy-2-methyl-1-(1-trityl-1H-imidazol-4-yl)propyl]phenyl}-N-methylisonicotinamide (0.450 g) and pyridine hydrochloride (230 mg), the title compound (110 mg) was obtained as a colorless amorphous powder.

$^1$H-NMR (CDCl$_3$+CD$_3$OD) δ: 0.79 (3H, d, J=6.6 Hz), 0.98 (3H, d, J=6.6 Hz), 2.52–2.76 (1H, m), 3.02 (3H, s), 6.95 (1H, d, J=1.0 Hz), 7.44–7.60 (4H, m), 7.81 (2H, d, J=8.4 Hz), 7.97 (1H, s), 8.67 (1H, d, J=5.2 Hz).

IR (KBr): 3175, 2973, 1651, 1549 cm$^{-1}$.

Example 74

Production of N-[4'-fluoro-5-[1-hydroxy-1-(1H-imidazol-4-yl)-2-methylpropyl][1,1'-biphenyl]-2-yl] acetamide (i) Production of 4'-fluoro[1,1'-biphenyl]-2-yl methyl ether By the reaction in the same manner as in Example 4-(ii) using 2-bromoanisole (8.91 g), 4-fluorophenylboronic acid (10.0 g), 2M aqueous sodium carbonate solution (47.6 ml) and tetrakis(triphenylphosphine)palladium(0) (2.20 g), the title compound (8.14 g) was obtained as colorless needle crystals.

$^1$H-NMR (CDCl$_3$) δ: 3.81 (3H, s), 6.96–7.13 (4H, m), 7.27–7.37 (2H, m), 7.45–7.33 (2H, m).

IR (KBr): 1514, 1487, 1260, 1236, 1223, 1159, 1028, 835, 754 cm$^{-1}$.

(ii) Production of 5-bromo-4'-fluoro[1,1'-biphenyl]-2-ol

A mixture of 4'-fluoro[1,1'-biphenyl]-2-yl methyl ether (107 g), pyridinium hydrobromide perbromide (34.0 g) and water-acetic acid-diethyl ether mixed solution (1:4:5, 500 ml) was stirred for 18 h at room temperature. Hypowater was added to the reaction mixture and the mixture was concentrated. The resulting crystals were collected by filtration to give a crude product (15.2 g) of 5-bromo-4'-fluoro [1,1'-biphenyl]-2-yl methyl ether as a yellow solid. To a solution of this product (14.1 g) in dichloromethane (150 ml) was added dropwise a solution of boron tribromide (5.69 ml) in dichloromethane (40 ml) at −78° C., and the mixture was stirred at room temperature ifor 18 h. The reaction mixture was poured into ice and the organic layer was separated, neutralized with aqueous sodium hydrogen carbonate, washed with brine and dried over anhydrous sodium sulfate. The solvent was evaporated under reduced pressure and the residue was purified by silica gel chomatography (eluent;hexane→hexane:ethyl acetate=5:1) to give the title compound (13.2 g) as a colorless oil.

$^1$H-NMR (CDCl$_3$) δ: 5.11 (1H, s), 6.83–6.86 (1H, m), 7.13–7.24 (2H, m), 7.32–7.46 (4H, m).

IR (KBr): 1514, 1487, 1480, 1260, 1229, 1159, 839, 812 cm$^{-1}$.

(iii) Production of 4'-fluoro-5-[1-hydroxy-2-methyl-1-(1-trityl-1H-imidazol-4-yl)propyl] [1,1'-biphenyl]-2-ol To a solution of 5-bromo-4'-fluoro[1,1'-biphenyl]-2-ol (13.2 g) and imidazole (5.04 g) in DMF (60 ml) was added at 0° C. t-butyldimethylsilyl chloride (7.82 g), and the mixture was stirred at room temperature for 21 h. Water was added to the reaction mixture and the mixture was extracted with ethyl acetate, washed twice with water and with brine, and dried over anhydrous sodium sulfate. The solvent was evaporated under reduced pressure to give a crude product (18.1 g) of 3-bromo-6-[[tert-butyl(dimethyl)silyl]oxy]-4'-fluoro-1,1'-biphenyl as a yellow oil. By the reaction in the same manner as in Example 4-(i) using this product (18.1 g), a solution (1.6 M; 31.3 ml) of n-butyllithium in hexane and 2-methyl-1-(1-trityl-1H-imidazol-4-yl)-1-propane (12.0 g), a colorless amorphous and crude product (18.2 g) of 1-[4'-fluoro-6-[[tert-butyl(dimethyl)silyl]oxy][1,1'-biphenyl]-3-yl]-2-methyl-1-(1-trityl-1H-imidazol-4-yl)-1-propanol was obtained. To a solution of this product (18.2 g) in THF (100 ml) was added dropwise a solution (1.0 M; 27.7 ml) of tetrabutylammonium bromide in THF at 0° C., and the mixture was stirred at room temperature for 15 h. Water and ethyl acetate were added to the reaction mixture and the mixture was concentrated. Ethyl acetate and diisopropyl ether were added to the residue and the precipitated crystals were collected by filtration, washed with diisopropyl ether and dried under reduced pressure to give the title compound (11.2 g) as a colorless powder.

$^1$H-NMR (DMSO-d$_6$) δ: 0.65 (3H, d, J=6.6 Hz), 0.73 (3H, d, J=6.6 Hz), 2.44–2.51 (1H, m), 4.92 (1H, s), 6.78–6.83 (2H, m), 7.04–7.08 (7H, m), 7.16–7.55 (15H, m), 9.37 (1H, s).

IR (KBr): 1501, 1271, 1223, 1184, 1157, 1001, 835, 756, 748, 702 cm$^{-1}$.

(iv) Production of 4'-fluoro-5-[1-hydroxy-2-methyl-1-(1-trityl-1H-imidazol-4-yl)propyl][1,1'-biphenyl]-2-yl trifluoromethanesulfonate To a solution of 4'-fluoro-5-(hydroxy-2-methyl-1-(1-trityl-1H-imidazol-4-yl)propyl][1,1'-biphenyl]-2-ol (1.10 g) in pyridine (7 ml) was added dropwise at 0° C. trifluoromethanesulfonic anhydride (0.423 ml), and the mixture was stirred at 0° C. for 20 min and at room temperature for 40 min. The reaction mixture was concentrated under reduced pressure, diluted with ethyl acetate. The mixture was washed 3 times with 5% aqueous citric acid solution, and with water, saturated aqueous sodium hydrogen carbonate and saturated brine, and dried over anhydrous magnesium sulfate. The solvent was evaporated under reduced pressure, and the residue was purified by silica gel chomatography (eluent;hexane:ethyl acetate=5:1) to give the colorless amorphous title compound (1.06 g).

$^1$H-NMR (CDCl$_3$) δ: 0.73 (3H, d, J=6.6 Hz), 0.92 (3H, d, J=6.6 Hz), 2.35–2.42 (1H, m), 3.74 (1H, s), 6.74 (1H, d, J=1.6 Hz), 7.08–7.17 (7H, m), 7.24–7.40 (14H, m), 7.52–7.61 (2H, m).

IR (KBr): 1481, 1424, 1248, 1217, 1161, 1140, 885, 837, 747, 702 cm$^{-1}$.

(v) Production of 1-[6-[(diphenylmethylene)amino]-4'-fluoro[1,1'-biphenyl]-3-yl]-2-methyl-1-(1-trityl-1H-imidazol-4-yl)-1-propanol To a solution of 4'-fluoro-5-[1-hydroxy-2-methyl-1-(1-trityl-1H-imidazol-4-yl)propyl][1,1'-biphenyl]-2-yl trifluoromethanesulfonate (1.06 g), benzophenone imine (0.035 ml) and cecium carbonate (1.23 g) in toluene (15 ml) were added (RS)-2,2'-bis(diphenylphosphino)-1,1'-binaphthyl (56.4 mg) and tri(dibenzylideneacetone)dipalladium(0) (27.7 mg), and the mixture was stirred at 80–90° C. for 26 h. (RS)-2,2'-Bis(diphenylphosphino)-1,1'-binaphthyl (112 mg) and tri(dibenzylideneacetone)palladium(0) (55.4 mg) were further added, and the mixture was stirred at 80–90° C. for 16.5 h, and at 105° C. for 3.5 h. The reaction mixture was filtered through Celite, and the filtrate was washed with water and saturated brine and dried over anhydrous magnesium sulfate. The solvent was evaporated under reduced pressure and the residue was purified by silica gel chomatography (eluent; hexane:ethyl acetate=5:1→1:1) to give the yellow amorphous title compound (115 mg).

$^1$H-NMR (CDCl$_3$) δ: 0.69 (3H, d, J=6.6 Hz), 0.88 (3H, d, J=7.0 Hz), 2.28–2.35 (1H, m), 3.60 (1H, s), 6.60–6.66 (3H, m), 6.82–7.44 (29H, m), 7.60–7.64 (2H, m).

IR (KBr): 1599, 1510, 1491, 1480, 1447, 1223, 1157, 909, 837, 747, 735, 700 cm$^{-1}$.

(vi) Production of N-[4'-fluoro-5-[1-hydroxy-2-methyl-1-(1-trityl-1H-imidazol-4-yl)propyl][1,1'-biphenyl]-2-yl]acetamide To a solution of 1-[6-[(diphenylmethylene)amino]-4'-fluoro[1,1'-biphenyl]-3-yl]-2-methyl-1-(1-trityl-1H-imidazol-4-yl)-1-propanol (110 mg) in THF-methanol (1:1) (6 ml) were added anhydrous sodium acetate (29.6 mg) and hydroxyammonium chloride (18.7 mg) at room temperature, and the mixture was stirred for 22 h. The reaction mixture was concentrated, diluted with ethyl acetate, washed with 0.5N aqueous sodium hydroxide solution and saturated brine and dried over anhydrous magnesium sulfate. The solvent was evaporated under reduced pressure to give a crude product (118 mg) of 1-[6-amino-4'-fluoro[1,1'-biphenyl]-3-yl]-2-methyl-1-(1-trityl-1H-imidazol-4-yl)-1-propanol as a yellow oil. To a solution of this product (116 mg) and pyridine (29.6 μl) in THF (2 ml) was added dropwise acetic anhydride (28.3 μl) at 0° C., and the mixture was stirred at room temperature for 16 h. Saturated aqueous sodium hydrogen carbonate was added to the reaction mixture and the mixture was washed with saturated brine and dried over anhydrous magnesium sulfate. The solvent was evaporated under reduced pressure and the residue was purified by silica gel chomatography (eluent; hexane:ethyl acetate=3:1→3:2) to give the colorless amorphous title compound (79.6 mg).

$^1$H-NMR (CDCl$_3$) δ: 0.75 (3H, d, J=6.6 Hz), 0.91 (3H, d, J=6.6 Hz), 2.02 (3H, s), 2.30–2.41 (1H, m), 3.64 (1H, s), 6.73 (1H, d, J=1.6 Hz), 6.96 (1H, br s), 7.09–7.19 (8H, m), 7.29–7.39 (14H, m), 8.09 (1H, d, J=8.8 Hz).

IR (KBr): 1669, 1514, 1493, 1472, 1447, 1225, 1159, 747, 733, 702 cm$^{-1}$.

(vii) Production of N-[4'-fluoro-5-[1-hydroxy-1-(1H-imidazole-4-imidazole)-2-methylpropyl][1,1'-biphenyl]-2-yl]acetamide By the reaction in the same manner as in Example 4-(iii) using N-[4'-fluoro-5-[1-hydroxy-2-methyl-1-(1-trityl-1H-imidazol-4-yl)propyl][1,1'-biphenyl]-2-yl]acetamide (78.2 mg) and pyridine hydrochloride (26.7 mg), the title compound (25.0 mg) was obtained as colorless needle crystals.

$^1$H-NMR (CDCl$_3$) δ: 0.83 (3H, d, J=6.8 Hz), 0.95 (3H, d, J=6.6 Hz), 2.02 (3H, s), 2.52–2.66 (1H, m), 6.95 (1H, br s) 7.10–7.19 (1H, m), 7.29–7.36 (3H, m), 7.47–7.52 (3H, m), 8.11 (1H, d, J=8.8 Hz).

IR (KBr): 3169, 2973, 1665, 1514, 1491, 1304, 1225, 839, 820 cm$^{-1}$.

Example 75

Production of 4'-fluoro-5-[1-hydroxy-1-(1H-imidazol-4-yl)-2-methylpropyl][1,1'-biphenyl]-2-yl acetate (i) Production of benzyl 5-bromo-4'-fluoro[1,1'-biphenyl]-2-yl ether A solution of 5-bromo-4'-fluoro[1,1'-biphenyl]-2-ol (7.00 g), potassium carbonate (3.80 g) and benzyl bromide (3.27 ml) in DMF (10 ml) was stirred at 60° C. for 5 h. The reaction mixture was diluted with water, extracted with ethyl acetate, washed with water and saturated brine and dried over anhydrous magnesium sulfate. The solvent was evaporated under reduced pressure and the residue was purified by silica gel chomatography (eluent; hexane→hexane:ethyl acetate=10:1) to give the title compound (8.31 g) as a brown oil.

$^1$H-NMR (CD$_3$OD) δ: 5.05 (2H, s), 6.89 (1H, d, J=8.8 Hz), 7.04–7.14 (2H, m), 7.25–7.55 (9H, m).

IR (KBr): 1512, 1483, 1454, 1265, 1227, 1159, 1024, 837, 737 cm$^{-1}$.

(ii) Production of 1-[6-benzyloxy-4'-fluoro[1,1'-biphenyl]-3-yl]-2-methyl-1-(1-trityl-1H-imidazol-4-yl)-1-propanol By the reaction in the same manner as in Example 4-(i) using benzyl 5-bromo-4'-fluoro[1,1'-biphenyl]-2-yl ether (3.86 g), a solution (1.6 M; 7.29 ml) of n-butyllithium in hexane and 1-(1H-imidazol-4-yl)-2-methyl-1-propane (597 mg), the colorless amorphous title compound (672 mg) was obtained.

$^1$H-NMR (CDCl$_3$) δ: 0.84 (3H, d, J=7.0 Hz), 0.96 (3H, d, J=6.6 Hz), 2.53–2.67 (1H, m), 5.05 (2H, s), 6.94–7.10 (4H, m), 7.30–7.33 (5H, m), 7.43–7.56 (5H, m).

IR (KBr): 1514, 1491, 1265, 1225, 1157, 1017, 837, 735 cm$^{-1}$.

(iii) Production of 4'-fluoro-5-[1-hydroxy-1-(1H-imidazol-4-yl)-2-methylpropyl][1,1'-biphenyl]-2-ol A suspension of 1-[6-benzyloxy-4'-fluoro[1,1'-biphenyl]-3-yl]-2-methyl-1-(1-trityl-1H-imidazol-4-yl)-1-propanol (647 mg) and 10% palladium carbon (647 mg) in methanol (15 ml) was stirred under a hydrogen atmosphere at room temperature for 4 h. The reaction mixture was filtered through Celite and the filtrate was concentrated. The residue was purified by silica gel chomatography (eluent; ethyl acetate→ethyl acetate:methanol=20:1). Recrystallization from ethyl acetate-hexane gave the title compound (396 mg) as colorless powder crystals.

$^1$H-NMR (CDCl$_3$+CD$_3$OD) δ: 0.83 (3H, d, J=7.0 Hz), 0.95 (3H, d, J=7.0 Hz), 2.52–2.65 (1H, m), 6.65 (1H, d, J=8.4 Hz), 6.94 (1H, d, J=1.2 Hz), 7.04–7.14 (2H, m), 7.26 (1H, d, J=2.2, 8.4 Hz), 7.34 (1H, d, J=2.2 Hz), 7.47–7.54 (3H, m).

IR (KBr): 1514, 1493, 1229, 1213, 1007, 841, 814, 627, 606 cm$^{-1}$.

(iv) Production of 4'-fluoro-5-[1-hydroxy-1-(1H-imidazol-4-yl)-2-methylpropyl][1,1'-biphenyl]-2-yl acetate To a solution of 4'-fluoro-5-[1-hydroxy-1-(1H-imidazol-4-yl)-2-methylpropyl][1,1'-biphenyl]-2-ol (390 mg) in pyridine (4 ml) was added dropwise acetic anhydride (0.135 ml) at room temperature, and the mixture was stirred for 4 h. Acetic anhydride (22.5 μl) was further added and the mixture was stirred for 15 h. The reaction mixture was subjected to azeotropic reaction with toluene for concentration, diluted with ethyl acetate, washed with water and saturated brine and dried over anhydrous magnesium sulfate. The solvent was evaporated under reduced pressure and to a solution of the residue (414 mg) in pyridine (4 ml) was added dropwise acetic anhydride (0.209 ml) at room temperature. The mixture was stirred for 15 h and the reaction mixture was subjected to azeotropic reaction with toluene for concentration. To a solution of the residue in methanol (15 ml) was added 0.1N aqueous p-toluenesulfonic acid solution (7.5 ml) at room temperature, and the mixture was stirred for 1 h. The reaction mixture was concentrated, diluted with ethyl acetate, neutralized with saturated aqueous sodium hydrogen carbonate, extracted with ethyl acetate, washed with saturated brine and dried over anhydrous magnesium sulfate. The solvent was evaporated under reduced pressure and the residue was purified by column chomatography (eluent; ethyl acetate→ethyl acetate:methanol=20:1) to give the colorless amorphous title compound (337 mg).

$^1$H-NMR (CDCl$_3$+CD$_3$OD) δ: 0.83 (3H, d, J=6.6 Hz), 0.96 (3H, d, J=6.6 Hz), 2.08 (3H, s), 2.57–2.65 (1H, m), 6.96 (1H, d, J=1.0 Hz), 7.03–7.11 (3H, m), 7.32–7.39 (2H, m), 7.50–7.59 (3H, m).

IR (KBr): 1748, 1516, 1487, 1372, 1223, 1196, 1161, 839 cm$^{-1}$.

Example 76

Production of 5-[4-[1-hydroxy-1-(1H-imidazol-4-yl)-2-methylpropyl]phenyl]-N-methyl-2-thiophenecarboxamide (i) Production of 5-[4-[1-hydroxy-2-methyl-1-(1-trityl-1H-imidazol-4-yl)propyl]phenyl]-N-methyl-2-thiophenecarboxamide By the reaction in the same manner as in Example 33-(ii) using 5-bromo-N-methyl-2-thiophenecarboxamide (1.01 g), a crude product (3.00 g) of 4-[1-hydroxy-2-methyl-1-(1-trityl-1H-imidazol-4-yl)propyl]phenylboronic acid, 2M aqueous sodium carbonate solution (4.59 ml) and tetrakis (triphenylphosphine)palladium(0) (265 mg), the title compound (1.44 g) was obtained as colorless powder crystals.

$^1$H-NMR (CDCl$_3$) δ: 0.75 (3H, d, J=6.8 Hz), 0.92 (3H, d, J=7.0 Hz), 2.43–2.47 (1H, m), 3.01 (3H, d, J=4.8 Hz), 3.53 (1H, s), 5.93 (1H, br s), 6.76 (1H, d, J=1.4 Hz), 7.10–7.15 (7H, m), 7.24–7.53 (15H, m).

IR (KBr): 1626, 1553, 1493, 1449, 810, 747, 733, 702 cm$^{-1}$.

(ii) Production of 5-[4-[1-hydroxy-1-(1H-imidazol-4-yl)-2-methylpropyl]phenyl]-N-methyl-2-thiophenecarboxamide By the reaction in the same manner as in Example 4-(iii) using 5-[4-[1-hydroxy-2-methyl-1-(1-trityl-1H-imidazol-4-yl)propyl]phenyl]-N-methyl-2-thiophenecarboxamide (1.39 g) and pyridine hydrochloride (484 mg), the colorless amorphous title compound (769 mg) was obtained.

$^1$H-NMR (CDCl$_3$+CD$_3$OD) δ: 0.82 (3H, d, J=6.6 Hz), 0.97 (3H, d, J=7.0 Hz), 2.59–2.66 (1H, m), 2.97 (3H, s), 6.96 (1H, d, J=0.8 Hz), 7.22 (1H, d, J=4.0 Hz), 7.47 (1H, d, J=4.0 Hz), 7.54–7.56 (5H, m).

IR (KBr): 3079, 1626, 1557, 1528, 1451, 1410, 1314, 812 cm$^{-1}$.

Example 77

Production of 5-[4-[1-hydroxy-1-(1H-imidazol-4-yl)-2-methylpropyl]phenyl]-N-methyl-2-thiophenesulfonamide (i) Production of 5-[4-[1-hydroxy-2-methyl-1-(1-trityl-1H-imidazol-4-yl)propyl]phenyl]-N-methyl-2-thiophenesulfonamide By the reaction in the same manner as in Example 33-(ii) using 5-bromo-N-methyl-2-thiophenesulfonamide (1.18 g), a crude product (3.00 g) of 4-[1-hydroxy-2-methyl-1-(1-trityl-1H-imidazol-4-yl)propyl]phenylboronic acid, 2M aqueous sodium carbonate solution (4.59 ml) and tetrakis (triphenylphosphine)palladium(0) (265 mg), the title compound (1.67 g) was obtained as colorless needle crystals.

$^1$H-NMR (CDCl$_3$) δ: 0.74 (3H, d, J=7.0 Hz), 0.92 (3H, d, J=6.6 Hz), 2.40–2.47 (1H, m), 2.78 (3H, d, J=5.6 Hz), 3.54 (1H, s), 4.44 (1H, q J=5.6 Hz), 6.76 (1H, d, J=1.2 Hz), 7.10–7.15 (6H, m), 7.22–7.35 (11H, m), 7.48–7.58 (5H, m).

IR (KBr): 1445, 1335, 1159, 808, 747, 733, 702, 594 cm$^{-1}$.

(ii) Production of 5-[4-[1-hydroxy-1-(1H-imidazol-4-yl)-2-methylpropyl]phenyl]-N-methyl-2-thiophenesulfonamide By the reaction in the same manner as in Example 4-(iii) using 5-[4-[1-hydroxy-2-methyl-1-(1-trityl-1H-imidazol-4-yl)propyliphenyl]-N-methyl-2-thiophenesulfonamide (1.62 g) and pyridine hydrochloride (532 mg), the colorless amorphous title compound (884 mg) was obtained.

$^1$H-NMR (CDCl$_3$+CD$_3$OD) δ: 0.80 (3H, d, J=6.6 Hz), 0.97 (3H, d, J=6.6 Hz), 2.56–2.72 (4H, m), 6.97 (1H, s), 7.21 (1H, d, J=4.0 Hz), 7.30 (1H, s), 7.48–7.58 (5H, m).

IR (KBr): 1435, 1327, 1157, 1134, 1090, 1015, 806, 594 cm$^{-1}$.

Example 78

Production of 4-[4-[1-hydroxy-1-(1H-imidazol-4-yl)-2-methylpropyl]phenyl]]-1-isoindolinone (i) Production of methyl 3-bromo-2-methylbenzoate A solution of 3-bromo-2-methylbenzoic acid (9.95 g) and conc. sulfuric acid (0.2 ml) in methanol (50 ml) was stirred at room temperature for 69 h and heated under reflux for 96 h. The reaction mixture was neutralized with 1N aqueous sodium hydroxide solution and concentrated. The residue was diluted with ethyl acetate, washed 3 times with 1N aqueous sodium hydroxide solution and with saturated brine and dried over anhydrous magnesium sulfate. The solvent was evaporated under reduced pressure to give the title compound (10.2 g) as a colorless oil.

$^1$H-NMR (CDCl$_3$) δ: 2.65 (3H, s), 3.93 (3H, s), 7.12 (1H, dd, J=8.0, 8.0 Hz), 7.69–7.77 (2H, m).

IR (KBr): 1728, 1435, 1285, 1256, 1215, 1098, 754 cm$^{-1}$.

(ii) Production of methyl 3-bromo-2-(bromomethyl) benzoate

A solution of methyl 3-bromo-2-methylbenzoate (1.00 g), N-bromosuccinimide (855 mg) and 2,2'-azobis (isobutyronitrile) (71.8 mg) in carbon tetrachloride (50 ml) was heated under reflux for 8 h. The reaction mixture was concentrated, and the residue was diluted with ethyl acetate, washed with saturated aqueous sodium hydrogen carbonate and saturated brine and dried over anhydrous magnesium sulfate. The solvent was evaporated under reduced pressure and the residue was purified by column chomatography (eluent; hexane:ethyl acetate=20:1) to give the title compound (1.29 g) as a colorless oil.

$^1$H-NMR (CDCl$_3$) δ: 3.96 (3H, s), 5.14 (2H, s), 7.23 (1H, dd, J=6.8, 6.8 Hz), 7.77 (1H, dd, J=1.2, 6.8 Hz), 7.89 (1H, dd, J=1.2, 6.8 Hz).

IR (KBr): 1725, 1435, 1291, 1264, 1223, 1115, 760 cm$^{-1}$.

(iii) Production of 4-bromo-1-isoindolinone

Methyl 3-bromo-2-(bromomethyl)benzoate (1.28 g) was dissolved in a 11% solution of ammonia in methanol-THF mixed solution (3:2, 25 ml) and the mixture was stirred at room temperature for 16 h. The reaction mixture was concentrated and the residue was washed with saturated brine. Recrystallization from ethyl acetate-hexane gave the title compound (671 mg, 76%) as colorless needle crystals.

$^1$H-NMR (CDCl$_3$) δ: 4.42 (2H, s), 7.42 (1H, dd, J=7.8, 7.8 Hz), 7.48 (1H, br s), 7.73 (1H, d, J=7.8 Hz), 7.85 (1H, d, J=7.8 Hz).

IR (KBr): 3167, 1728, 1684, 1667, 1470, 1462, 1107, 745 cm$^{-1}$.

(iv) Production of 4-[4-[1-hydroxy-2-methyl1-(1-trityl-1H-imidazol-4-yl)-propyl]phenyl]]-1-isoindolinone By the reaction in the same manner as in Example 33-(ii) using 4-bromo-1-isoindolinone (620 mg), a crude product (2.06 g) of 4-[1-hydroxy-2-methyl-1-(1-trityl-1H-imidazol-4-yl)propyl]phenylboronic acid, 2M aqueous sodium carbonate solution (2.92 ml) and tetrakis(triphenylphosphine) palladium(0) (169 mg), the title compound (1.07 g) was obtained as colorless needle crystals.

$^1$H-NMR (CDCl$_3$) δ: 0.77 (3H, d, J=6.6 Hz), 0.94 (3H, d, J=6.6 Hz), 2.42–2.49 (1H, m), 3.60 (1H, s), 4.51 (2H, s), 6.38 (1H, br s), 6.79 (1H, d, J=1.0 Hz), 7.11–7.16 (6H, m), 7.32–7.39 (12H, m), 7.55–7.62 (4H, m), 7.85 (1H, dd, J=2.2, 6.2 Hz).

IR (KBr): 1694, 1491, 1478, 1445, 812, 756, 702 cm$^{-1}$.

(v) Production of 4-[4-[1-hydroxy-1-(1H-imidazol-4-yl)-2-methylpropyl]phenyl]]-1-isoindolinone A solution of 4-[4-[1-hydroxy-2-methyl1-(1-trityl-1H-imidazol-4-yl)propyl]phenyl]]-1-isoindolinone (1.02 g) in 90% formic acid-THF(1:1, 8 ml) was heated under reflux for 1.5 h. The reaction mixture was concentrated, and the residue was diluted with THF-ethyl acetate mixture (1:1), washed with saturated aqueous sodium hydrogen carbonate-saturated brine and dried over anhydrous magnesium sulfate. The solvent was evaporated under reduced pressure and the residue was purified by column chomatography (eluent; dichloromethane→dichloromethane:methanol=20:1→7:1) to give the colorless amorphous title compound (503 mg).

$^1$H-NMR (CDCl$_3$+CD$_3$OD) δ: 0.83 (3H, d, J=6.6 Hz), 0.99 (3H, d, J=6.6 Hz), 2.58–2.72 (1H, m), 4.46 (2H, s), 7.01 (1H, d, J=1.2 Hz), 7.37 (2H, d, J=8.4 Hz), 7.50–7.57 (3H, m), 7.62 (2H, d, J=8.6 Hz), 7.84 (1H, dd, J=2.2, 6.2 Hz).

IR (KBr): 1682, 1480, 1456, 862, 812, 756, 741 cm$^{-1}$.

Example 79

Production of (−)-N-(6-{4-[1-hydroxy-1-(1H-imidazol-4-yl)-2-methylpropyl]phenyl}-2-pyridyl) acetamide N-(6-{4-[1-Hydroxy-1-(1H-imidazol-4-yl)-2-methylpropyl]phenyl}-2-pyridyl)acetamide obtained in Example 68 was subjected to liquid chromatography (eluent; hexane:ethanol=9:1) using an optically active column (Chiralpak AD) to give (−)-N-(6-{4-[1-hydroxy-1-(1H-imidazol-4-yl)-2-methylpropyl]phenyl}-2-pyridyl) acetamide as an enantiomer of the first eluate.

Optical purity; >99.9% ee (Chiralpak AD)

$[α]_D^{20}$ −11.8° (C=1.02, methanol)

Formulation Example 1

Capsules

| | |
|---|---|
| (1) Compound obtained in Example 6 | 10 mg |
| (2) lactose | 90 mg |
| (3) microcrystalline cellulose | 70 mg |
| (4) magnesium stearate | 10 mg |

One Capsule 180 mg

The entire amount of the above (1), (2) and (3) and 5 mg of (4) were admixed. The mixture was granulated and the remaining 5 mg of (4) was added. The whole content was sealed in a gelation capsule.

Formulation Example 2

Tablets

| | |
|---|---|
| (1) Compound obtained in Example 9 | 10 mg |
| (2) lactose | 35 mg |
| (3) corn starch | 150 mg |
| (4) microcrystalline cellulose | 30 mg |
| (5) magnesium stearate | 5 mg |
| One Tablet | 230 mg |

The entire amount of above (1), (2) and (3), 20 mg of (4) and 2.5 mg of (5) were admixed. The mixture was granulated and remaining 10 mg of (4) and 2.5 mg of (5) were added. The mixture was compression formed to give a tablet.

Experimental Example 1

Assay of Inhibitory Activity on Rat Steroid C$_{17,20}$-lyase

The activity was determined according to The Prostate, vol. 26, 140–150 (1995).

Testes were excised from 13-week-old male SD rats, homogenized, and centrifuged to give microsomes. [1,2-

$^3$H]-17-α-hydroxyprogesterone having a final concentration of 10 nM, NADPH solution and test compounds were dissolved in 10 μl of 100 mM phosphate buffer (pH 7.4) and microsome protein (7 μg/10 μl) was added. The reaction mixture was incubated at 37° C. for 7 minutes. Ethyl acetate (40 μl) was added and the mixture was centrifuged. The substrate and the products (androstenedione and testosterone) in the supernatant were separated by silica gel thin layer chromatography (TLC). The spots were detected and quantitatively determined by BAS 2000 Bioimage analyzer. The concentration of the test compounds necessary to reduce the amount of the products by 50% (IC$_{50}$) relative to the amount of the products without test compound (control) as 100% was calculated, and shown in Table 1.

TABLE 1

| Test compounds | | IC$_{50}$ (nM) |
|---|---|---|
| Example 4 | [structure] | 28 |
| Example 6 | [structure] | 15 |
| Example 9 | [structure] | 10 |

TABLE 1-continued

| Test compounds | | IC$_{50}$ (nM) |
|---|---|---|
| Example 13 | [structure] | 8.3 |
| Example 17 | [structure] | 12 |
| Example 27 | [structure] | 11 |

Experimental Example 2

Assay of Inhibitory Activity on Testosterone Synthesis in Rats

Test compounds (50 mg/kg) were orally administered to 9-week-old male SD (Sprague Dawley) rats. Two hours after administration of the compounds, blood was drawn and testosterone concentration in the obtained serum was measured by radioimmunoassay. The percentage (T/C, %) of the testosterone concentration of test compounds administration group to that of the control group was calculated, and taken as the inhibitory activity on testosterone synthesis.

TABLE 2

| Test compounds | | testosterone synthesis inhibitory activity (T/C, %) |
|---|---|---|
| Example 6 | [structure] | 4.3 |

TABLE 2-continued

| Test compounds | testosterone synthesis inhibitory activity (T/C, %) |
|---|---|
| Example 9 | 4.6 |
| Example 13 | 4.7 |

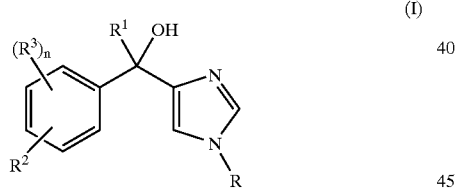

INDUSTRIAL APPLICABILITY

The compound of the present invention and a salt thereof have a steroid $C_{17,20}$-lyase inhibitory activity and are useful for the prophylaxis or treatment of various diseases such as primary tumor, its metastasis and recurrence thereof, various symptoms that accompany these cancers, prostatic hypertrophy, virilism, hirsutism, male pattern alopecia, precocious puberty, endometriosis, uterus myoma, mastopathy, polycystic ovary syndrome and the like in mammal, which are affected by sex steroids and metabolites thereof.

What is claimed is:

1. A compound represented by the formula:

(I)

wherein
R is a hydrogen atom or a protecting group,
$R^1$ is a lower alkyl group or a cyclic hydrocarbon group,
$R^2$ is an aromatic hydrocarbon group optionally having substituents or an aromatic heterocyclic group optionally having substituents,
$R^3$ is a hydrocarbon group optionally having substituents, a hydroxyl group optionally having substituents, a thiol group optionally having substituents, an amino group optionally having substituents, an acyl group or a halogen atom, and
n is an integer of 0 to 4,
or a salt thereof.

2. The compound of claim 1, wherein
R is (1) a hydrogen atom, (2) a formyl, (3) a $C_{1-6}$ alkylcarbonyl optionally substituted by 1 to 3 groups selected from Group 1, (4) a phenylcarbonyl optionally substituted by 1 to 3 groups selected from Group 1, (5) a $C_{1-6}$ alkyl-oxycarbonyl optionally substituted by 1 to 3 groups selected from Group 1, (6) a phenyloxycarbonyl optionally substituted by 1 to 3 groups selected from Group 1, (7) a $C_{7-10}$ aralkyloxy-carbonyl optionally substituted by 1 to 3 groups selected from Group 1, (8) a trityl optionally substituted by 1 to 3 groups selected from Group 1, (9) a phthaloyl optionally substituted by 1 to 3 groups selected from Group 1 or (10) a N,N-dimethylaminomethylene optionally substituted by 1 to 3 groups selected from Group 1, $R^1$ is a $C_{1-6}$ alkyl or a $C_{3-6}$ cycloalkyl, $R^2$ is a $C_{6-10}$ aryl group optionally substituted by 1 to 4 groups selected from Group 2 or an aromatic heterocyclic group selected from Group 3, which is optionally substituted by 1 to 4 groups selected from Group 2, and $R^3$ is (1) a $C_{1-4}$ alkyl, (2) a $C_{1-4}$ alkyl having $C_{2-4}$ alkanoyl, carboxyl or $C_{1-4}$ alkoxy-carbonyl as a substituent, (3) a hydroxyl group, (4) a $C_{1-4}$ lower alkoxy, (5) a $C_{1-4}$ alkanoyloxy, (6) a carbamoyloxy, (7) a carbamoyloxy substituted by 1 or 2 $C_{1-4}$ alkyl groups, (8) a thiol group, (9) a $C_{1-4}$ alkylthio group, (10) a $C_{1-4}$ alkanoylthio, (11) an amino group, (12) a $C_{1-4}$ alkylamino group, (13) a di-$C_{1-4}$ alkylamino, (14) a $C_{1-4}$ alkanoylamino, (15) a formyl, (16) a $C_{2-6}$ alkanoyl, (17) a $C_{1-4}$ alkylsulfonyl, (18) a carbamoyl group, (19) a mono- or di-$C_{1-10}$ alkylcarbamoyl group, (20) a mono- or di-$C_{6-4}$ arylcarbamoyl, (21) a mono- or di-$C_{7-16}$ aralkylcarbamoyl group, (22) a sulfamoyl, (23) a mono- or di-$C_{1-10}$ alkylsulfamoyl group, (24) a mono- or di-$C_{6-14}$ arylsulfamoyl group, (25) a mono- or di-$C_{7-16}$ aralkylsulfamoyl group or (26) a halogen atom, and wherein, in the above, Group 1 comprises a substituent selected from the group consisting of:
a halogen atom, a formyl group, a $C_{1-6}$ alkyl-carbonyl group and a nitro group, Group 2 comprises a substituent selected from the group consisting of:
(1) a $C_{1-6}$ alkyl group, (2) a $C_{1-4}$ alkyl group substituted by 1 to 5 halogen atoms, (3) a $C_{1-4}$ alkyl group substituted by 1 or 2 $C_{1-4}$ alkoxy, (4) a hydroxyl group, (5) a $C_{1-4}$ alkoxy group, (6) a $C_{1-4}$ alkanoyloxy group, (7) a carbamoyloxy group, (8) a carbamoyloxy group substituted by $C_{1-4}$ alkyl group, (9) an amino group, (10) a mono- or di-$C_{1-4}$ alkylamino group, (11) a $C_{1-4}$ alkanoylamino group, (12) a formyl group, (13) a $C_{2-6}$ alkanoyl group, (14) a $C_{1-4}$ alkylsulfonyl group, (15) a carbamoyl group, (16) a mono- or di-$C_{1-10}$ alkylcarbamqyl group, (17) a $C_{3-6}$ cycloalkylcarbamoyl group, (18) a mono- or di-$C_{6-14}$ arylcarbamoyl group, (19) a mono- or di-$C_{7-16}$ aralkylcarbamoyl group, (20) a sulfamoyl group, (21) a mono- or di-$C_{1-10}$ alkylsulfamoyl group, (22) a mono- or di-$C_{6-14}$ arylsulfamoyl group, (23) a mono- or di-$C_{7-16}$ aralkylsulfamoyl group, (24) a halogen atom, (25) a cyano group and 26) an oxo group, and Group 3 comprises a substituent selected from the group consisting of:

a 2-thienyl group, a 3-thienyl group, a 2-pyridyl group, a 3-pyridyl group, a 4-pyridyl group, a 2-turyl group, a 3-furyl group, a 2-quinolyl group, a 4-quinolyl group, a 8-quinolyl group, a 3-isoquinolyl group, a 4-isoquinolyl group, a pyrazinyl group, a 2-pyrimidinyl group, a 3-pyrrolyl group, a 1-imidazolyl group, a 2-imidazolyl group, a 1-pyrazolyl group, a 2-thiazolyl group, a 4-thiazolyl group, a 5-thiazolyl group, a 3-isothiazolyl group, a 4-isothiazolyl group, a 2-oxazolyl group, a 4-oxazolyl group, a 5-oxazolyl group, a 3-isoxazolyl group, a 3-pyridazinyl group, a 1-indolyl group, a 1-isoindolyl group, a 2-isoindolyl group, a 1-tetrazolyl group, a 2-tetrazolyl group and a 5-tetrazolyl group.

3. The compound of claim 1, wherein
R is a hydrogen atom,
$R^1$ is a $C_{1-6}$ alkyl group or a $C_{3-6}$ cycloalkyl group,
$R^2$ is a phenyl group, a pyridyl group, a thienyl group, a furyl group or an izoindolinyl group, each optionally substituted by 1 to 4 groups selected from Group 4,
n is 0 or 1, and
$R^3$ is a $C_{1-4}$ lower alkoxy group, a $C_{1-4}$ alkanoyloxy group or a $C_{1-4}$ alkanoylamino group,
and wherein, in the above, Group 4 comprises a substituent selected from the group consisting of:

(1) a $C_{1-6}$ alkyl group, (2) a $C_{1-4}$ alkyl group substituted by 1 to 5 halogen atoms, (3) a $C_{1-4}$ alkyl group substituted by 1 or 2 $C_{1-4}$ alkoxy, (4) a $C_{1-4}$ alkoxy group, (5) a $C_{1-4}$ alkanoylamino group, (6) a $C_{2-6}$ alkanoyl group, (7) a mono- or di-$C_{1-10}$ alkylcarbamoyl group, (8) a $C_{3-6}$ cycloalkylcarbamoyl group, (9) a mono- or di-$C_{1-10}$ alkylsulfamoyl group, (10) a halogen atom, (11) a cyano group and (12) an oxo group.

4. The compound of claim 3, wherein $R^2$ is a phenyl group, a pyridyl group, a thienyl group, a furyl group or an isoindolinyl group, each optionally substituted by 1 or 2 groups selected from Group 5,
and wherein, in the above,
Group 5 comprises a substituent selected from the group consisting of:

(1) a $C_{1-4}$ alkanoylamino group, (2) a $C_{2-6}$ alkanoyl group, (3) a mono-$C_{1-10}$ alkylcarbamoyl group, (4) a mono-$C_{1-10}$ alkylgulfamoyl group, (5) a halogen atom and (6) an oxo group.

5. The compound of claim 1, wherein
R is a hydrogen atom, $R^1$ is a $C_{1-6}$ alkyl group,
$R^2$ is (1) a phenyl group substituted by halogen or acetylamino or (2) a pyridyl group substituted by halogen or acetylamino, and
n is 0.

6. The compound of claim 1, which is 1-(4'-fluoro[1,1'-biphenyl]-4-yl)-1-(1H-imidazol-4-yl)-2-methyl-1-propanol, (−)-N-(6-{4-[1-hydroxy-1-(1H-imidazol-4-yl)-2-methylpropyl]phenyl}-2-pyridyl)acetamide, (−)-N-{4'-[1-hydroxy-1-(1H-imidazol-4-yl)-2-methylpropyl][1,1'-biphenyl]-3-yl}acetamide, 4'-[1-hydroxy-1-(1H-imidazol-4-yl)-2-methylpropyl]-N-methyl[1,1'-biphenyl]-3-carboxamide or N-[4'-[1-hydroxy-1-(1H-imidazol-4-yl)propyl][1,1'-biphenyl]-3-yl]acetamide, or a salt thereof.

7. A prodrug of a compound represented by the formula:

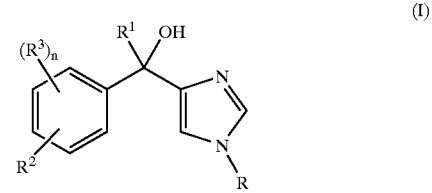

(I)

wherein
R is a hydrogen atom or a protecting group,
$R^1$ is a lower alkyl group or a cyclic hydrocarbon group,
$R^2$ is an aromatic hydrocarbon group optionally having substituents or an aromatic heterocyclic group optionally having substituents,
$R^3$ is a hydrocarbon group optionally having substituents, a hydroxyl group optionally having substituents, a thiol group optionally having substituents, an amino group optionally having substituents, an acyl group or a halogen atom, and
n is an integer of 0 to 4,
or a salt thereof.

8. A pharmaceutical composition comprising a compound represented by the formula:

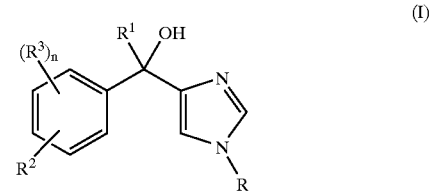

(I)

wherein
R is a hydrogen atom or a protecting group,
$R^1$ is a lower alkyl group or a cyclic hydrocarbon group,
$R^2$ is an aromatic hydrocarbon group optionally having substituents or an aromatic heterocyclic group optionally having substituents,
$R^3$ is a hydrocarbon group optionally having substituents, a hydroxyl group optionally having substituents. a thiol group optionally having substituents, an amino group optionally having substituents, an acyl group or a halogen atom, and
n is an integer of 0 to 4,
a salt thereof or a prodrug thereof.

9. A method for treating a tumor in a mammal in need thereof, said method comprising administering a composition of claim 8, to a mammal in need thereof.

10. The method of claim 9, wherein said tumor is breast cancer or prostate cancer.

11. An androgen reducer composition Comprising a compound represented by the formula;

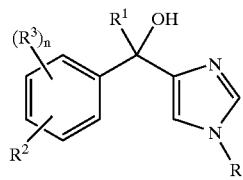
(I)

wherein
R is a hydrogen atom or a protecting group,
R¹ is a lower alkyl group or a cyclic hydrocarbon group,
R² is an aromatic hydrocarbon group optionally having substituents or an aromatic heterocyclic group optionally having substituents,
R³ is a hydrocarbon group optionally having substituents, a hydroxyl group optionally having substituents, a thiol group optionally having substituents, an amino group optionally having substituents, an acyl group or a halogen atom, and
n is an integer of 0 to 4,
or a salt thereof or a prodrug thereof, and an LHRH modulator in combination.

12. A production method of a compound represented by the formula:

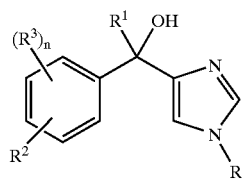
(I)

wherein
R is a hydrogen atom or a protecting group,
R¹ is a lower alkyl group or a cyclic hydrocarbon group,
R² is an aromatic hydrocarbon group optionally having substituents or an aromatic heterocyclic group optionally having substituents,
R³ is a hydrocarbon group optionally having substituents, a hydroxyl group optionally having substituents, a thiol group optionally having substituents, an amino group optionally having substituents, an acyl group or a halogen atom, and
n is an integer of 0 to 4, or a salt thereof,
which method comprises reacting a compound represented by the formula:

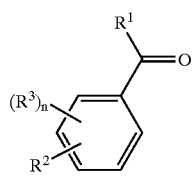
(II)

wherein each symbol is as defined above, with a reaction product of a compound represented by the formula:

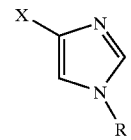
(III)

wherein X is a leaving group and R is as defined above, and a Grignard reagent or alkyllithium.

13. A method for inhibiting steroid $C_{17,20}$-lyase, which comprises administering, to a mammal, an effective amount of a compound represented by the formula:

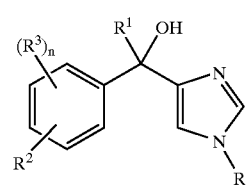
(I)

wherein
R is a hydrogen atom or a protecting group,
R¹ is a lower alkyl group or a cyclic hydrocarbon group,
R² is an aromatic hydrocarbon group optionally having substituents or an aromatic heterocyclic group optionally having substituents,
R³ is a hydrocarbon group optionally having substituents, a hydroxyl group optionally having substituents, a thiol group optionally having substituents, an amino group optionally having substituents, an acyl group or a halogen atom, and
n is an integer of 0 to 4,
or a salt or a prodrug thereof.

14. A method for making a pharmaceutical composition useful as a steroid $C_{17,20}$-lyase inhibitor comprising combining a compound represented by the formula:

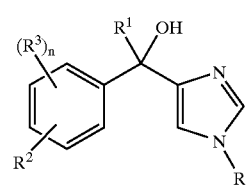
(I)

wherein
R is a hydrogen atom or a protecting group,
R¹ is a lower alkyl group or a cyclic hydrocarbon group,
R² is an aromatic hydrocarbon group optionally having substituents or an aromatic heterocyclic group optionally having substituents,
R³ is a hydrocarbon group optionally having substituents, a hydroxyl group optionally having substituents, a thiol group optionally having substituents, an amino group optionally having substituents, an acyl group or a halogen atom,
n is an integer of 0 to 4,
or a salt thereof or a prodrug thereof with a pharmaceutically acceptable carrier, excipient or diluent.

* * * * *